US 8,410,075 B2
Apr. 2, 2013

(12) United States Patent
Keana et al.

(10) Patent No.: US 8,410,075 B2
(45) Date of Patent: Apr. 2, 2013

(54) MANNICH BASE N-OXIDE DRUGS

(75) Inventors: John F. W. Keana, Eugene, OR (US);
Paul Westberg, San Mateo, CA (US);
John Curd, Hillsborough, CA (US);
Alshad S. Lalani, Briarcliff Manor, NY (US)

(73) Assignee: Cascade Prodrug Inc., Eugene, OR (US)

( * ) Notice: Subject to any disclaimer, the term of this patent is extended or adjusted under 35 U.S.C. 154(b) by 572 days.

(21) Appl. No.: 12/563,543

(22) Filed: Sep. 21, 2009

(65) Prior Publication Data
US 2010/0016252 A1    Jan. 21, 2010

Related U.S. Application Data

(63) Continuation-in-part of application No. PCT/US2008/003550, filed on Mar. 19, 2008.

(60) Provisional application No. 60/907,048, filed on Mar. 19, 2007.

(51) Int. Cl.
*A01N 43/04*    (2006.01)
*A61K 31/70*    (2006.01)

(52) U.S. Cl. ................. 514/50; 514/43; 514/49; 514/51

(58) Field of Classification Search .................... None
See application file for complete search history.

(56) References Cited

U.S. PATENT DOCUMENTS

| | | | |
|---|---|---|---|
| 3,322,747 | A | 5/1967 | Shen et al. |
| 3,349,082 | A | 10/1967 | Maggi et al. |
| 3,948,897 | A | 4/1976 | Townsend et al. |
| 4,757,139 | A | 7/1988 | Kawaguchi et al. |
| 4,845,081 | A | 7/1989 | Sloan |
| 5,032,680 | A | 7/1991 | Kawai et al. |
| 5,530,003 | A | 6/1996 | Yanagawa |
| 5,614,505 | A | 3/1997 | Gmeiner et al. |
| 5,719,132 | A | 2/1998 | Lin et al. |
| 5,808,049 | A | 9/1998 | Yamazaki et al. |
| 6,702,705 | B1 | 3/2004 | von Borstel et al. |
| 6,710,067 | B2 | 3/2004 | Moon et al. |
| 2005/0026996 | A1 | 2/2005 | Ekwuribe et al. |
| 2006/0148777 | A1 | 7/2006 | Smith et al. |

FOREIGN PATENT DOCUMENTS

WO    WO 2004/087075 A2    10/2004
WO    WO 2005/061453 A1    7/2005

OTHER PUBLICATIONS

Albertella, M.R. et al., "In vivo activation of the hypoxia-targeted cytotoxin AQ4N in human tumor xenografts," In: Proceedings of the 97th Annual Meeting of the American Association for Cancer Research, Apr. 1-5, 2006, Washington, DC. Philadelhia (PA); AACR; 2006. p. 314. Abstract No. 1330.
Alters, S.E. et al., "The cytotoxic prodrug, AQ4N, demonstrates tumor targeting and accumulation resulting in anti-tumor activity in the BxPC3 pancreatic xenograft model," In: Proceedings of the 97th Annual Meeting of the American Association for Cancer Research, Apr. 1-5, 2006, Washington, DC. Philadelphia (PA); AACR; 2006. p. 900. Abstract No. 3827.
Alters, S.E. et al., "The targeted cytotoxic prodrug, AQ4N, has significant activity in the breast adenocarcinoma model MDA-MB-231," In: Proceedings of the 97th Annual Meeting of the American Association for Cancer Research, Apr. 1-5, 2006, Washington, DC. Philadelphia (PA); AACR; 2006. pp. 1303-1304. Abstract No. 5545.
Barnett, C.J. et al., "Structure-Activity Relationships of Dimeric *Catharanthus* Alkaloids. 1. Deacetylvinblastine Amide (Vindesine) Sulfate," *J. Med. Chem.* 21:88-96, American Chemical Society (1978).
Bickel, M.H., "The Pharmacology and Biochemistry of N-Oxides," *Pharmacol. Rev.* 21:325-355, The Williams & Wilkins Co. (1969).
Bundgaard and Møss, "Prodrugs of Peptides IV: Bioreversible Derivatization of the Pyroglutamyl Group by *N*-Acylation and *N*-Aminomethylation to Effect Protection against Pyroglutamyl Aminopeptidase," *J. Pharm. Sci.* 78:122-126, American Pharmaceutical Association (1989).
Cibotti, M.C. et al., "Monoclonal Antibodies to Bis-Indole Alkaloids of *Catharanthus roseus* and Their Use in Enzyme-Linked Immuno-Sorbent-Assays," *Phytochem.* 29:2109-2114, Pergamon Press plc (1990).
Dorie, M.J. et al., "Prediction of antitumor activity of PR-104, a new hypoxia activated mustard, using measurements of DNA interstrand crosslinks by the comet assay," In: Proceedings of the 97th Annual Meeting of the American Association for Cancer Research, Apr. 1-5, 2006, Washington, DC. Philadelphia (PA); AACR; 2006. pp. 1334-1335. Abstract No. 5677.
Dorman, D.E. and Paschal, J.W., "$^{13}$C n.m.r. Spectroscopy: Comparison of the Spectra of some Dimeric *Catharanthus* Alkaloids and their Deriviatives," *Organic Magnetic Resonance* 8:413-418, Heyden & Son Limited (1976).
Evans, J.W. et al., "A cell-based screening platform for hypoxia-activated prodrugs," In: Proceedings of the 97th Annual Meeting of the American Association for Cancer Research; Apr. 1-5, 2006, Washington, DC. Philadelphia (PA): AACR; 2006. p. 321. Abstract No. 1359.
Guo, W. et al., "Reduction of benzoquinone ansamycin Hsp90 inhibitors by NQO1 generates hydroquinone ansamycins which are more potent Hsp90 inhibitors," In: Proceedings of the 97th Annual Meeting of the American Association for Cancer Research, Apr. 1-5, 2006, Washington, DC. Philadelphia (PA); AACR; 2006. p. 316. Abstract No. 1338.

(Continued)

*Primary Examiner* — Patrick Lewis
(74) *Attorney, Agent, or Firm* — Sterne, Kessler, Goldstein & Fox P.L.L.C.

(57)    ABSTRACT

Disclosed are Mannich base N-oxides of drugs containing acidic N—H groups. Pharmaceutical compositions comprising a therapeutically effective amount of Mannich base N-oxides, or a N-oxide rearrangement product, pharmaceutically acceptable salt or prodrug thereof, are also disclosed. Further, disclosed are methods of using the compounds, alone or in combination with one or more other active agents or treatments.

11 Claims, No Drawings

OTHER PUBLICATIONS

Harris, P.A. et al., "Tumor-specific activation of the hypoxic cell cytotoxin AQ4N: a NPL121 phase I clinical study in solid tumors," In: Proceedings of the 97$^{th}$ Annual Meeting of the American Association for Cancer Research, Apr. 1-5, 2006, Washington, DC. Philadelphia (PA); AACR; 2006. pp. 571-572. Abstract No. 2414.

International Search Report for International Patent Application No. PCT/US08/03550, U.S. Patent and Trademark Office, Alexandria, Virginia, mailed Jun. 12, 2008.

Lam, W. et al., "The effect of hypoxia treatment on the expression of phosphoglycerate kinase and apurine endonuclease-1 and its impact on the cytotoxicity of troxacitabine and gemcitabine," In: Proceedings of the 97$^{th}$ Annual Meeting of the American Association for Cancer Research, Apr. 1-5, 2006, Washington, DC. Philadelphia (PA); AACR; 2006. p. 907. Abstract No. 3857.

Maguire, M.H. and Csonka-Khalifah, L., "Vinca Alkaloids inhibit conversion of arachidonic acid to thromboxane by human platelet microsomes: comparison with other microtubule-active drugs," *Biochem. Biophys. Acta* 921:426-436, Elsevier Science Publishers B.V. (1987).

Mukhopadhyay, S. and Cordell, G.A., "*Catharanthus* Alkaloids. XXXV. Isolation of Leurosidine $N^{\dagger}_{b}$-Oxide from *Catharanthus roseus*," *J. Nat. Prod.* 44:611-613, American Society of Pharmacognosy (1981).

Rajendran. J.G. et al., "Assessing tumor hypoxia with F-18 FMISO PET: novel role for micro-array analysis—correlating the hypoxia genotype with tumor microenvironment," In: Proceedings of the 97$^{th}$ Annual Meeting of the American Association for Cancer Research, Apr. 1-5, 2006, Washington, DC. Philadelphia (PA); AACR; 2006. p. 260. Abstract No. 1104.

Sih, J.C. et al., "Studies on ($H^{+}$-$K^{+}$)-ATPase Inhibitors of Gastric Acid Secretion. Prodrugs of 2-[2-Pyridinylmethyl)sulfinyl] benzimidazole Proton-Pump Inhibitors," *J. Med. Chem.* 34:1049-1062, American Chemical Society (1991).

MANNICH BASE N-OXIDE DRUGS

This application is a continuation-in-part of International Appl. No. PCT/US2008/003550, filed Mar. 19, 2008, now pending. International Appl. No. PCT/US2008/003550 is a nonprovisional of U.S. Appl. No. 60/907,408, filed Mar. 19, 2007, now abandoned. The contents of these applications are fully incorporated by reference herein.

BACKGROUND OF THE INVENTION

1. Field of the Invention

The present invention relates to N-oxides of Mannich bases of drugs and prodrugs containing acidic N—H groups and having activity for treating hyperproliferative disorders and the use thereof as drugs or prodrugs. Further, the invention relates to methods of using the compounds, alone or in combination with one or more other active agents or treatments, to treat hyperproliferative disorders.

2. Related Art

One in every four deaths in the United States is due to cancer, and cancer is the second leading cause of death. U.S. Cancer Statistics Working Group; *United States Cancer Statistics: 1999-2001 Incidence*, Atlanta (Ga.): Department of Health and Human Services, Centers for Disease Control and Prevention, and National Cancer Institute (2004). The National Cancer Institute reports that almost 10 million Americans have a history of invasive cancer, while the American Cancer Society estimates that in the year 2004, over 1.3 million Americans will receive a diagnosis of invasive cancer with over a half million cases resulting in death. American Cancer Society, *Cancer Facts & Figures* 2004. These statistics exclude the 1 million cases of basal and squamous cell skin cancers that are expected to be diagnosed in the United States.

Cancers are classified based on the organ and cell tissue from which the cancer originates, including: (i) carcinomas (most common kind of cancer which originates in epithelial tissues, the layers of cells covering the body's surface or lining internal organs and various glands); (ii) leukemias (origination in the blood-forming tissues, including bone marrow, lymph nodes and the spleen); (iii) lymphomas (originates in the cells of the lymph system); (iv) melanomas (originates in the pigment cells located among the epithelial cells of the skin); and (v) sarcomas (originates in the connective tissues of the body, such as bones, muscles and blood vessels). (See Molecular Biology of the Cell: Third Edition, "Cancer," Chapter 24, pp. 1255-1294, B. Alberts et al., (eds.), Garland Publishing, Inc., New York (1994); and Stedman's Pocket Medical Dictionary; Williams and Wilkins, Baltimore (1987)). Within these broad cancer classifications, there are over one hundred cancer subclassifications, such as breast, lung, pancreatic, colon, and prostate cancer, to name a few.

Cancer cells develop as a result of damage to a cell's DNA (i.e., altered DNA sequence or altered expression pattern) from exposure to various chemical agents, radiation, viruses, or when some not-yet-fully-understood internal, cellular signaling event occurs. Most of the time when a cell's DNA becomes damaged, the cell either dies or is able to repair the DNA. However, for cancer cells, the damaged DNA is not repaired and the cell continues to divide, exhibiting modified cell physiology and function.

Neoplasms, or tumors, are masses of cells that result from an aberrant, accelerated rate of growth (i.e., hyperproliferative cell growth). As long as the tumor cells remain confined to a single mass, the tumor is considered to be benign. However, a cancerous tumor has the ability to invade other tissues and is termed malignant. In general, cancer cells are defined by two heritable properties: the cells and their progeny 1) reproduce in defiance of normal restraints, and 2) invade and colonize the territories of other cells.

Cancerous tumors are comprised of a highly complex vasculature and differentiated tissue. A large majority of cancerous tumors have hypoxic components, which are relatively resistant to standard anti-cancer treatment, including radiotherapy and chemotherapy. Brown, *Cancer Res.* 59:5863 (1999); and Kunz, M. et al., *Mol. Cancer* 2:1 (2003). Thomlinson and Gray presented the first anatomical model of a human tumor that describes a 100 to 150 μm thick hypoxic layer of tissue located between the blood vessels and necrotic tumor tissues.

Research has shown that the hypoxic tissues within a number of cancerous tumors promote the progression of the cancer by an array of complex mechanisms. See, Brown., supra, and Kunz et al., supra. Among these are activation of certain signal transduction pathways and gene regulatory mechanisms, induction of selection processes for gene mutations, tumor cell apoptosis and tumor angiogenesis. Most of these mechanisms contribute to tumor progression. Therefore, tissue hypoxia has been regarded as a central factor for tumor aggressiveness and metastasis. Therapies that target hypoxic tissues within a tumor would certainly provide improved treatments to patients suffering from tumor-related cancers and/or disorders.

In addition to cancer, there exist a number of hyperproliferative diseases and/or disorders that are associated with the onset of hypoxia in a given tissue. For example, Shweiki et al. explain that inadequate oxygen levels often lead to neovascularization in order to compensate for the needs of the hypoxic tissue. Neovascularization is mediated by expression of certain growth factors, such as vascular endothelial growth factor (VEGF). Shweiki et al., *Nature* 359:843 (1992). However, when certain tissues or growth factors are either directly or indirectly upregulated in response to hypoxia without sufficient feedback mechanisms for controlling tissue expression, various diseases and/or disorders may ensue (i.e., by hypoxia-aggravated hyperproliferation).

5-Fluorouracil (5-FU), which contains an imide N—H group, is thymidylate synthase inhibitor (antimetabolite) used for the treatment of solid tumors of the head, neck, breast, colon, rectum, liver and pancreas. Thymidylate synthase (TS) catalyzes conversion of deoxyuridine 5'-O-monophosphate (dUMP) to deoxythymidine 5'-O-monophosphate (dTMP). It is believed that 5-FU retards tumor expansion by causing thymidine pools to become depleted in rapidly proliferating tumor cells. See U.S. Pat. No. 5,614,505.

5-FU has a low therapeutic index because of its toxicity at doses lower than therapeutically effective doses, reducing the potential utility. See U.S. Pat. No. 6,702,705. This has led to the development of 5-FU analogs or prodrugs (e.g., 1-(tetrahydro-2-furanyl)-5-fluorouracil, commonly known as ftorafur or tegafur) that slowly release 5-FU upon enzymatic degradation. See, e.g., U.S. Pat. No. 5,719,132. U.S. Pat. No. 3,948,897 describes the synthesis and anti-cancer activity of tegafur, which has the following structure:

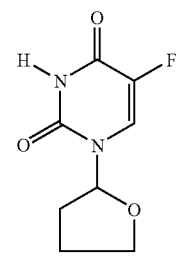 [SMILES: O=c1[nH]c(=O)n(C2CCCO2)cc1F]

5-FU must be anabolized to the level of nucleotides (e.g., fluorouridine- or fluorodeoxyuridine-5'-phosphates) in order to exert its potential cytotoxicity. The nucleosides corresponding to these nucleotides (5-fluorouridine and 5-fluoro-2'-deoxyuridine) are also active antineoplastic agents, and in some model systems are substantially more potent than 5-FU, probably because they are more readily converted to nucleotides than 5-FU is. See U.S. Pat. No. 6,702,705.

U.S. Pat. No. 3,322,747 describes a group of 5-FU analogs or prodrugs having the following structures A and B:

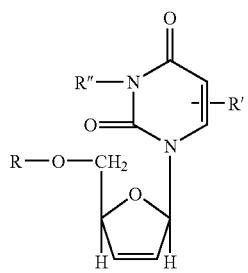

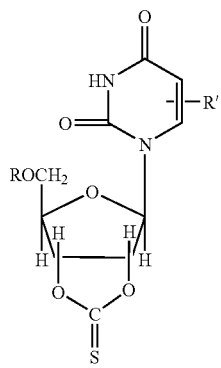

wherein R is acyl, alkyl or aralkyl; R' is hydrogen, halo, alkyl, amine, alkylamine (e.g., methylamine, dimethylamine, propylamine) or triflouromethyl amine; R" is alkyl phosphite.

U.S. Pat. No. 5,032,680 describes a group of 2'-deoxy-5-fluorouridine derivatives having the following structure:

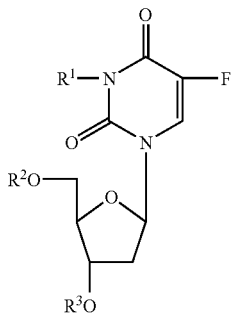

wherein $R^1$ is hydrogen or acyl and $R^2$ and $R^3$ are respectively hydrogen, acyl or a group of the formula:

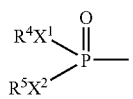

wherein $X^1$ and $X^2$ are respectively oxygen or sulfur, $R^4$ is phenyl, benzyl, or naphthyl each of which may be substituted by alkyl, alkoxyl, alkoxycarbonyl, alkylthio, acyl, halo, trifluoromethyl, nitro, cyano, carboxyl or methylenedioxy and $R^5$ is alkyl, alkenyl or $R^4$, at least one of $R^2$ and $R^3$ being a group of the formula:

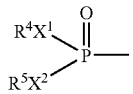

U.S. Pat. No. 4,757,139 describes a group of 5-FU analogs or prodrugs having the following structure:

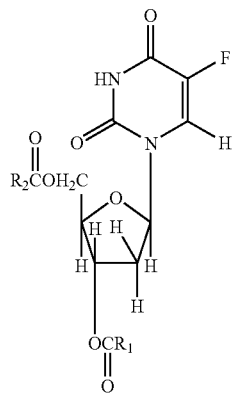

wherein $R_1$ and $R_2$ are the same or different from each other, each representing an alkyl group of 1 to 18 carbon atoms having a carboxyl group as a substituent, or an alkyl group of 9 to 14 carbon atoms, or their pharmacologically acceptable salts.

U.S. Pat. No. 5,808,049 describes a group of 5-FU analogs or prodrugs having the following structure:

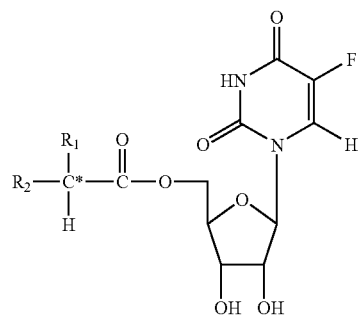

wherein $R_1$ is methyl, methoxy or trifluoracetamido; $R_2$ is phenyl, or phenylmethyl; and the absolute configuration of the chiral center is R.

U.S. Pat. No. 5,530,003 describes a 5-FU analog or prodrug having the following structure:

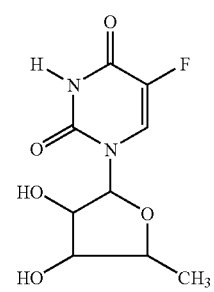 [SMILES: CC1OC(n2cc(F)c(=O)[nH]c2=O)C(O)C1O]

U.S. Pat. No. 6,702,705 ('705 patent) describes antineoplastic nucleotide analogs comprising monosaccharide hexapyranose or hexafuarnose covalently attached to the 3' or 5' oxygen of the nucleotide analog. Examples of nucleotide analogs disclosed by the '705 patent include fluorouracil, fluorodeoxyuridine, fluorouridine, arabinosyl cytosine, mercaptopurine riboside, thioguanosine, arabinosyl fluorouracil, azauridine, azacytidine, fluorcytidine, fludarabine. Disclosed monosaccharides (hexapyranose or hexafuranose) include glucose, glycosamine, D-quinovopyranose, galactose, galactosamine, L-fucopyranose, L-rhamnopyranose, D-glucopyranuronic acid, D-galactoypyranuronic acid, D-mannopyranuronic acid, D-iodopyranuronic acid, glucose, glycosamine, D-quinovopyranose, galactose, galactosamine, L-fucopyranose, L-rhamnopyranose, D-glucopyranuronic acid, D-galactoypyranuronic acid, D-mannopyranuronic acid and D-iodopyranuronic acid.

Mannich bases are known to those skilled in the art. Mannich bases, which undergo facile conversion back to the component parts under physiological conditions, have been investigated as prodrugs. See, e.g., Bundgaard, H. and Moss, J. *J. Pharm. Sci.* 78(2):122-26 (1989). However, owing to the facile conversion back to the parent drug, the use of Mannich base prodrugs is limited.

BRIEF SUMMARY OF THE INVENTION

One aspect of the invention is drawn to Mannich base N-oxide compounds having Formula I:

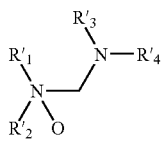

I or a N-oxide rearrangement product thereof, pharmaceutically acceptable salt or prodrug thereof, wherein:

each of $R'_1$ and $R'_2$ is independently a straight chain or branched alkyl, cycloalkyl, alkylaryl, aryl, heteroaryl, or $R'_1$ and $R'_2$ together with the nitrogen atom to which they are attached form a ring that may contain one or more heteroatoms selected from the group consisting of N, O and S; and $R'_3R'_4N$— is a residue of a drug containing an acidic N—H group.

Another aspect of the invention is drawn to compounds having formula II:

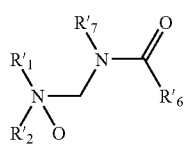

II or a N-oxide rearrangement product thereof, pharmaceutically acceptable salt or prodrug thereof, wherein $R'_1$ and $R'_2$ are as defined above; and —$R'_7NC(=O)R'_6$ group is a residue of carboxamide-containing drug or a carboxyl-containing drug that may be converted to a carboxamide.

Another aspect of the invention is drawn to compounds where the —$NR'_3R'_4$ group is a residue from a taxane e.g. having formula III:

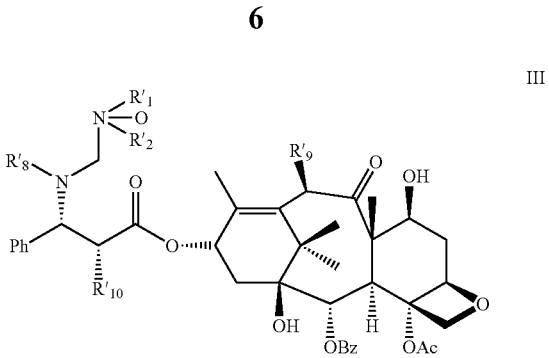

III or a pharmaceutically acceptable salt or prodrug thereof, wherein $R'_1$ and $R'_2$ are as defined above; $R'_8$ is mono or dihaloginated acyl group, aroyl group, heteroaroyl, alkoxycarbonyl, aryloxycarbonyl or heteroaryloxycabonyl, $R'_9$ is hydrogen or acyl and $R'_{10}$ is optionally substituted alkylcarbonyl, optionally substituted aryloxycarbonyl, optionally substituted aroyl, optionally substituted heteroaroyl or optionally substituted heteroaryloxycabonyl.

One aspect of the invention is drawn to compounds having Formula IV:

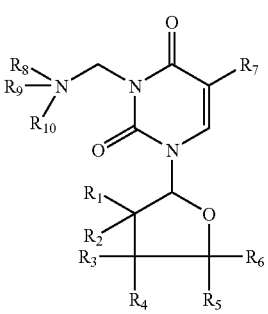

IV or a pharmaceutically acceptable salt or prodrug thereof, wherein:

each of $R_1$ and $R_2$ is independently hydrogen or hydroxy;

each of $R_3$ and $R_4$ is independently hydrogen, hydroxy; $OC(=O)R_{11}$, $OR_{12}$ or one of $R_1$ and $R_2$ and one of $R_3$ and $R_4$ together form a double bond or a —$OC(=X^3)O$— group, wherein $X^3$ is S or O;

each of $R_5$ and $R_6$ is independently hydrogen, alkyl, $CH_2OR_{13}$ or $C(=O)$—CR'R"H; wherein R' is alkyl, alkoxy, or trifluoroacetamido; R" is phenyl or phenylmethyl;

$R_7$ is hydrogen, halo, alkyl, amine, alkylamine, dialkylamine, dialkylamine N-oxide, trifluoromethyl or trifluoromethyl amine;

each of $R_8$ and $R_9$ is independently alkyl, aryl, aralkyl, alkoxyalkyl, hydroxyalkyl, or $R_8$ and $R_9$ together with the nitrogen to which they are attached form a heterocyclic ring comprising one, two or three heteroatoms selected from the group consisting of N, O, S, SO and $SO_2$, said heterocycle is optionally substituted with 1-4 substituents selected from the group consisting of hydroxy, alkoxy, halogen or hydroxyalkyl;

$R_{10}$ is O or is absent, provided that $R_{10}$ is O when $R_7$ is not dialkylamine N-oxide;

$R_{11}$ is hydrogen, acyl, alkylcarboxy, alkyl;

$R_{12}$ is hydrogen, acyl or a group of the formula:

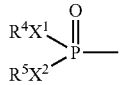

wherein $X^1$ and $X^2$ are independently O or S; $R^4$ is optionally substituted phenyl, optionally substituted benzyl or optionally substituted naphthyl; $R^5$ is alkyl or alkenyl; and $R_{13}$ is hydrogen, acyl, alkylcarboxy, alkyl, aralkyl, a monosaccharide, or a group of the formula:

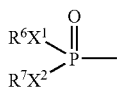

wherein $X^1$ and $X^2$ are independently O or S; $R^6$ is optionally substituted phenyl, optionally substituted benzyl or optionally substituted naphthyl; $R^7$ is alkyl or alkenyl.

In one aspect the invention is drawn to compounds having formula V:

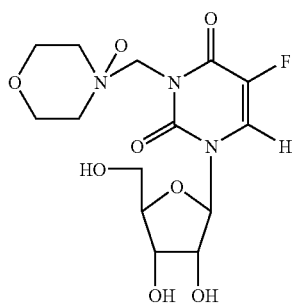

V or a pharmaceutically acceptable salt or prodrug thereof.

In another aspect the invention is drawn to compounds having formula VI:

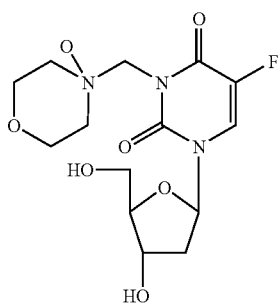

VI or a pharmaceutically acceptable salt or prodrug thereof.

In yet another aspect the invention is drawn to tegafur Mannich base N-oxide having Formula VII:

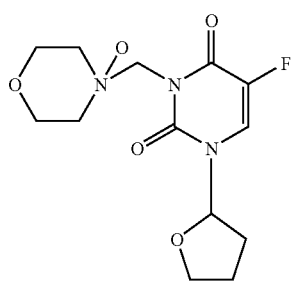

VII or a pharmaceutically acceptable salt or prodrug thereof.

In one embodiment, the compounds having formula IV are Mannich base N-oxides of 5-FU analogs or prodrugs selected from the group consisting of:
tegafur;
5-fluorouridine-5'-phosphates;
5-fluorodeoxyuridine-5'-phosphates;
5-fluorouridine;
5-fluoro-2'-deoxyuridine;
1-(5'-O-trityl-β-D-ribofuranosyl)-uracil-2',3'-O-thionocarbonate;
1-(5'-O-trityl-β-D-ribofuranosyl)-5-chlorouracil-2',3'-O-thionocarbonate;
1-(5'-O-trityl-β-D-ribofuranosyl)-5-methylaminouracil-2',3'-O-thionocarbonate;
1-(5'-O-trityl-β-D-ribofuranosyl)-5-methyluracil-2',3'-O-thionocarbonate;
1-(5'-O-trityl-β-D-ribofuranosyl)-5-trifluoromethyluracil-2',3'-O-thionocarbonate;
1-(5'-O-benzyl-β-D-ribofuranosyl)-uracil-2',3'-O-thionocarbonate;
1-(5'-O-benzyl-β-D-ribofuranosyl)-5-bromouracil-2',3'-O-thionocarbonate;
1-(5'-O-benzyl-β-D-ribofuranosyl)-5-aminouracil-2',3'-O-thionocarbonate;
1-(5'-O-acetyl-β-D-ribofuranosyl)-uracil-2',3'-O-thionocarbonate;
1-(5'-O-acetyl-β-D-ribofuranosyl)-5-trifluoromethyluracil-2',3'-thionocarbonate;
1-(5'-O-benzoyl-β-D-ribofuranosyl)-uracil-2',3'-O-thionocarbonate;
1-(5'-O-benzoyl-β-D-ribofuranosyl)-5-bromouracil-2',3'-O-thionocarbonate;
1-(5'-O-benzoyl-β-D-ribofuranosyl)-5-ethyluracil-2',3'-O-thionocarbonate;
1-(5'-0-trityl-β-D-ribofuranosyl)-2',3'-dideoxy-2',3'-didehydro-5-chlorouracil;
1-(5'-O-trityl-β-D-ribofuranosyl)-2',3'-dideoxy-2',3'-didehydro-5-aminouracil;
1-(5'-O-trityl-β-D-ribofuranosyl)-2',3'-dideoxy-2',3'-didehydro-5-trifluoromethyluracil;
1-(5'-O-trityl-β-D-ribofuranosyl)-2',3'-dideoxy-2',3'-didehydro-5-methylaminouracil;
1-(5'-O-trityl-β-D-ribofuranosyl)-2',3'-dideoxy-2',3'-didehydro-5-dimethylaminouracil;
1-(5'-O-benzyl-β-D-ribofuranosyl)-2',3'-dideoxy-2',3'-didehydro-5-chlorouracil;
1-(5'-O-benzyl-β-D-ribofuranosyl)-2',3'-dideoxy-2',3'-didehydro-5-aminouracil;
1-(5'-O-acetyl-β-D-ribofuranosyl)-2',3'-dideoxy-2',3-didehydro-5-methylaminouracil;
1-(5'-O-trityl-β-D-ribofuranosyl)-2',3'-dideoxy-2',3'-didehydro-3-methyluracil;
1-(5'-O-trityl-β-D-ribofuranosyl)-2',3'-dideoxy-2',3'-didehydro-3-methyl-5-chlorouracil;
1-(5'-O-benzyl-β-D-ribofuranosyl)-2',3'-dideoxy-2',3'-didehydro-3-ethyluracil;
1-(5'-O-benzyl-β-D-ribofuranosyl)-2',3'-dideoxy-2',3'-didehydro-3-ethyl-5-methylaminouracil;
1-(5'-O-trityl-β-D-ribofuranosyl-2',3'-dideoxy-2',3'-didehydrouracil;
1-(5'-O-trityl-β-D-ribofuranosyl)-2',3'-dideoxy-2',3'-didehydro-5-chlorouracil;
1-(5'-O-trityl-β-D-ribofuranosyl)-2',3'-dideoxy-2',3'-didehydrouracil-5-methylaminouracil;
1-(5'-O-trityl-β-D-ribofuranosyl)-2',3'-dideoxy-2',3'-didehydrouracil-5-methyluracil;

1-(5'-O-trityl-β-D-ribofuranosyl)-2',3'-dideoxy-2',3'-didehydrouracil-5-trifluoromethyluracil;
1-(5'-O-benzyl-β-D-ribofuranosyl)-2',3'-dideoxy-2',3'-didehydrouracil-uracil;
1-(5'-O-acetyl-β-D-ribofuranosyl)-2',3'-dideoxy-2',3'-didehydrouracil-uracil;
diphenyl-2'-deoxy-5-fluoro-5'-uridylate;
diphenyl-2'-deoxy-5-fluoro-3'-uridylate;
diphenyl-2'-deoxy-5'-O-(diphenoxyphosphinyl)-5-fluoro-3'-uridylate;
diphenyl-3-benzoyl-2'-deoxy-5-fluoro-5'-uridylate;
di-p-methylphenyl-2'-deoxy-5-fluoro-5'-uridylate;
di-p-n-hexylphenyl-2'-deoxy-5-fluoro-5'-uridylate;
di-p-methoxyphenyl-2'-deoxy-5-fluoro-5'-uridylate;
di-m-n-hexyloxyphenyl-2'-deoxy-5-fluoro-5'-uridylate;
di-p-methoxycarbonylphenyl-2'-deoxy-5-fluoro-5'-uridylate;
di-m-methoxycarbonylphenyl-2'-deoxy-5-fluoro-5'-uridylate;
di-p-n-hexyloxycarbonylphenyl-2'-deoxy-5-fluoro-5'-uridylate;
di-p-methylthiophenyl-2'-deoxy-5-fluoro-5'-uridylate;
di-p-n-hexylthiophenyl-2'-deoxy-5-fluoro-5'-uridylate;
di-m-acetylphenyl-2'-deoxy-5-fluoro-5'-uridylate;
di-p-acetylphenyl-2'-deoxy-5-fluoro-5'-uridylate;
di-p-benzoylphenyl-2'-deoxy-5-fluoro-5'-uridylate;
di-m-fluorophenyl-2'-deoxy-5-fluoro-5'-uridylate;
di-p-fluorophenyl-3-p-hexyloxycarbonylbenzoyl-2'-deoxy-5-fluoro-5'-uridylate;
di-p-fluorophenyl-3-p-nitrobenzoyl-2'-deoxy-5-fluoro-5'-uridylate;
di-p-fluorophenyl-2'-deoxy-5-fluoro-5'-uridylate;
di-p-fluorophenyl-3-(3,4-methylenedioxybenzoyl)-2'-deoxy-5-fluoro-5'-uridylate;
di-o-chlorophenyl-2'-deoxy-5-fluoro-5'-uridylate;
di-m-chlorophenyl-2'-deoxy-5-fluoro-5'-uridylate;
di-m-chlorophenyl-3-m-methoxybenzoyl-2'-deoxy-5-fluoro-5'-uridylate;
di-m-chlorophenyl-3-p-methylbenzoyl-2'-deoxy-5-fluoro-5'-uridylate;
di-p-chlorophenyl-2'-deoxy-5-fluoro-5'-uridylate;
di-p-chlorophenyl-3-formyl-2'-deoxy-5-fluoro-5'-uridylate;
di-p-chlorophenyl-3'-O-acetyl-2'-deoxy-5-fluoro-5'-uridylate;
di-p-chlorophenyl-3'-O-butyryl-2'-deoxy-5-fluoro-5'-uridylate;
di-p-chlorophenyl-3'-O-benzoyl-2'-deoxy-5-fluoro-5'-uridylate;
di-p-chlorophenyl-3'-O-m-methylbenzoyl-2'-deoxy-5-fluoro-5'-uridylate;
di-p-chlorophenyl-3-acetyl-2'-deoxy-5-fluoro-5'-uridylate;
di-p-chlorophenyl-3-benzoyl-2'-deoxy-5-fluoro-5'-uridylate;
di-p-chlorophenyl-3-m-methylbenzoyl-2'-deoxy-5-fluoro-5'-uridylate;
di-p-chlorophenyl-3-(3,4-methylenedioxybenzoyl)-2'-deoxy-5-fluoro-5'-uridylate;
di-p-chlorophenyl-3'-O-acetyl-3-benzoyl-2'-deoxy-5-fluoro-5'-uridylate;
di-m-bromophenyl-2'-deoxy-5-fluoro-5'-uridylate;
di-p-bromophenyl-3'-O-hexanoyl-2'-deoxy-5-fluoro-5'-uridylate;
di-p-bromophenyl-2'-deoxy-5-fluoro-5'-uridylate;
di-m-trifluoromethylphenyl-2'-deoxy-5-fluoro-5'-uridylate;
di-m-trifluoromethylphenyl-3'-O-propionyl-2'-deoxy-5-fluoro-5'-uridylate;
di-m-trifluoromethylphenyl-3'-O-butyryl-2'-deoxy-5-fluoro-5'-uridylate;
di-p-trifluoromethylphenyl-2'-deoxy-5-fluoro-5'-uridylate;
di-p-trifluoromethylphenyl-3-(3,4-methylenedioxybenzoyl)-2'-deoxy-5-fluoro-5'-uridylate;
di-o-cyanophenyl-2'-deoxy-5-fluoro-5'-uridylate;
di-m-cyanophenyl-2'-deoxy-5-fluoro-5'-uridylate;
di-p-cyanophenyl-2'-deoxy-5-fluoro-5'-uridylate;
di-p-cyanophenyl-3-m-methoxybenzoyl-2'-deoxy-5-fluoro-5'-uridylate;
di-o-nitrophenyl-2'-deoxy-5-fluoro-5'-uridylate;
di-o-nitrophenyl-3-hexanoyl-2'-deoxy-5-fluoro-5-uridylate;
di-m-nitrophenyl-2'-deoxy-5-fluoro-5'-uridylate;
di-p-nitrophenyl-2'-deoxy-5-fluoro-5'-uridylate;
di-p-nitrophenyl-3'-O-acetyl-2'-deoxy-5-fluoro-5'-uridylate;
di-p-nitrophenyl-3-(3,4-methylenedioxybenzoyl)-2'-deoxy-5-fluoro-5'-uridylate;
di-p-carboxyphenyl-2'-deoxy-5-fluoro-5'-uridylate;
di-p-carboxyphenyl-3-(1-naphthoyl)-2'-deoxy-5-fluoro-5'-uridylate;
di-(3,4-methylenedioxyphenyl)-2'-deoxy-5-fluoro-5'-uridylate;
di-(3,4-methylenedioxyphenyl)-3'-butyryl-2'-deoxy-5-fluoro-5'-uridylate;
di-(2,3-dichlorophenyl)-2'-deoxy-5-fluoro-5'-uridylate;
di-(2,4-dichlorophenyl)-2'-deoxy-5-fluoro-5'-uridylate;
di-(2,4-dichlorophenyl)-3'-O-acetyl-2'-deoxy-5-fluoro-5'-uridylate;
di-(3,4-dichlorophenyl)-2'-deoxy-5-fluoro-5'-uridylate;
di-(3,5-dichlorophenyl)-2'-deoxy-5-fluoro-5'-uridylate;
di-(4-chloro-3-methylphenyl)-2'-deoxy-5-fluoro-5'-uridylate;
di-(2-bromo-4-methylphenyl)-2'-deoxy-5-fluoro-5'-uridylate;
di-(2-chloro-4-nitrophenyl)-2'-deoxy-5-fluoro-5'-uridylate;
di-(3,4-dimethylphenyl)-3'-O-acetyl-2'-deoxy-5-fluoro-5'-uridylate;
di-(2,3,5-trichlorophenyl)-2'-deoxy-5-fluoro-5'-uridylate;
di-(2,3,5-trimethylphenyl)-2'-deoxy-5-fluoro-5'-uridylate;
di-1-naphthyl-2'-deoxy-5-fluoro-5'-uridylate;
di-2-naphthyl-2'-deoxy-5-fluoro-5'-uridylate;
di-4-methoxycarbonylphenyl-2'-deoxy-5-fluoro-5'-uridylate;
di-(2,4-dichloro-1-naphthyl)-2'-deoxy-5-fluoro-5'-uridylate;
dibenzyl-2'-deoxy-5-fluoro-5'-uridylate;
di-(4-chloro-3-nitrobenzyl)-2'-deoxy-5-fluoro-5'-uridylate;
2'-deoxy-5-fluorouridine-5'-(S,S-diphenylphosphorodithioate);
2'-deoxy-5-fluorouridine-5'-(S,S-di-p-methoxyphenylphosphorodithioate);
2'-deoxy-5-fluorouridine-5'-(S,S-di-p-chlorophenylphosphorodithioate);
p-chlorophenyl-phenyl-2'-deoxy-5-fluoro-5'-uridylate;
p-chlorophenyl-phenyl-2'-deoxy-5-fluoro-3'-uridylate;
p-chlorophenyl-p-bromophenyl-2'-deoxy-5-fluoro-5'-uridylate;
4-chloro-3-methylphenylphenyl-2'-deoxy-5-fluoro-5'-uridylate;
methyl-phenyl-2'-deoxy-5-fluoro-5'-uridylate;
n-butyryl-phenyl-2'-deoxy-5-fluoro-5'-uridylate;
n-dodecyl-phenyl-2'-deoxy-5-fluoro-5'-uridylate;
citroneryl-phenyl-2'-deoxy-5-fluoro-5'-uridylate;
geranyl-phenyl-2'-deoxy-5-fluoro-5'-uridylate;
citroneryl-p-chlorophenyl-2'-deoxy-5-fluoro-5'-uridylate;
3',5'-dimalonyl-5-fluoro-2'-deoxyuridine;
3',5'-disuccinyl-5-fluoro-2'-deoxyuridine;
3',5'-diglutaryl-5-fluoro-2'-deoxyuridine;
3',5'-diadipoyl-5-fluoro-2'-deoxyuridine;

3',5'-dipymeryl-5-fluoro-2'-deoxyuridine;
3',5'-disuberyl-5-fluoro-2'-deoxyuridine;
3',5'-disubesyl-5-fluoro-2'-deoxyuridine;
3',5'-didecanoyl-5-fluoro-2'-deoxyuridine;
3',5'-didodecanoyl-5-fluoro-2'-deoxyuridine;
3',5'-ditetradecanoyl-5-fluoro-2'-deoxyuridine;
3',5'-diadipoyl-5-fluoro-2'-deoxyuridine;
3',5'-diglutaryl-5-fluoro-2'-deoxyuridine;
3',5'-disuccinyl-5-fluoro-2'-deoxyuridine;
3',5'-bis-(β-carboxyundecanoyl)-5-fluoro-2'-deoxyuridine;
3',5'-bis-(β-carboxytridecanoyl)-5-fluoro-2'-deoxyuridine;
3',5'-bis-(β-carboxypentadecanoyl)-5-fluoro-2'-deoxyuridine;
3',5'-bis-(3-carboxy-3-methylpentanoyl)-5-fluoro-2'-deoxyuridine;
5'-(RS)-(2-phenylpropionyl)-5-fluorouridine;
5'-(RS)-(2-methoxy-2-phenylacetyl)-5-fluorouridine; and
5'-(RS)-(2-trifluoroacetamido-3-phenylpropionyl)-5-fluorouridine.

In another aspect, the invention is drawn to a compound having Formula X:

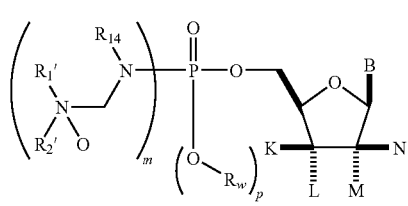

X or a N-oxide rearrangement product thereof, pharmaceutically acceptable salt or prodrug thereof, wherein:

$R_{14}$ is hydrogen, optionally substituted lower alkyl, or optionally substituted aryl;

$R_w$ is optionally substituted alkyl or optionally substituted aryl;

K, L, M, and N are independently selected from the group consisting of H, OH, $OR_{15}$, $N_3$, and halogen; or K and N taken together form a double bond;

$R_{15}$ is acyl or a group of the formula:

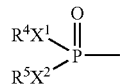

wherein $X^1$ and $X^2$ are independently O or S; $R^4$ is optionally substituted phenyl, optionally substituted benzyl or optionally substituted naphthyl; and $R^5$ is alkyl or alkenyl;

B is a residue of a nucleobase or nucleobase-related compound;

m is 1 or 2; and p is 0 or 1, with the proviso that:
1) when m is 1 then p is 1; and
2) when m is 2 then p is 0.

According to another aspect of the invention, a therapeutically effective amount of a compound having Formula I is provided in the form of a pharmaceutical composition having at least one pharmaceutically acceptable carrier. In one embodiment, the pharmaceutical composition further comprises one or more active agents or treatments. In another embodiment, the one or more active agent or treatment is a chemotherapeutic agent, a radiotherapeutic agent/treatment, an anti-angiogenesis agent, a vascular targeting agent, a hypoxia-inducible factor 1 (HIF1) inhibitor, an Hsp90 inhibitor, a tyrosine kinase inhibitor, a serine/threonine kinase inhibitor, a proteasome inhibitor, an HDAC inhibitor, a caspase inducer, a CDK inhibitor, and a proapoptotic molecule.

In one embodiment the invention is drawn to methods of treating, ameliorating, or preventing hyperproliferative disease in a subject comprising administering to said subject a therapeutically effective amount of a compound having formula I of the present invention.

An additional aspect of the present invention is a method for treating, ameliorating, or preventing hyperproliferative disorders in an animal comprising administering to the animal a therapeutically effective amount of a compound having Formula I in combination with one or more active agents or treatments. In one embodiment, the one or more active agent or treatment is a chemotherapeutic agent, a radiotherapeutic agent/treatment, an anti-angiogenesis agent, a vascular targeting agent, a hypoxia-inducible factor 1 (HIF1) inhibitor, an Hsp90 inhibitor, a tyrosine kinase inhibitor, a serine/threonine kinase inhibitor, a proteasome inhibitor, an HDAC inhibitor, a caspase inducer, a CDK inhibitor, and a proapoptotic molecule. In another embodiment, the one or more active agent or treatment is used, has been used, or is known to be useful for the treatment of the hyperproliferative disorder.

In one embodiment, the method of treating, ameliorating, or preventing hyperproliferative disorder in an animal comprises administering to the animal a therapeutically effective amount of a compound of the present invention. In particular embodiments, the compound is tegafur in combination with one or more active agents or treatments, for example, chemotherapeutic agents or radiotherapeutic agents/treatments.

In particular embodiments of the invention, the one or more chemotherapeutic agents can be any chemotherapeutic agent which is used, has been used, or is known to be useful for the treatment of hyperproliferative disorders.

In particular embodiments of the invention, the one or more radiotherapeutic agents or treatments can be external-beam radiation therapy, brachytherapy, thermotherapy, radiosurgery, charged-particle radiotherapy, neutron radiotherapy, photodynamic therapy, or radionuclide therapy.

In one embodiment of the invention, the compound having Formula I can be administered prior to, during, and/or beyond administration of the one or more chemotherapeutic agents or radiotherapeutic agents or treatments. In another embodiment of the invention, the method of administering a compound having Formula I in combination with one or more chemotherapeutic agents or radiotherapeutic agents or treatments is repeated more than once.

The combination of a compound having Formula I and one or more chemotherapeutic agents or radiotherapeutic agents or treatments of the present invention will have additive potency or an additive therapeutic effect. The invention also encompasses synergistic combinations where the therapeutic efficacy is greater than additive. Preferably, such combinations will reduce or avoid unwanted or adverse effects. In certain embodiments, the combination therapies encompassed by the invention will provide an improved overall therapy relative to administration of a compound having Formula I or any chemotherapeutic agent or radiotherapeutic agent or treatment alone. In certain embodiments, doses of existing or experimental chemotherapeutic agents or radiotherapeutic agents or treatments will be reduced or administered less frequently which will increase patient compliance, thereby improving therapy and reducing unwanted or adverse effects.

Further, the methods of the invention will be useful not only with previously untreated patients but also will be useful in the treatment of patients partially or completely refractory to current standard and/or experimental cancer therapies, including but not limited to radiotherapies, chemotherapies, and/or surgery. In a particular embodiment, the invention will provide therapeutic methods for the treatment or amelioration of hyperproliferative disorders that have been shown to be or may be refractory or non-responsive to other therapies.

While not wishing to be bound by any theory, it is believed that some of the N-oxide compounds of the invention will function as prodrugs with greatly diminished cytotoxicity because the N-oxide derivative of the Mannich base reduces or abolishes the cytotoxic activity of the parent compound. It is believed that these N-oxide compounds will be activated under hypoxic conditions within the target tissues (i.e., reduced at the nitrogen atom), exerting their cytotoxic effect on the cells by either inducing cell death or diminishing the cells' ability to replicate. Other N-oxide compounds of the invention may have intrinsic cytotoxic activity when the N-oxide Mannich base derivative does not significantly reduce the cytotoxic activity of the parent compound. Since a number of pathological tissues have significant hypoxic components which promote hyperproliferation, it is believed that this portion of tissue will be preferentially targeted.

DETAILED DESCRIPTION OF THE INVENTION

One aspect of the invention is drawn to Mannich base N-oxide compounds having Formula I:

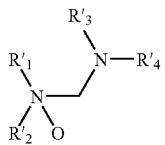

I or a N-oxide rearrangement product thereof, pharmaceutically acceptable salt or prodrug thereof, wherein $R'_1$-$R'_4$ are as defined above.

In one embodiment, one of $R'_3$ and $R'_4$, together with or without the N to which they are attached, is part of an optionally substituted 5-7 membered heterocyclic ring comprising 1-3 heteroatoms selected from the group consisting of O, N, S and P, said heterocycle is optionally fused with optionally substituted 5-7 membered carbocycle or heterocycle; the other of $R'_3$ and $R'_4$ is hydrogen, alkyloxycarbonyl, optionally substituted alkyl or optionally substituted phenyl.

In another embodiment, $R'_3$ and $R'_4$ together with the nitrogen atom to which they are attached form an optionally substituted 5-7 membered heterocyclic ring comprising 1-3 groups selected from the group consisting of —N—, —O—, —S—, —C(=O)—, —C=N—, —SO$_2$—, —PO$_2$— and —CX$_2$—, which heterocyclic ring is optionally fused with an optionally substituted 5-7 membered carbocycle or heterocycle, and wherein X is selected from the group consisting of hydrogen and alkyl.

In another embodiment, the group —NR'$_3$R'$_4$ is a residue of a drug containing an acidic N—H group, including, without limitation, cytarabine (Cytosar-U®), 5-azacytidine (Vidaza™), 5-aza-2'-deoxycytidine, 6-cyclohexylmethoxy-2-(4'-sulfamoylanilino)purine, 6-benzylamino-2-(2-hydroxyethylamino)-9-methylpurine, (2R)-2-[[6-[3-chlorophenylamino]-9-methylethyl)-9H-purin-2yl]amino]-3-methyl-1-butanol (Purvalanol A), (2R)-2-[[6-[3-chloro-4-carboxyphenylamino]-9-methylethyl)-9H-purin-2yl] amino]-3-methyl-1-butanol (Purvalanol B), carmustine, dacarbazine, floxuridine, lomustine, mercaptopurine, methotrexate, thioguanine, tetracycline, chlorotetracycline, oxytetracycline, minocycline, doxycycline, indirubin, indirubin-3'-oxime, indirubin-5-sulfonic acid, 5-chloroindirubin, 4-[[2-(3-methylbut-2-enyl)-1H-indol-3-yl]methyl]-3,6-diazabicyclo[4.3.0]nonane-2,5-dione (tryprostatin A), 4-[[2-(3-methylbut-2-enyl)-6-methoxy-1H-indol-3-yl]methyl]-3,6-diazabicyclo[4.3.0]nonane-2,5-dione (tryprostatin B), monastrol, DHP2, capecitabine (CAP), (3R,4S,5S,6R)-5-methoxy-4-[(2R,3R)-2-methyl-3-(3-methyl-2-butenyl)oxiranyl]-1-oxaspiro[2.5]oct-6-yl chloroacetylcarbamate (also known as O-(chloroacetylcarbamoyl)fumagillol or TNP-470), 7,12-dihydroindolo[3,2-d][1]benzazepin-6(5H)-one (Paullone), 9-bromo-7,12-dihydroindolo[3,2-d][1]benzazepin-6(5H)-one (Kenpaullone), 6-(benzylamino)-2-(2-hydroxyethylamino)-9-methylpurine (Olomoucine), taxane (such as those disclosed by U.S. Pat. Nos. 6,815,462, 6,884,817, 6,765,015, 6,476,242 and 5,688,977), temozolomide, cyclophosphamide and its analogs (such as those disclosed by U.S. Pat. No. 5,190,929), melphalan and its derivatives (such as those disclosed by U.S. Pat. No. 5,075,108) and mitomycin and its derivatives (such as those disclosed by U.S. Pat. No. 4,652,644).

Another embodiment is drawn to compounds having formula II:

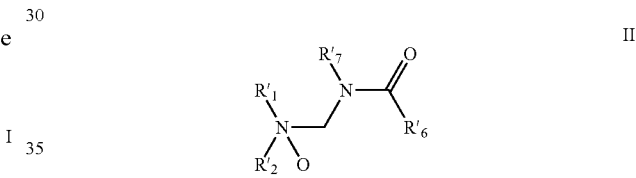

II or a N-oxide rearrangement product thereof, pharmaceutically acceptable salt or prodrug thereof, wherein $R'_1$, $R'_2$, $R'_6$ and $R'_7$ are as defined above.

In one embodiment, —R'$_7$NC(=O)R'$_6$ group is a residue of a drug containing an acidic N—H group including, without limitation, indirubin-3'-oxime, indirubin-5-sulfonic acid, 5-chloroindirubin, tryprostatin A, tryprostatin B, TNP-470, paullone, kenpaullone, eniluracil, taxane, temozolomide, melphalan and its derivatives and mitomycin and its derivatives.

Another embodiment is drawn to Mannich base N-oxide of a taxane having formula III:

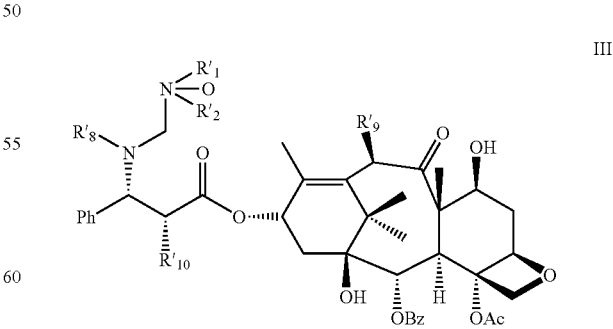

III or a pharmaceutically acceptable salt or prodrug thereof, wherein $R'_1$, $R'_2$, $R'_8$, $R'_9$ and $R'_{10}$ are as defined above. In a further embodiment, the taxane is paclitaxel, docetaxel, nonataxel or abraxane.

Another embodiment is drawn to compounds having Formula IV:

or a pharmaceutically acceptable salt or prodrug thereof, wherein:

$R_1$-$R_{10}$ are as defined above.

Another embodiment is drawn to the compound of Formula V:

or a pharmaceutically acceptable salt or prodrug thereof.

Another embodiment is drawn to the compound of Formula VI:

or a pharmaceutically acceptable salt or prodrug thereof.

Another embodiment is drawn to tegafur Mannich base N-oxide having Formula VII:

or a pharmaceutically acceptable salt or prodrug thereof.

Another embodiment is drawn to a compound having Formula X:

or a N-oxide rearrangement product thereof, pharmaceutically acceptable salt or prodrug thereof, wherein:

$R_{14}$ is hydrogen, optionally substituted lower alkyl, or optionally substituted aryl;

$R_w$ is optionally substituted lower alkyl or optionally substituted aryl;

K, L, M, and N are independently selected from the group consisting of H, OH, $OR_{15}$, $N_3$, and halogen; or K and N taken together form a double bond;

$R_{15}$ is acyl or a group of the formula:

wherein $X^1$ and $X^2$ are independently O or S; $R^4$ is optionally substituted phenyl, optionally substituted benzyl or optionally substituted naphthyl; and $R^5$ is alkyl or alkenyl;

B is a residue of a nucleobase or nucleobase-related compound;

m is 1 or 2; and p is 0 or 1, with the proviso that:

1) when m is 1 then p is 1; and 2) when m is 2 then p is 0.

According to this embodiment, the N—H bond in the phosphoramidate serves as the N—H acidic site for Mannich base N-oxide derivatization.

In another embodiment, the residue of a nucleobase or nucleobase-related compound is selected from the group consisting of:

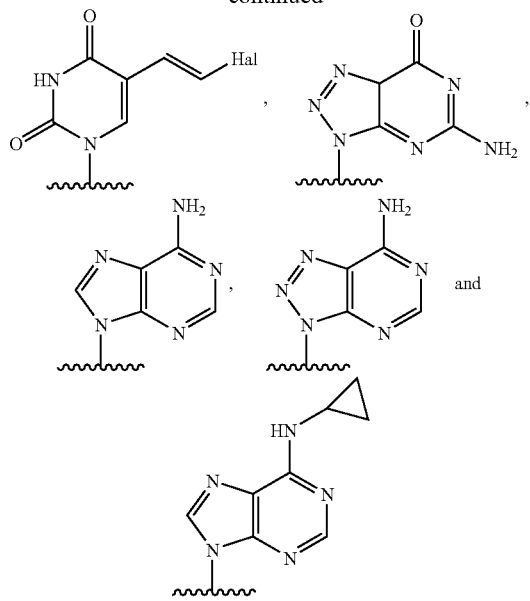

wherein hal is F, Cl, Br, or I.

In another embodiment, a pharmaceutical composition of the present invention comprises a therapeutically effective amount of a Mannich base N-oxide of a drug containing an acidic N—H group including 5-azacytidine, 5-aza-2'-deoxycytidine, carmustine, dacarbazine, floxuridine, lomustine, mercaptopurine, methotrexate, thioguanine, 6-cyclohexylmethoxy-2-(4'-sulfamoylanilino)purine, 6-benzylamino-2-(2-hydroxyethylamino)-9-methylpurine, (2R)-2-[[6-[3-chlorophenylamino]-9-methylethyl)-9H-purin-2yl]amino]-3-methyl-1-butanol, indirubin-3'-oxime, indirubin-5-sulfonic acid, 5-chloroindirubin, tryprostatin A, tryprostatin B, monastrol, DHP2, CAP, TNP-470, paullone, kenpaullone, taxane, temozolomide, cyclophosphamide and its analogs, melphalan and its derivatives and mitomycin and its derivatives.

According to another embodiment, a therapeutically effective amount of a compound having Formula I, or a pharmaceutically acceptable salt thereof, and at least one other active agent is provided in the form of a pharmaceutical composition having at least one pharmaceutically acceptable carrier. In certain instances, the at least one other active agent is a chemotherapeutic agent. Compounds having Formula I may be formulated in a single formulation with the other active agent(s), or formulated independently.

According to another embodiment, methods for treating, ameliorating, or preventing hyperproliferative disorders are provided, wherein a therapeutically effective amount of a compound having Formula I, or a pharmaceutically acceptable salt thereof, is administered to an animal in need thereof. In certain embodiments, the hyperproliferative disorder is cancer. In one embodiment, the cancer is a solid tumor. In another embodiment, the cancer is selected from the group consisting of colon cancer, brain cancer, glioma, multiple myeloma, head and neck cancer, hepatocellular cancer, melanoma, ovarian cancer, cervical cancer, renal cancer, and non-small cell lung cancer. In a further embodiment, the cancer is acute and chronic lymphocytic leukemia, acute granulocytic leukemia, adrenal cortex carcinoma, bladder carcinoma, breast carcinoma, cervical carcinoma, cervical hyperplasia, choriocarcinoma, chronic granulocytic leukemia, chronic lymphocytic leukemia, colon carcinoma, endometrial carcinoma, esophageal carcinoma, essential thrombocytosis, genitourinary carcinoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, osteogenic sarcoma, ovarian carcinoma, pancreatic carcinoma, polycythemia vera, primary brain carcinoma, primary macroglobulinemia, prostatic carcinoma, renal cell carcinoma, rhabdomyosarcoma, skin cancer, small-cell lung carcinoma, soft-tissue sarcoma, squamous cell carcinoma, stomach carcinoma, testicular carcinoma, thyroid carcinoma, or Wilms' tumor.

In another embodiment, the hyperproliferative disorder is any one of age-related macular degeneration, Crohn's disease, cirrhosis, chronic inflammatory-related disorders, proliferative diabetic retinopathy, proliferative vitreoretinopathy, retinopathy of prematurity, granulomatosis, immune hyperproliferation associated with organ or tissue transplantation, an immunoproliferative disease or disorder, e.g., inflammatory bowel disease, psoriasis, rheumatoid arthritis, systemic lupus erythematosus (SLE), vascular hyperproliferation secondary to retinal hypoxia, or vasculitis.

Another embodiment relates to methods for treating, ameliorating, or preventing a hyperproliferative disorder comprising administering a therapeutically effective amount of a compound having Formula I, or a pharmaceutically acceptable salt thereof, in combination with at least one other active agent or treatment to a patient in need thereof. In certain embodiments, combinations of a compound having Formula I with a chemotherapeutic agent are administered.

Hyperproliferative disorders which can be treated with the compounds having Formula I include any hypoxia-aggravated hyperproliferative disease and/or disorder, such as any number of cancers. Generally, such cancers include, without limitation, cancers of the bladder, brain, breast, cervix, colon, endometrium, esophagus, head and neck, kidney, larynx, liver, lung, oral cavity, ovaries, pancreas, prostate, skin, stomach, and testis. Certain of these cancers may be more specifically referred to as acute and chronic lymphocytic leukemia, acute granulocytic leukemia, adrenal cortex carcinoma, bladder carcinoma, breast carcinoma, cervical carcinoma, cervical hyperplasia, choriocarcinoma, chronic granulocytic leukemia, chronic lymphocytic leukemia, colon carcinoma, endometrial carcinoma, esophageal carcinoma, essential thrombocytosis, genitourinary carcinoma, hairy cell leukemia, head and neck carcinoma, Hodgkin's disease, Kaposi's sarcoma, lung carcinoma, lymphoma, malignant carcinoid carcinoma, malignant hypercalcemia, malignant melanoma, malignant pancreatic insulinoma, medullary thyroid carcinoma, melanoma, multiple myeloma, mycosis fungoides, myeloid and lymphocytic leukemia, neuroblastoma, non-Hodgkin's lymphoma, osteogenic sarcoma, ovarian carcinoma, pancreatic carcinoma, polycythemia vera, primary brain carcinoma, primary macroglobulinemia, prostatic carcinoma, renal cell carcinoma, rhabdomyosarcoma, skin cancer, small-cell lung carcinoma, soft-tissue sarcoma, squamous cell carcinoma, stomach carcinoma, testicular carcinoma, thyroid carcinoma, and Wilms' tumor. In one embodiment, the cancer is a solid tumor. In another embodiment, the cancer is selected from the group consisting of colon cancer, brain cancer, glioma, multiple myeloma, head and neck cancer hepatocellular cancer, melanoma, ovarian cancer, cervical cancer, renal cancer, and non-small cell lung cancer.

Animals which may be treated according to the present invention include all animals which may benefit from administration of compounds having Formula I. Such animals include humans, pets such as dogs and cats, and veterinary animals such as cows, pigs, sheep, goats and the like.

The term "non-N-oxide" as used herein refers to an amine compound that is not oxidized at the nitrogen atom. As an example, tegafur Mannich base is the non-N-oxide form of tegafur Mannich base N-oxide.

The term "non-Mannich base N-oxide" as used herein refers to a drug containing an acidic N—H group that has not been transformed to a Mannich base or to a Mannich base N-oxide. As an example, tegafur is the non-Mannich base N-oxide of tegafur Mannich base N-oxide.

The term "Mannich base N-Oxide" as used herein refers to the N-oxide of a Mannich base. The Mannich bases of the present invention may be prepared from the reaction between a secondary amine, an aldehyde and an NH—acidic site (e.g., amide, imide, sulfonamide, heterocyclic NH) on a drug molecule. An illustrative example of the preparation and N-oxidation of a Mannich base of an amide is shown in the following Scheme. According to this scheme, the Mannich base (7) is prepared from a reaction between a secondary amine, an aldehyde and an NH-acidic site (e.g., an amide, imide, sulfonamide, heterocycle NH, etc.) on a drug molecule. Following condensation, the Mannich base may be oxidized with, for example, m-chloroperoxybenzoic acid or ozone in chloroform or dichloromethane, to yield benzamide Mannich base N-oxide (8). Any dialkylamine, including cyclic amines, may be suitable. Thus, other dialkyl amines such as dimethylamine, piperidine, pyrrolidine or morpholine may be used as the secondary amine to obtain a Mannich base.

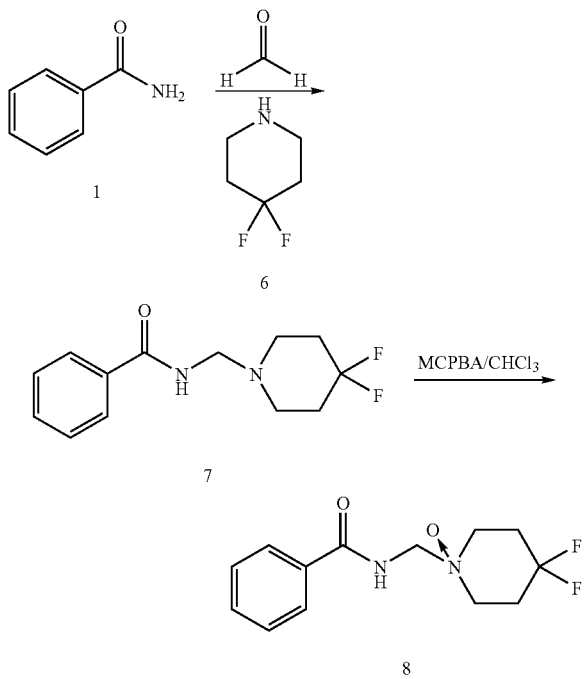

As a further example, the following scheme illustrates the synthesis of a Mannich base N-oxide prepared from benzamide and dimethylamine.

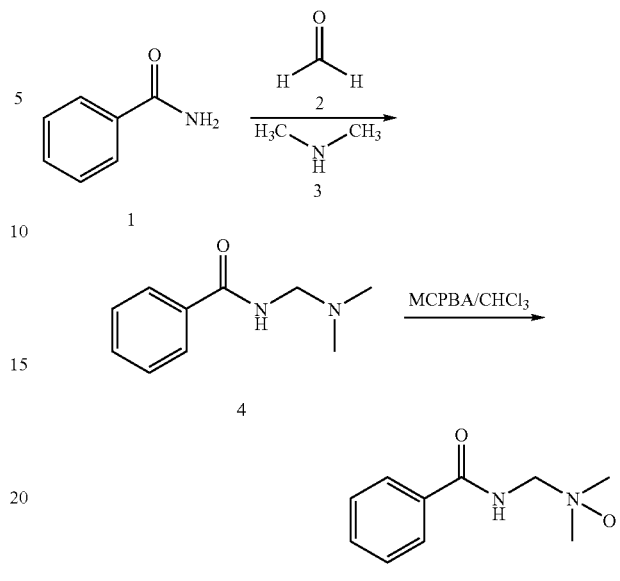

Mannich base N-oxides of certain drugs may themselves have biological activities and be suitable as a drug without the need for bioreduction of the N-oxide group. In other situations, the N-oxide may not be biologically active and its bioreduction to the Mannich base followed by hydrolysis of the Mannich base to the parent drug will activate the drug. As such, Mannich base N-oxide of a drug may be considered as a prodrug of the parent drug.

The chemical structure of the Mannich base N-oxides as herein depicted in the figures, schemes, and claims may or may not indicate a charge on the oxygen and nitrogen atoms of the N-oxide moiety. In the event that the chemical structure of the N-oxide does not indicate these atom charges, such is implied with the oxygen atom having a negative charge and the nitrogen atom having a positive charge.

As used herein, the term "prodrug" refers to an ester, a phosphate, an imine, a carbamate, an acetal or a ketal of a parent Mannich base N-oxide molecule. For example, an ester of a carboxylic acid containing Mannich base N-oxide of the present invention may be prepared by condensation with an alcohol, preferably a lower alkyl alcohol, more preferably a $C_{1-4}$ alkyl alcohol. Similarly, an ester of a hydroxy containing compound of the present invention may be prepared by condensation with a carboxylic or a dioic acid, preferably an alkyl carboxylic or dioic acid, more preferably a $C_{1-4}$ carboxylic acid or a $C_{3-6}$ dioic acid or anhydride thereof. Moreover, an imine of an amino containing compound of the present invention may be obtained by condensation of the amino group with a carbonyl group of an aldehyde or a ketone. Aldehydes and ketones suitable for condensation with amino containing compounds of the present invention include alkyl and aryl ketones and aldehydes, more preferably alkyl ketones and aldehydes, more preferably lower alkyl ketones and aldehydes, most preferably $C_{1-4}$ alkyl aldehydes and ketones. A carbamate of an amino containing compound of the present invention may be prepared by condensation of the amino group with, for example, benzyloxycarbonyl chloride. In addition, an acetal or ketal of an alcohol containing compound of the present invention may be obtained by condensation of the hydroxy group with chloromethyl methyl ether or chloromethyl ethyl ether.

Compounds of the present invention may further be phosphoribosylated to prepare prodrugs of the present invention. For example, prodrugs of the compounds of the present invention may be prepared by mono-, di- or tri-phosphorylating any hydroxy group present in any hexapyranose and/or hexafuranose substituent of the compounds of formula IV.

Such derivatives typically require biotransformation, either solvolytic or enzymatic, within the organism to release the carboxylic acid-containing compound, hydroxy-containing compound, or the amino-containing compound, with or without the N-oxide group.

Preferred monosaccharide is a hexapyranose or a hexafuranose selected from the group consisting of glucose, glycosamine, D-quinovopyranose, galactose, galactosamine, L-fucopyranose, L-rhamnopyranose, D-glucopyranuronic acid, D-galactoypranuronic acid, D-mannopyranuronic acid, D-iodopyranuronic acid, glucose, glycosamine, D-quinovopyranose, galactose, galactosamine, L-fucopyranose, L-rhamnopyranose, D-glucopyranuronic acid, D-galactoypranuronic acid, D-mannopyranuronic acid and D-iodopyranuronic acid.

As used herein, the terms "carbocycle" and heterocycle" include both saturated and unsaturated rings.

Optional substituents on heterocycle, carbocycle, aralkyl and alkylaryl include, but not limited to, hydroxy; =O (attached to a C, S or P atom); =S (attached to a C, S or P atom); alkyl; alkoxy; halo; amine, $SO_2NH_2$; $SO_3$; carboxy; aryl; araylalkyl; alkylcarbonyl; alkoxycarbonyl; alkoxyphenyl; cycloalkylalkoxy; mono- and di-(hydroxyalkyl)amine; mono- and dialkylamine; dialkylamine N-oxide, mono- and di-(halophenyl)amine; di-(halophenyl)amine N-oxide; phenylalkylamine; phenylalkylamine N-oxide; hydroxyphenyl; purinylamino substituted with an optionally substituted alkoxy group; indol-2-yl substituted with up to three substituents selected from the group consisting of hydroxy, alkoxy or alkylcabonyloxy; an optionally substituted 5-7 membered heterocyclic ring comprising one or two heteroatoms selected from the group consisting of N, S and O; and optionally substituted tetrahydrofuryl.

Optional substituents on tetrahydrofuryl include up to six substituents selected from the group consisting of hydrogen, alkyl, hydroxy, alkoxy, alkylcarbonyloxy; hydroxyalkyl; $OC(=O)R_{11}$ wherein $R_{11}$ is hydrogen, acyl, alkylcarboxy or alkyl; $OR_{12}$ where $R_{12}$ is hydrogen, acyl or a group of the formula:

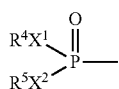

wherein $X^1$ and $X^2$ are independently O, NH, or S; $R^4$ is hydrogen, optionally substituted phenyl, optionally substituted phenyl, optionally substituted benzyl or optionally substituted naphthyl; $R^5$ is hydrogen, alkyl or alkenyl; $CH2OR_{13}$ wherein $R_{13}$ is hydrogen, acyl, alkylcarboxy, alkyl, aralkyl, a monosaccharide, or a group of the formula:

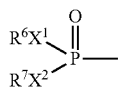

wherein $X^1$ and $X^2$ are independently O or S; $R^6$ is optionally substituted phenyl, optionally substituted benzyl or optionally substituted naphthyl; $R^7$ is alkyl or alkenyl; and $C(=O)—CR'R''H$ wherein R' is alkyl, alkoxy, or trifluoroacetamido, R'' is phenyl or phenylmethyl; or two substituents on adjacent carbon atoms form a double bond or a $—OC(=X^3)$O—$ group, wherein $X^3$ is S or O.

Optional substituents on alkyl groups include up to three substituents selected from the group consisting of optionally substituted aryl, carboxy, hydroxy, halo and amino.

Suitable optionally substituted aryloxycarbonyl groups include phenoxycarbonyl and naphthyloxycarbonyl, each of which is substituted with up to 3 substituents selected from the group consisting of halo, hydroxy and optionally substituted alkyl. Suitable optionally substituted heteroaryloxycarbonyl groups include pyridyloxycarbonyl, quinolinoxycarbonyl, purinyloxycarbonyl, each of which is substituted with up to 3 substituents selected from the group consisting of halo, hydroxy and optionally substituted alkyl.

Suitable optionally substituted aroyl groups include phenylcarboxy and naphthylcarboxy, each of which is substituted with up to 3 substituents selected from the group consisting of halo, hydroxy and optionally substituted alkyl. Suitable optionally substituted heteroaroyl groups include pyridylcarboxy, thiophenylcarboxy, pyrrolylcarboxy and quinolinylcarboxy, each of which is substituted with up to 3 substituents selected from the group consisting of halo, hydroxy and optionally substituted alkyl Useful secondary amines include, without limitation, dimethylamine, diethylamine, diisopropylamine, dibutylamine, di-sec-butylamine, di-tert-butylamine, piperidine, 4,4-difluoropiperidine, N-alkylpiperazine and morpholine The term "alkyl" as used herein refers to a saturated acyclic hydrocarbon radical, including from 1 to 10 carbon atoms, preferably from 1 to 8 carbon atoms, more preferably from 1 to about 4 carbon atoms. The term "lower alkyl" refers to acyclic hydrocarbon radicals containing from 1 to about 6 carbon atoms. Examples of suitable alkyl radicals include methyl, ethyl, propyl, butyl, isobutyl, pentyl, 2-methylbutyl, 3-methylbutyl, hexyl, heptyl, and octyl, and the like.

The term "alkoxy" means a straight, branched or cyclic hydrocarbon configuration and combinations thereof, including from 1 to 10 carbon atoms, preferably from 1 to 8 carbon atoms, more preferably from 1 to about 4 carbon atoms, and an oxygen atom at the point of attachment. Suitable alkoxy groups include methoxy, ethoxy, n-propoxy, isopropoxy, n-butoxy, iso-butoxy, sec-butoxy, tert-butoxy, cyclopropyloxy, cyclohexyloxy, and the like. "Lower alkoxy" refers to alkoxy groups having from 1 to 6 carbon atoms.

The term "alkenyl" refers to an unsaturated acyclic hydrocarbon radical including from about 2 to about 10 carbon atoms, preferably from about 2 to about 8 carbon atoms and more preferably 1 to about 6 carbon atoms. The alkenyl group may be dienyl and includes unsaturated alkenyl radicals appended or substituted on an otherwise alkyl group. Examples of alkenyl groups include vinyl, allyl (or 2-propenyl), 1-propenyl, iso-propenyl and 2-butenyl.

The term "cycloalkyl" as used herein refers to a saturated cyclic hydrocarbon radical. The term "lower cycloalkyl" refers to cyclic hydrocarbon radicals containing from about 3 to about 8 carbon atoms, preferably from about 3 to about 7 carbon atoms and more preferably 5 to about 7 carbon atoms. Examples of suitable cycloalkyl radicals include cyclopropyl, cyclobutyl, cyclopentyl, and cyclohexyl.

The term "acyl" or "alkanoyl" means an alkyl group attached to a carbonyl group.

The term "halogenoacyl" means an acyl group substituted with one or more halogen groups (e.g. F, Cl, Br and I groups), including trifluoroacetyl, pentafluoropropionyl and the like.

The term "aroyl" means an aryl-CO— group in which the aryl group is as described herein. Exemplary aroyl groups include benzoyl and 1- and 2-naphthoyl.

The term "aryl" as a group or part of a group denotes: (i) an optionally substituted monocyclic or multicyclic aromatic carbocyclic moiety of about 6 to about 14 carbon atoms, such as phenyl or naphthyl; or (ii) an optionally substituted partially saturated multicyclic aromatic carbocyclic moiety in which an aryl and a cycloalkyl, cycloalkenyl or a heterocyclic group are fused together to form a cyclic structure, such as a tetrahydronaphthyl, indenyl or indanyl ring. Aryl groups may be substituted with one or more including, for example, acyl, acylamino, alkoxy, alkyloxycarbonyl, alkylenedioxy, alkylsulfinyl, alkylsulfonyl, alkylthio, aroyl, aroylamino, aryl, arylalkenyl, arylalkynyl, arylalkyloxy, arylalkyloxycarbonyl, arylalkylthio, aryloxy, aryloxyalkyl, aryloxycarbonyl, arylsulfinyl, arylsulfonyl, arylthio, carboxy, cyano, halo, heteroaroyl, heteroaryl, heteroarylalkenyl, heteroarylalkynyl, heteroarylalkyloxy, heteroaroylamino, heteroaryloxy, heteroaryloxyalkyl, hydroxy, nitro and trifluoromethyl.

The term "heteroaroyl" means a heteroaryl-CO— group in which the heteroaryl group is as described herein. The term "heteroaryl" means an aromatic cyclic radical incorporating one or more heteroatoms and which may be fused with one or more saturated or unsaturated rings.

Useful heteroaryl groups include thienyl, benzo[b]thienyl, naphtho[2,3-b]thienyl, thianthrenyl, furyl, pyranyl, isobenzofuranyl, chromenyl, xanthenyl, phenoxanthenyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acridinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, 1,2-benzoisoxazol-3-yl, benzimidazolyl, 2-oxindolyl, and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide, pyrimidinyl N-oxide, and the like.

The term "N-oxide rearrangement product" as used herein refers to an O-substituted hyroxylamine species derived from the rearrangement of a Mannich base N-oxide. For example, the N-oxide rearrangement product of a compound of formula VIII is an O-substituted hydroxylamine of formula VIIIa; the N-oxide rearrangement product of a compound of formula IX is an O-substituted hydroxylamine of formula IXa:

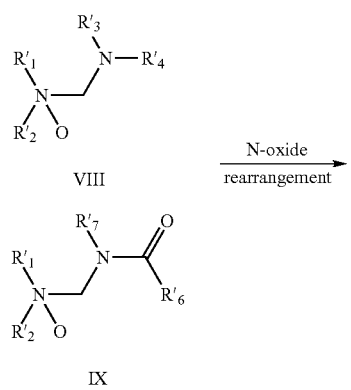

VIII

N-oxide rearrangement →

IX

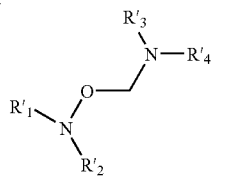

VIIIa

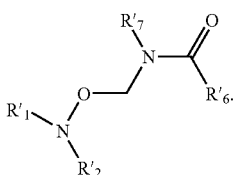

IXa

The term "residue of a nucleobase" as used herein refers to the residue of a base of a nucleic acid, e.g., thymine, uracil, adenine, cytosine, and guanine. The term "residue of a nucleobase-related compound" as used herein refers to the residue of base of a modified or substituted nucleic acid, e.g., 5-methylcytosine, 5-azaguanine, 5-azacytosine, and 5-fluorouracil. Modified or substituted nucleic acids are well known to those of ordinary skill in the art.

The term "pharmaceutical composition" as used herein, is to be understood as defining compositions of which the individual components or ingredients are themselves pharmaceutically acceptable, e.g., where oral administration is foreseen, acceptable for oral use; where topical administration is foreseen, topically acceptable; and where intravenous administration is foreseen, intravenously acceptable.

As used herein, the term "therapeutically effective amount" refers to that amount of the therapeutic agent sufficient to result in amelioration of one or more symptoms of a disorder, or prevent advancement of a disorder, or cause regression of the disorder. For example, with respect to the treatment of cancer, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

Compounds having Formula I can be provided as pharmaceutically acceptable salts. Examples of pharmaceutically acceptable salts (i.e., addition salts) include inorganic and organic acid addition salts such as hydrochloride, hydrobromide, phosphate, sulphate, citrate, lactate, tartrate, maleate, fumarate, mandelate, benzoate and oxalate; and inorganic and organic base addition salts with bases such as sodium hydroxy, Tris(hydroxymethyl)aminomethane (TRIS, tromethane) and N-methyl-glucamine. Although the salts typically have similar physiological properties compared to the free base, certain acid addition salts may demonstrate preferred physicochemical properties, e.g., enhanced solubility, improved stability. One particular pharmaceutically acceptable salt is derived from maleic acid, the salt being either a hydrogen maleate or a dimaleate salt.

Certain of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

In certain embodiments of the invention, compounds having Formula I are administered in combination with one or more other active agents (e.g., chemotherapeutic agents) or treatments. By way of non-limiting example, a patient may be treated for a hyperproliferative disorder, such as cancer, by the administration of a therapeutically effective amount of a compound having Formula I in combination with radiotherapy agent/treatment or the administration of a chemotherapeutic agent.

In other embodiments, compounds of the invention are administered in combination with agents, such as anti-angiogenic agents, that block inhibit or modulate tumor neovascularization. In particular embodiments, anti-angiogenesis agents can be any anti-angiogenesis agent which is used, has been used, or is known to be useful for the treatment of hyperproliferative disorders. Examples of anti-angiogenesis agents include bevacizumab (Avastin™), VEGF-TRAP, anti-VEGF-receptor antibodies, angiostatin, endostatin, batimastat, captopril, cartilage derived inhibitor, genistein, interleukin 12, lavendustin, medroxypregesterone acetate, recombinant human platelet factor 4, tecogalan, thrombospondin, TNP-470, VEGF antagonists, anti-VEGF monoclonal antibody, soluble VEGF-receptor chimaeric protein, antisense oligonucleotides, antisense oligodexoynucleotides, siRNAs, anti-VEGF aptamers, pigment epithelium derived factor, a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, pentosan polysulfate, a cyclooxygenase inhibitor, carboxyamidotriazole, combretastatin A-4, squalamine, 6-O-chloroacetyl-carbonyl)-fumagillol, thalidomide, troponin-1, indolinethiones, pyridopyrimidines, quinoazolines, phenyl-pyrrolo-pyrimidines, trastuzumab, calcium influx inhibitor (CAI), neomycin, squalamine, marimastat, prinomastat (AG-3340), metastat (COL-3) and cinnoline derivatives. Additional anti-angiogenic compounds that may be administered in combination with the compounds of the present invention are described in U.S. Pat. Nos. 5,192,744, 5,426,100, 5,733,876, 5,840,692, 5,854,205, 5,990,280, 5,994,292, 6,342,219, 6,342,221, 6,346,510, 6,479,512, 6,719,540, 6,797,488, 6,849,599, 6,869,952, 6,887,874, 6,958,340 and 6,979,682.

In certain embodiments, the compounds of the present invention are administered in combination with a vascular targeting agent (also known as vascular damaging agents). In one embodiment, the vascular targeting agent is for the treatment of malignant or non-malignant vascular proliferative disorders. In other embodiments, vascular targeting agents can be any vascular targeting agent which is used, has been used, or is known to be useful for the treatment of hyperproliferative disorders. Examples of vascular targeting agents that may be administered in combination with the compounds of the present invention include DMXAA 5,6-dimethylxanthenone-4-acetic acid, ZD6126, (5S)-5-(acetylamino)-9,10,11-trimethoxy-6,7-dihydro-5H-dibenzo[a,c]cyclohepten-3-yl dihydrogen phosphate, also known as N-acetylcolchinol-O-phosphate (see, for example, U.S. Pat. No. 6,906,048); functionalized stilbene derivatives such as combretastatin A4 and its prodrugs (see, e.g., U.S. Pat. Nos. 6,919,324 and 6,773,702); dioleoyltrimethyl-ammonium propane (DOTAP), N-[1-(2,3-dioleoyloxy)-propyl]-N,N,N-trimethylammonium chloride (DOTMA), dimethyldioctadecylammonium bromide (DDAB), 1,2-dimyristyloxypropyl-3-dimethylhydroxyethyl (DMRIE), dioleoyl-3-dimethylammonium propane (DODAP), N,N-dioleyl-N,N-dimethylammonium chloride (DODAC), or N-(1-(2,3-dioleyloxy)propyl)-N-(2-(sperminecarboxamido)ethyl)-N,N-dimethyl ammonium trifluoroacetate (DOSPA), or any other natural or synthetic cationic lipids, including, for example, dioleoylphosphatidyl-choline (DOPC), dipalmitoylphosphatidylcholine (DPPC), disteroylphosphatidylcholine (DSPC), dimyristoylphosphatidylcholine (DMPC), or 1,2-sn-dioleoylphosphatidylcholine (DOPE), or any other natural or synthetic electrostatically neutral lipids (see, for example, U.S. Pat. No. 6,680,068); vascular targeting agents which incorporate benzo[b]thiophene, indole, and benzofuran molecular skeletons such as those described in U.S. Pat. No. 6,593,374.

In other embodiments, the compounds of the present invention are administered in combination with a hypoxia-inducible factor 1 (HIF1) inhibitor. In one embodiment, the HIF1 inhibitor is for the treatment of malignant or non-malignant vascular proliferative disorders. In other embodiments, HIF1 inhibitors can be any HIF1 inhibitor which is used, has been used, or is known to be useful for the treatment of hyperproliferative disorders. Examples of HIF1 inhibitors suitable for use in combination with compounds of the present invention include topotecan, P13 kinase inhibitors; LY294002; rapamycin; histone deacetylase inhibitors such as [(E)-(1S,4S,10S,21R)-7-[(Z)-ethylidene]-4,21-diisopropyl-2-oxa-12,13-dithia-5,8,20,23-tetraazabicyclo-[8,7,6]-tricos-16-ene-3,6,9,19,22-pentanone (FR901228, depsipeptide); heat shock protein 90 (Hsp90) inhibitors such as geldanamycin, 17-allylamino-geldanamycin (17-AAG), and other geldanamycin analogs, and radicicol and radicicol derivatives such as KF58333; genistein; indanone; staurosporin; protein kinase-1 (MEK-1) inhibitors such as PD98059 (2'-amino-3'-methoxyflavone); PX-12 (1-methylpropyl 2-imidazolyl disulfide); pleurotin PX478; quinoxaline 1,4-dioxides; sodium butyrate (NaB); sodium nitropurruside (SNP) and other NO donors; microtubule inhibitors such as novobiocin, panzem (2-methoxyestradiol or 2-ME2), vincristines, taxanes, epothilones, discodermolide, and derivatives of any of the foregoing; coumarins; barbituric and thiobarbituric acid analogs; camptothecins; and YC-1. See U.S. Pat. No. 6,979,675.

In certain embodiments, the compounds of the present invention are administered in combination with an Hsp90 inhibitor. In one embodiment, the Hsp90 inhibitor is for the treatment of malignant or non-malignant vascular proliferative disorders. In other embodiments, Hsp90 inhibitors can be any Hsp90 inhibitor which is used, has been used, or is known to be useful for the treatment of hyperproliferative disorders. Examples of Hsp90 inhibitors that may be combined with the compounds of the present invention include geldanamycin, 17-allylamino-17-demethoxygeldanamycin, geldanamycin derivatives such as those described in U.S. Pat. No. 6,890,917, dexamethasone and benzoquinone ansamycins such as those described in U.S. Pat. No. 6,872,715. Additional Hsp90 inhibitors are disclosed in U.S. Pat. Nos. 6,613,780, 6,281,229 and 6,903,116.

In other embodiments, the compounds of the present invention are administered in combination with an inhibitor of tyrosine and/or serine/threonine kinases and tyrosine kinase receptors involved in cellular signaling. These include tyrosine kinase inhibitors of Src, Abl, Platelet Derived Growth Factor Receptors, Vascular Endothelial Growth Factor Receptors, c-Met, Fibroblast Growth Factor receptors, Epidermal Growth Factor Receptors, Insulin Growth Factor Receptors, mTOR, Flt-3, CSF-1 Receptor, AKT, Polo kinases, Aurora Kinases, STAT-3, PI-3 Kinase, Ras, Raf and Mitogen Activated Kinases, MEK, ERK. Examples of tyrosine kinase and serine/threonine kinase inhibitors include (but not limited to): AMG706, ZA6474, BAY 43-9006, Dasatinib, CEP-701, XL647, XL999, Lapatinb, MLN518/CT53518, PKC412, ST1571, AMN107, AEE 788, OSI-930, OSI-817, SU11248, AG-03736, GW-786034m, CEP-7055.

In other embodiments, the compounds of the present invention are administered in combination with HDAC inhibitors. Examples include (but not limited to) SAHA, MS-275, MGCD0103, LBH589, PXD101, FK228.

In other embodiments, the compounds of the present invention are administered in combination with proteasome inhibitors such as Velcade.

In other embodiments, the compounds of the present invention are administered in combination with pro-apoptotic agents such as TRAIL, anti-DR4/DR5 (TRA8) antibodies, IAP, Survivin or small molecules that stimulate caspase activation.

In other embodiments, the compounds of the present invention are administered in combination with inhibitors of cell cycle regulators such as CDK inhibitors.

"In combination" refers to the use of more than one treatment. The use of the term "in combination" does not restrict the order in which treatments are administered to a subject being treated for a hyperproliferative disorder. A first treatment can be administered prior to, concurrently with, after, or within any cycling regimen involving the administration of a second treatment to a subject with a hyperproliferative disorder. For example, the first treatment can be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before a treatment; or the first treatment can be administered 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after a second treatment. Such treatments include, for example, the administration of compounds having Formula I in combination with one or more chemotherapeutic agents or radiotherapeutic agents/treatments.

The term "chemotherapeutic agent," as used herein, is intended to refer to any chemotherapeutic agent known to those of skill in the art to be effective for the treatment, prevention or amelioration of hyperproliferative disorders such as cancer. Chemotherapeutic agents include, but are not limited to, small molecules, synthetic drugs, peptides, polypeptides, proteins, nucleic acids (e.g., DNA and RNA polynucleotides including, but not limited to, antisense nucleotide sequences, triple helices and nucleotide sequences encoding biologically active proteins, polypeptides or peptides), antibodies, synthetic or natural inorganic molecules, mimetic agents, and synthetic or natural organic molecules. Any agent which is known to be useful, or which has been used or is currently being used for the treatment or amelioration of a hyperproliferative disorder can be used in combination with a compound having Formula I. See, e.g., Hardman et al., eds., 2002, Goodman & Gilman's The Pharmacological Basis Of Therapeutics 10th Ed, Mc-Graw-Hill, New York, N.Y. for information regarding therapeutic agents which have been or are currently being used for the treatment or amelioration of a hyperproliferative disorder.

Particular chemotherapeutic agents useful in the methods and compositions of the invention include alkylating agents, antimetabolites, anti-mitotic agents, epipodophyllotoxins, antibiotics, hormones and hormone antagonists, enzymes, platinum coordination complexes, anthracenediones, substituted ureas, methylhydrazine derivatives, imidazotetrazine derivatives, cytoprotective agents, DNA topoisomerase inhibitors, biological response modifiers, retinoids, therapeutic antibodies, differentiating agents, immunomodulatory agents, angiogenesis inhibitors and anti-angiogenic agents.

Certain chemotherapeutic agents include, but are not limited to, abarelix, active vitamin D compound, aldesleukin, alemtuzumab, alitretinoin, allopurinol, altretamine, amifostine, anastrozole, arsenic trioxide, asparaginase, BCG live, bevaceizumab, bexarotene, bleomycin, bortezomib, busulfan, calusterone, camptothecin, capecitabine, carboplatin, carmustine, celecoxib, cetuximab, chlorambucil, cinacalcet, cisplatin, cladribine, cyclophosphamide, cytarabine, dacarbazine, dactinomycin, darbepoetin alfa, daunorubicin, denileukin diftitox, dexrazoxane, docetaxel, doxorubicin, dromostanolone, Elliott's B solution, epirubicin, epoetin alfa, estramustine, etoposide, exemestane, filgrastim, floxuridine, fludarabine, fluorouracil, fulvestrant, gemcitabine, gemtuzumab ozogamicin, gefitinib, goserelin, hydroxyurea, ibritumomab tiuxetan, idarubicin, ifosfamide, imatinib, interferon alfa-2a, interferon alfa-2b, irinotecan, letrozole, leucovorin, levamisole, lomustine, meclorethamine, megestrol, melphalan, mercaptopurine, mesna, methotrexate, methoxsalen, methylprednisolone, mitomycin C, mitotane, mitoxantrone, nandrolone, nofetumomab, oblimersen, oprelvekin, oxaliplatin, paclitaxel, pamidronate, pegademase, pegaspargase, pegfilgrastim, pemetrexed, pentostatin, pipobroman, plicamycin, polifeprosan, porfimer, procarbazine, quinacrine, rasburicase, rituximab, sargramostim, streptozocin, talc, tamoxifen, tarceva, temozolomide, teniposide, testolactone, thioguanine, thiotepa, topotecan, toremifene, tositumomab, trastuzumab, tretinoin, uracil mustard, valrubicin, vinblastine, vincristine, vinorelbine, and zoledronate.

Chemotherapeutic agents may be administered at doses that are recognized by those of skill in the art to be effective for the treatment of the hyperproliferative disorder. In certain embodiments, chemotherapeutic agents may be administered at doses lower than those used in the art due to the additive or synergistic effect of the compounds having Formula I.

Therapeutic agents useful in the methods and compositions of the invention include active vitamin D compound or mimics thereof, antineoplastic agents (e.g., actinomycin D, irinotecan, vincristine, vinorelbine, SN-38, azacitidine (5-azacytidine, 5AzaC), thalidomide vinblastine, methotrexate, azathioprine, fluorouracil, doxorubicin, mitomycin, docetaxel, paclitaxel), angiogenic inhibitors (e.g., VEGF-TRAP, angiostatin, endostatin, aptamer antogonist of VEGF, batimastat, captopril, cartilage derived inhibitor, genistein, interleukin 12, lavendustin, medroxypregesterone acetate, recombinant human platelet factor 4, tecogalan, thrombospondin and TNP-470), serine/threonine kinase inhibitors, tyrosine kinase inhibitors, HDAC inhibitors, Proteasome inhibitors, CDK inhibitors, HSP inhibitors, vasodilators (e.g., nitrates, calcium channel blockers), anticoagulants (e.g., heparin), anti-platelet agents (e.g., aspirin, blockers of IIb/IIIa receptors, clopidogrel), anti-thrombins (e.g., hirudin, iloprost), immunosuppressants (e.g., sirolimus, tranilast, dexamethasone, tacrolimus, everolimus, A24), collagen synthetase inhibitors (e.g., halofuginone, propyl hydroxylase, C-proteinase inhibitor, metalloproteinase inhibitor), anti-inflammatories (e.g., corticosteroids, non-steroidal anti-inflammatory drugs), 17β-estradiol, angiotensin converting enzyme inhibitors, colchicine, fibroblast growth factor antagonists, histamine antagonists, lovastatin, nitroprusside, phosphodiesterase inhibitors, prostaglandin inhibitors, suramin, serotonin blockers, thioprotease inhibitors, platelet-derived growth factor antagonists, nitric oxide, and angiopeptin. In one embodiment, the therapeutic agent is a taxane, e.g., paclitaxel or docetaxel.

In certain embodiments, patients are subjected to a hypoxia imaging technique prior to administration of the compositions comprising the compounds of the present invention. Examples of imaging techniques suitable for the determination of the presence of hypoxic tumor cells include computed tomography (CT), magnetic resonance imaging (MRI), single photon emission computer tomography (SPECT), and positron emission tomography (PET). As an illustration, PET imaging technique may be used to determine hypoxic tissue to blood ratio of a substance with increased retention in hypoxic tissue. An example of one such substance is [F-18] fluoromisonidazole (FMISO). For example, patients may be injected with 0.05-0.5 mCi/Kg of FMISO followed by PET imaging. Tissue to blood (T:B) FMISO ratio may be calculated using venous blood obtained during the emission part of the scan with a cutoff T:B ratio of, for example, 1.2 to signify hypoxia. Use of such visualization methods can advantageously be used to select a subset of patients that are particularly suitable for treatment with hypoxia activated antiproliferative compositions of the present invention.

In this embodiment, the invention is directed to a method of treating, preventing or ameliorating a hyperproliferative disease in an animal in need thereof, comprising determining whether said hyperproliferative disease is characterized by hypoxic tissue, and treating said animal with an effective amount of a compound of the invention.

The term "radiotherapeutic agent," as used herein, is intended to refer to any radiotherapeutic agent known to one of skill in the art to be effective to treat or ameliorate cancer, without limitation. For instance, the radiotherapeutic agent can be an agent such as those administered in brachytherapy or radionuclide therapy. Such methods can optionally further comprise the administration of one or more additional cancer therapies, such as, but not limited to, chemotherapies, surgery, and/or another radiotherapy.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of brachytherapy. The brachytherapy can be administered according to any schedule, dose, or method known to one of skill in the art to be effective in the treatment or amelioration of cancer, without limitation. In general, brachytherapy comprises insertion of radioactive sources into the body of a subject to be treated for cancer, preferably inside the tumor itself, such that the tumor is maximally exposed to the radioactive source, while preferably minimizing the exposure of healthy tissue.

In certain embodiments, the brachytherapy can be intracavitary brachytherapy. In other embodiments, the brachytherapy can be interstitial brachytherapy. Whether the brachytherapy is intracavitary brachytherapy or interstitial brachytherapy, the brachytherapy can be administered at a high dose rate, a continuous low dose rate, or a pulsed dose rate. For example, and not by way of limitation, a high dose rate brachytherapy regimen can be a dose of 60 Gy administered in ten fractions over six days, while a continuous low dose rate brachytherapy regimen can be a total dose of about 65 Gy, administered continuously at about 40 to 50 cGy per hour. Other examples of high, continuous low, and pulsed dose rate brachytherapy are well known in the art. See, e.g., Mazeron et al., *Sem. Rad. Onc.* 12:95-108 (2002).

Representative radioisotopes that can be administered in any of the above-described brachytherapies include, but are not limited to, phosphorus 32, cobalt 60, palladium 103, ruthenium 106, iodine 125, cesium 137, iridium 192, xenon 133, radium 226, californium 252, or gold 198. Other radioisotopes may be selected for administration in brachytherapy according to the desirable physical properties of such a radioisotope. One of skill in the art will readily recognize that many properties will affect a radioisotope's suitability for use in brachytherapy, including, but not limited to, the radioisotope's half-life, the degree to which emitted radiation penetrates surrounding tissue, the energy of emitted radiation, the ease or difficulty of adequately shielding the radioisotope, the availability of the radioisotope, and the ease or difficulty of altering the shape of the radioisotope prior to administration.

Additional methods of administering and apparatuses and compositions useful for brachytherapy are described in U.S. Pat. Nos. 6,319,189, 6,179,766, 6,168,777, 6,149,889, and 5,611,767.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of a radionuclide. The radionuclide therapy can be administered according to any schedule, dose, or method known to one of skill in the art to be effective in the treatment or amelioration of cancer, without limitation. In general, radionuclide therapy comprises systemic administration of a radioisotope that preferentially accumulates in or binds to the surface of cancerous cells. The preferential accumulation of the radionuclide can be mediated by a number of mechanisms, including, but not limited to, incorporation of the radionuclide into rapidly proliferating cells, specific accumulation of the radionuclide by the cancerous tissue without special targeting (e.g., iodine 131 accumulation in thyroid cancer), or conjugation of the radionuclide to a biomolecule specific for a neoplasm.

Representative radioisotopes that can be administered in radionuclide therapy include, but are not limited to, phosphorus 32, yttrium 90, dysprosium 165, indium 111, strontium 89, samarium 153, rhenium 186, iodine 131, iodine 125, lutetium 177, and bismuth 213. While all of these radioisotopes may be linked to a biomolecule providing specificity of targeting, iodine 131, indium 111, phosphorus 32, samarium 153, and rhenium 186 may be administered systemically without such conjugation. One of skill in the art may select a specific biomolecule for use in targeting a particular neoplasm for radionuclide therapy based upon the cell-surface molecules present on that neoplasm. For example, hepatomas may be specifically targeted by an antibody specific for ferritin, which is frequently over-expressed in such tumors. Examples of antibody-targeted radioisotopes for the treatment of cancer include ZEVALIN (ibritumomab tiuxetan) and BEXXAR (tositumomab), both of which comprise an antibody specific for the B cell antigen CD20 and are used for the treatment of non-Hodgkin lymphoma.

Other examples of biomolecules providing specificity for particular cell are reviewed in an article by Thomas, *Cancer Biother. Radiopharm.* 17:71-82 (2002), which is incorporated herein by reference in its entirety. Furthermore, methods of administering and compositions useful for radionuclide therapy may be found in U.S. Pat. Nos. 6,426,400, 6,358,194, 5,766,571, and 5,563,250.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of external-beam radiation therapy. The external-beam radiation therapy can be administered according to any schedule, dose, or method known to one of skill in the art to be effective in the treatment or amelioration of cancer, without limitation. In general, external-beam radiation therapy comprises irradiating a defined volume within a subject with a high energy beam, thereby causing cell death within that volume. The irradiated volume preferably contains the entire cancer to be treated, and preferably contains as little healthy tissue as possible.

In certain embodiments, the external-beam radiation therapy can be three-dimensional conformal radiotherapy. In other embodiments, the external-beam radiation therapy can be continuous hyperfractionated radiotherapy. In still other embodiments, the external-beam radiation therapy can be intensity-modulated radiotherapy. In yet other embodiments, the external-beam radiation therapy can be helical tomotherapy. In still other embodiments, the external-beam radiation therapy can be three-dimensional conformal radiotherapy with dose escalation. In yet other embodiments, the external-beam radiation therapy can be stereotactic radiotherapy, including, but not limited to, single fraction stereotactic radiotherapy, fractionated stereotactic radiotherapy, and fractionated stereotactically guided conformal radiotherapy.

The external-beam radiation therapy can be generated or manipulated by any means known to one of skill in the art. For example, the photon beam used in external-beam radiation therapy can be shaped by a multileaf collimator. Other examples of suitable devices for generating a photon beam for use in external-beam radiation therapy include a gamma knife and a linac-based stereotactic apparatus. In certain embodiments, administration of the external-beam radiation therapy is controlled by a computer according to a three-dimensional model of the patient in the treatment position. Such a model can be generated, for example, by computed tomography (CT), magnetic resonance imaging (MRI), single photon emission computer tomography (SPECT), and positron emission tomography (PET). Use of such visualization methods can advantageously minimize the volume of healthy tissue treated, thereby allowing higher total doses of radiation to be administered to the patient.

In addition, healthy tissues can optionally be protected from the effects of the external-beam radiation therapy by placing blocking devices such as, e.g., lead shields, in locations where such protection is needed. Alternatively or additionally, metal reflecting shields can optionally be located to reflect the photon beam in order to concentrate the radiation on the cancerous tissue to be treated and protect healthy tissue. Placement of either shield is well within the knowledge of one of skill in the art.

Methods of administering and apparatuses and compositions useful for external-beam radiation therapy can be found in U.S. Pat. Nos. 6,449,336, 6,398,710, 6,393,096, 6,335,961, 6,307,914, 6,256,591, 6,245,005, 6,038,283, 6,001,054, 5,802,136, 5,596,619, and 5,528,652.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of thermotherapy. The thermotherapy can be administered according to any schedule, dose, or method known to one of skill in the art to be effective in the treatment or amelioration of cancer, without limitation. In certain embodiments, the thermotherapy can be cryoablation therapy. In other embodiments, the thermotherapy can be hyperthermic therapy. In still other embodiments, the thermotherapy can be a therapy that elevates the temperature of the tumor higher than in hyperthermic therapy.

Cryoablation therapy involves freezing of a neoplastic mass, leading to deposition of intra- and extra-cellular ice crystals; disruption of cellular membranes, proteins, and organelles; and induction of a hyperosmotic environment, thereby causing cell death. Cryoablation can be performed in one, two, or more freeze-thaw cycles, and further the periods of freezing and thawing can be adjusted for maximum tumor cell death by one of skill in the art. One exemplary device that can be used in cryoablation is a cryoprobe incorporating vacuum-insulated liquid nitrogen. See, e.g., Murphy et al., *Sem. Urol. Oncol.* 19:133-140 (2001). However, any device that can achieve a local temperature of about −180° C. to about −195° C. can be used in cryoablation therapy. Methods for and apparatuses useful in cryoablation therapy are described in U.S. Pat. Nos. 6,383,181, 6,383,180, 5,993,444, 5,654,279, 5,437,673, and 5,147,355.

Hyperthermic therapy typically involves elevating the temperature of a neoplastic mass to a range from about 42° C. to about 44° C. The temperature of the cancer may be further elevated above this range; however, such temperatures can increase injury to surrounding healthy tissue while not causing increased cell death within the tumor to be treated. The tumor may be heated in hyperthermic therapy by any means known to one of skill in the art without limitation. For example, and not by way of limitation, the tumor may be heated by microwaves, high intensity focused ultrasound, ferromagnetic thermoseeds, localized current fields, infrared radiation, wet or dry radiofrequency ablation, laser photocoagulation, laser interstitial thermic therapy, and electrocautery. Microwaves and radiowaves can be generated by waveguide applicators, horn, spiral, current sheet, and compact applicators.

Other methods of and apparatuses and compositions for raising the temperature of a tumor are reviewed in an article by Wust et al., Lancet Oncol. 3:487-97 (2002), and described in U.S. Pat. Nos. 6,470,217, 6,379,347, 6,165,440, 6,163,726, 6,099,554, 6,009,351, 5,776,175, 5,707,401, 5,658,234, 5,620,479, 5,549,639, and 5,523,058.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of radiosurgery. The radiosurgery can be administered according to any schedule, dose, or method known to one of skill in the art to be effective in the treatment or amelioration of cancer, without limitation. In general, radiosurgery comprises exposing a defined volume within a subject to a manually directed radioactive source, thereby causing cell death within that volume. The irradiated volume preferably contains the entire cancer to be treated, and preferably contains as little healthy tissue as possible. Typically, the tissue to be treated is first exposed using conventional surgical techniques, then the radioactive source is manually directed to that area by a surgeon. Alternatively, the radioactive source can be placed near the tissue to be irradiated using, for example, a laparoscope. Methods and apparatuses useful for radiosurgery are further described in Valentini et al., Eur. J. Surg. Oncol. 28:180-185 (2002) and in U.S. Pat. Nos. 6,421,416, 6,248,056, and 5,547,454.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of charged-particle radiotherapy. The charged-particle radiotherapy can be administered according to any schedule, dose, or method known to one of skill in the art to be effective in the treatment or amelioration of cancer, without limitation. In certain embodiments, the charged-particle radiotherapy can be proton beam radiotherapy. In other embodiments, the charged-particle radiotherapy can be helium ion radiotherapy. In general, charged-particle radiotherapy comprises irradiating a defined volume within a subject with a charged-particle beam, thereby causing cellular death within that volume. The irradiated volume preferably contains the entire cancer to be treated, and preferably contains as little healthy tissue as possible. A method for administering charged-particle radiotherapy is described in U.S. Pat. No. 5,668,371.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of neutron radiotherapy. The neutron radiotherapy can be administered according to any schedule, dose, or method known to one of skill in the art to be effective in the treatment or amelioration of cancer, without limitation.

In certain embodiments, the neutron radiotherapy can be a neutron capture therapy. In such embodiments, a compound that emits radiation when bombarded with neutrons and preferentially accumulates in a neoplastic mass is administered to a subject. Subsequently, the tumor is irradiated with a low energy neutron beam, activating the compound and causing it to emit decay products that kill the cancerous cells. Such compounds are typically boron containing compounds, but any compound that has a significantly larger neutron capture cross-section than common body constituents can be used. The neutrons administered in such therapies are typically relatively low energy neutrons having energies at or below about 0.5 eV. The compound to be activated can be caused to preferentially accumulate in the target tissue according to any of the methods useful for targeting of radionuclides, as described below, or in the methods described in Laramore, Semin. Oncol. 24:672-685 (1997) and in U.S. Pat. Nos. 6,400,796, 5,877,165, 5,872,107, and 5,653,957.

In other embodiments, the neutron radiotherapy can be a fast neutron radiotherapy. In general, fast neutron radiotherapy comprises irradiating a defined volume within a subject with a neutron beam, thereby causing cellular death within that volume. The irradiated volume preferably contains the entire cancer to be treated, and preferably contains as little healthy tissue as possible. Generally, high energy neutrons are administered in such therapies, with energies in the range of about 10 to about 100 million eV. Optionally, fast neutron radiotherapy can be combined with charged-particle radiotherapy in the administration of mixed proton-neutron radiotherapy.

In certain embodiments involving radiotherapeutic agents or treatments, the present invention relates to a method for treating cancer comprising the administration of 5-FU analog or prodrug N-oxide having Formula I, in combination with a treatment comprising a therapeutically effective dose of photodynamic therapy. The photodynamic therapy can be administered according to any schedule, dose, or method known to one of skill in the art to be effective in the treatment or amelioration of cancer, without limitation. In general, photodynamic therapy comprises administering a photosensitizing agent that preferentially accumulates in a neoplastic mass and sensitizes the neoplasm to light, then exposing the tumor to light of an appropriate wavelength. Upon such exposure, the photosensitizing agent catalyzes the production of a cytotoxic agent, such as, e.g., singlet oxygen, which kills the cancerous cells.

Representative photosensitizing agents that may be used in photodynamic therapy include, but are not limited to, porphyrins such as porfimer sodium, 5-aminolaevulanic acid and verteporfin; chlorins such as temoporfin; texaphyrins such as lutetium texephyrin; purpurins such as tin etiopurpurin; phthalocyanines; and titanium dioxide. The wavelength of light used to activate the photosensitizing agent can be selected according to several factors, including the depth of the tumor beneath the skin and the absorption spectrum of the photosensitizing agent administered. The period of light exposure may also vary according to the efficiency of the absorption of light by the photosensitizing agent and the efficiency of the transfer of energy to the cytotoxic agent. Such determinations are well within the ordinary skill of one in the art.

Methods of administering and apparatuses and compositions useful for photodynamic therapy are disclosed in Hopper, Lancet Oncol. 1:212-219 (2000) and U.S. Pat. Nos. 6,283,957, 6,071,908, 6,011,563, 5,855,595, 5,716,595, and 5,707,401.

It will be appreciated that both the particular radiation dose to be utilized in treating a hyperproliferative disorder and the method of administration will depend on a variety of factors. Thus, the dosages of radiation that can be used according to the methods of the present invention are determined by the particular requirements of each situation. The dosage will depend on such factors as the size of the tumor, the location of the tumor, the age and sex of the patient, the frequency of the dosage, the presence of other tumors, possible metastases and the like. Those skilled in the art of radiotherapy can readily ascertain the dosage and the method of administration for any particular tumor by reference to Hall, E. J., Radiobiology for the Radiologist, 5th edition, Lippincott Williams & Wilkins Publishers, Philadelphia, Pa., 2000; Gunderson, L. L. and Tepper J. E., eds., Clinical Radiation Oncology, Churchill Livingstone, London, England, 2000; and Grosch, D. S., Biological Effects of Radiation, 2nd edition, Academic Press, San Francisco, Calif., 1980. In certain embodiments, radiotherapeutic agents and treatments may be administered at doses lower than those known in the art due to the additive or synergistic effect of the compound having Formula I.

Compositions in accordance with the present invention may be employed for administration in any appropriate manner, e.g., oral or buccal administration, e.g., in unit dosage form, for example in the form of a tablet, in a solution, in hard or soft encapsulated form including gelatin encapsulated form, sachet, or lozenge. Compositions may also be administered parenterally or topically, e.g., for application to the skin, for example in the form of a cream, paste, lotion, gel, ointment, poultice, cataplasm, plaster, dermal patch or the like, or for ophthalmic application, for example in the form of an eye-drop, -lotion or -gel formulation. Readily flowable forms, for example solutions, emulsions and suspensions, may also be employed e.g., for intralesional injection, or may be administered rectally, e.g., as an enema or suppository, or intranasal administration, e.g., as a nasal spray or aerosol. Microcrystalline powders may be formulated for inhalation, e.g., delivery to the nose, sinus, throat or lungs. Transdermal compositions/devices and pessaries may also be employed for delivery of the compounds of the invention. The compositions may additionally contain agents that enhance the delivery of the compounds having Formula I (or other active agents), e.g., liposomes, polymers or co-polymers (e.g., branched chain polymers). Preferred dosage forms of the present invention include oral dosage forms and intravenous dosage forms.

Intravenous forms include, but are not limited to, bolus and drip injections. In particular embodiments, the intravenous dosage forms are sterile or capable of being sterilized prior to administration to a subject since they typically bypass the subject's natural defenses against contaminants. Examples of intravenous dosage forms include, but are not limited to, Water for Injection USP; aqueous vehicles including, but not limited to, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol and polypropylene glycol; and non-aqueous vehicles including, but not limited to, corn oil, cottonseed oil, peanut oil, sesame oil, ethyl oleate, isopropyl myristate and benzyl benzoate.

The pharmaceutical compositions of the present invention may further comprise one or more additives. Additives that are well known in the art include, e.g., detackifiers, antifoaming agents, buffering agents, antioxidants (e.g., ascorbic acid, ascorbyl palmitate, sodium ascorbate, butylated hydroxyanisole (BHA), butylated hydroxytoluene (BHT), propyl gallate, malic acid, fumaric acid, potassium metabisulfite, sodium bisulfite, sodium metabisulfite, and tocopherols, e.g., a-tocopherol (vitamin E)), preservatives, chelating agents, viscomodulators, tonicifiers, flavorants, colorants, odorants, opacifiers, suspending agents, binders, fillers, plasticizers, lubricants, and mixtures thereof. The amounts of such additives can be readily determined by one skilled in the art, according to the particular properties desired, and can be formulated such that compounds having Formula I are stable, e.g., not reduced by antioxidant additives.

The additive may also comprise a thickening agent. Suitable thickening agents may be of those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products.

Such thickening agents as described above may be included, e.g., to provide a sustained release effect. However, where oral administration is intended, the use of thickening agents may not be required. Use of thickening agents is, on the other hand, indicated, e.g., where topical application is foreseen.

In one embodiment of the invention, compounds having Formula I are formulated as described, for example, in U.S. Pat. No. 6,653,319.

Although the dosage of the compound having Formula I will vary according to the activity and/or toxicity of the particular compound, the condition being treated, and the physical form of the pharmaceutical composition being employed for administration, it may be stated by way of guidance that a dosage selected in the range from 0.1 to 20 mg/kg of body weight per day will often be suitable, although higher dosages, such as 0.1 to 50 mg/kg of body weight per day may be useful. Those of ordinary skill in the art are familiar with methods for determining the appropriate dosage. Methods for assessing the toxicity, activity and/or selectivity of the compounds having Formula I may be carried out using any of the methods known in the art, including the antiproliferative activity test.

In certain instances, the dosage of the compounds having Formula I will be lower, e.g., when used in combination with at least a second hyperproliferative disorder treatment, and may vary according to the activity and/or toxicity of the particular compound, the condition being treated, and the physical form of the pharmaceutical composition being employed for administration.

When the composition of the present invention is formulated in unit dosage form, the compound having Formula I will preferably be present in an amount of between 0.01 and 2000 mg per unit dose. More preferably, the amount of compound having Formula I per unit dose will be about 0.01, 0.05, 0.1, 0.5, 1, 5, 10, 20, 30, 40, 50, 60, 70, 80, 90, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, or 2000 mg or any amount therein.

When the unit dosage form of the composition is a capsule, the total quantity of ingredients present in the capsule is preferably about 10-1000 µL. More preferably, the total quantity of ingredients present in the capsule is about 100-300 µL. In another embodiment, the total quantity of ingredients present in the capsule is preferably about 10-1500 mg, preferably about 100-1000 mg.

The relative proportion of ingredients in the compositions of the invention will, of course, vary considerably depending on the particular type of composition concerned. The relative proportions will also vary depending on the particular function of ingredients in the composition. The relative proportions will also vary depending on the particular ingredients employed and the desired physical characteristics of the product composition, e.g., in the case of a composition for topical use, whether this is to be a free flowing liquid or a paste. Determination of workable proportions in any particular instance will generally be within the capability of a person of ordinary skill in the art. All indicated proportions and relative weight ranges described below are accordingly to be understood as being indicative individually inventive teachings only and not as limiting the invention in its broadest aspect.

The amount of compound having Formula I in compositions of the invention will of course vary, e.g., depending on the intended route of administration and to what extent other components are present. In general, however, the compound having Formula I will suitably be present in an amount of from about 0.005% to 20% by weight based upon the total weight of the composition. In certain embodiments, the compound having Formula I is present in an amount of from about 0.01% to 15% by weight based upon the total weight of the composition.

In addition to the foregoing, the present invention also provides a process for the production of a pharmaceutical composition as hereinbefore defined, which process comprises bringing the individual components thereof into intimate admixture and, when required, compounding the obtained composition in unit dosage form, for example filling said composition into tablets, gelatin, e.g., soft or hard gelatin, capsules, or non-gelatin capsules.

The starting materials of the Mannich base N-oxides of the present invention are known and some of them are described, for example, in U.S. Pat. Nos. 3,322,747, 3,948,897, 4,757,139, 5,032,680, 5,530,003, 5,614,505, 5,808,049 and 6,702,705. Examples of other starting materials for preparing Mannich base N-oxides of the present invention include capecitabine (known as CAP, which is a prodrug of 5-FU; see for example, Malet-Martino, M. et al., *The Oncologist*, 7:288-323 (2002)), cytarbine (known as Arc-a and sold under brand names Cytosar-U®, DepoCyst®), 5-iodo-2'-deoxycytidine (5-IDC, see, for example, Koch, S. A. M. and Sloan, K. B. *Phram. Res.* 4:317 (1987)), cytidine, azacitidine (5-azacytidine, 5AzaC, Vida™), 5-aza-2'-deoxycytidine, 2-pyrimidone-1-β-D-ribo side (zebularine), carmustine, tetracycline (Achromycin®[DSC], Brodspec®, EmTet®), chlorotetracycline (Aureomycin Soluble Powder Concentrate®), oxytetracycline, minocycline, doxycycline, 3-[1,3-Dihydro-3-(hydroxyimino)-2H-indol-2-ylidene]-1,3-dihydro-2H-indol-2-one (indirubin-3'-oxime), indirubin-5-sulfonic acid, 5-chloroindirubin, Tryprostatin A, Tryprostatin B, 4-(3-hydroxyphenyl)-6-methyl-2-thioxo-1,2,3,4-tetrahydro-4H-pyrimidin-5-carboxylic acid ethyl ester (Monastrol), 4-(4-methoxyphenyl)-6-methyl-2-thioxo-1,2,3,4-tetrahydro-4H-pyrimidin-5-carboxylic acid ethyl ester (DHP2), Paclitaxel, Nonataxel, 7,12-dihydroindolo[3,2-d][1]benzazepin-6(5H)-one (Paullone) and 9-Bromo-7,12-dihydroindolo[3,2-d][1]benzazepin-6(5H)-one (Kenpaullone). It will be recognized that nucleosides (e.g., deoxycytidine) may be mono-, di- or triphosphorylated forming nucleotide mono-, di- or tri-phosphate. Thus, the starting materials for the Mannich base N-oxides of the present invention also include all nucleotide mono-, di- and tri-phosphates of nucleosides disclosed in this invention.

For example, Mannich base N-oxides of an N—H containing drug may be prepared by reacting the drug with formaldehyde in the presence of a secondary amine followed by oxidation of the resulting tertiary amine. Such Mannich base N-oxides may form a family of hypoxia activated prodrugs of the N—H containing drugs and/or they may have biological activity. As an illustration, a Mannich base N-oxide of an N—H containing compound, such as a peptide, a carboxamide, a phosphoramidate, a phosphonamidate, a sulfonamide, a lactam or an imide may be prepared according to the following scheme:

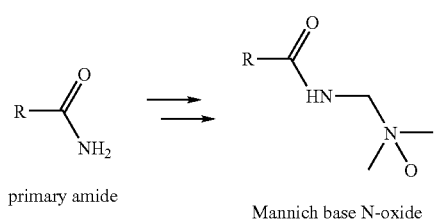

primary amide → Mannich base N-oxide wherein RCONH is a residue derived from a biologically active drug such as a carboxamide (e.g., a peptide). Specific examples of N—H containing drugs that may be suitable for the present invention include TNP-470, CAP, enauracil, CDHP, capecitabine, cytarabine, 5-iodo-2'-deoxycytidine, cytidine, 5-azacitidine, 5-aza-2'-deoxycytidine, 2-pyrimidone-1-β-D-riboside, tetracycline, chlorotetracycline, oxytetracycline, minocycline, doxycycline, indirubin-3'-oxime, indirubin-5-sulfonic acid, 5-chloroindirubin, Tryprostatin A, Tryprostatin B, Monastrol, DHP2, Paclitaxel, Nonataxel, Paullone and Kenpaullone.

Similarly, a sulfonamide Mannich base N-oxide may prepared as shown in the scheme below:

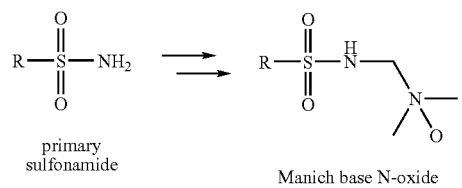

primary sulfonamide → Manich base N-oxide

A phosphoramidate Mannich base N-oxide may be prepared as shown in the scheme below:

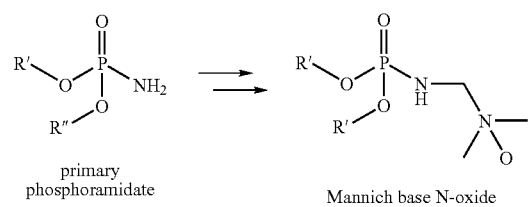

primary phosphoramidate → Mannich base N-oxide

Mannich base N-oxides of phosphoramidates, especially nucleoside phosphoramidates, may find utility in pharmaceutical applications for a number of reasons, e.g., Mannich base N-oxide derivatization may facilitate nucleoside phosphoramidate uptake in the gastrointestinal track and improve oral bioavailability of the parent nucleoside phosphoramidate. Also, a Mannich base N-oxide of a nucleoside phosphoramidate may be converted to the parent phosphoramidate selectively in a hypoxic tumor, where unmasking triggers phosphoramidase hydrolysis to the desired monophosphate within the tumor. See Hecker, *J. Med. Chem.* 51:2328 (2008); Meier et al, *Nucleic Acids Symp. Ser. No.* 52 83 (2008).

An example of a drug containing an N—H group attached to a —N═C— group that may be converted to a Mannich base N-oxide is Ara-C.

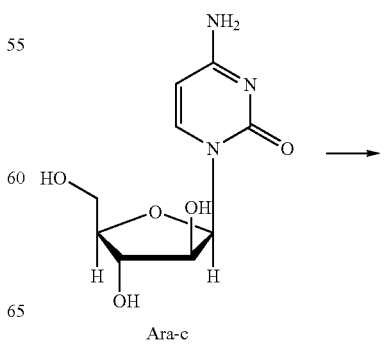

Ara-c

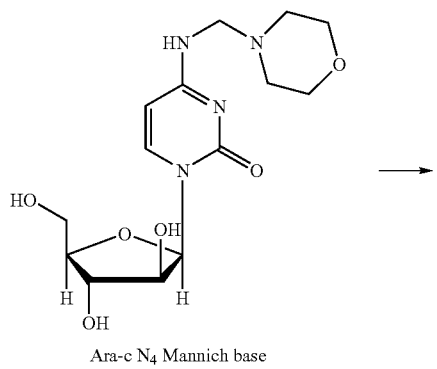

Ara-c N4 Mannich base

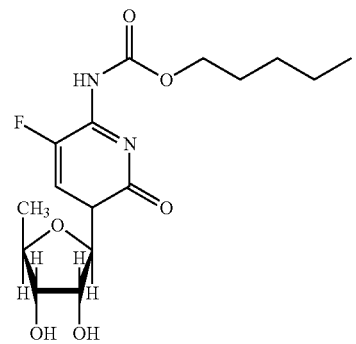

CAP

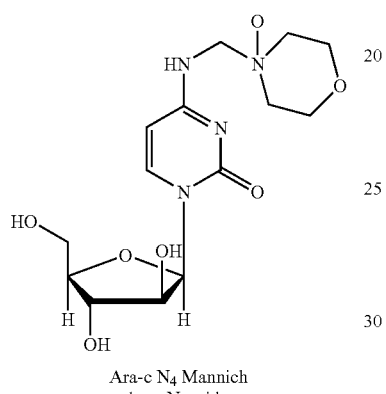

Ara-c N4 Mannich base N-oxide

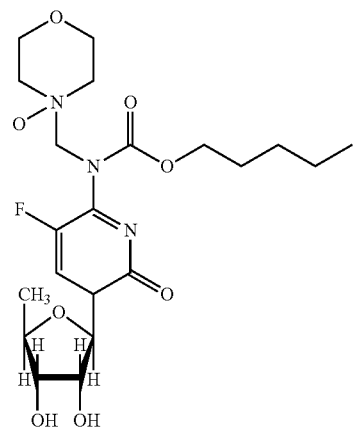

CAP Mannich base N-oxide

An example of an imide that may be suitable for formation of a Mannich base N-oxide is the antiangiogenic compound TNP-470.

Mannich base N-oxides of eniluracil and gimestat (CDHP) may also be prepared as shown below:

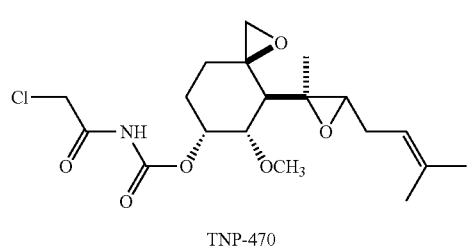

TNP-470

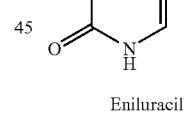

Eniluracil

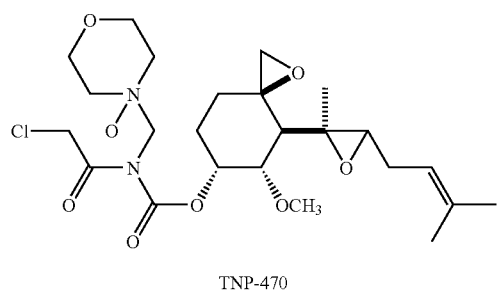

TNP-470 Mannich base N-oxide

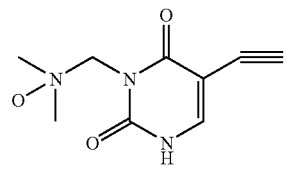

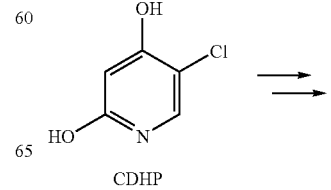

CDHP

In addition, capecitabine (CAP) may be converted to its corresponding Mannich base N-oxide as shown below:

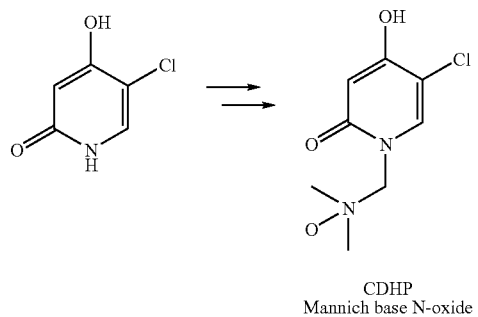

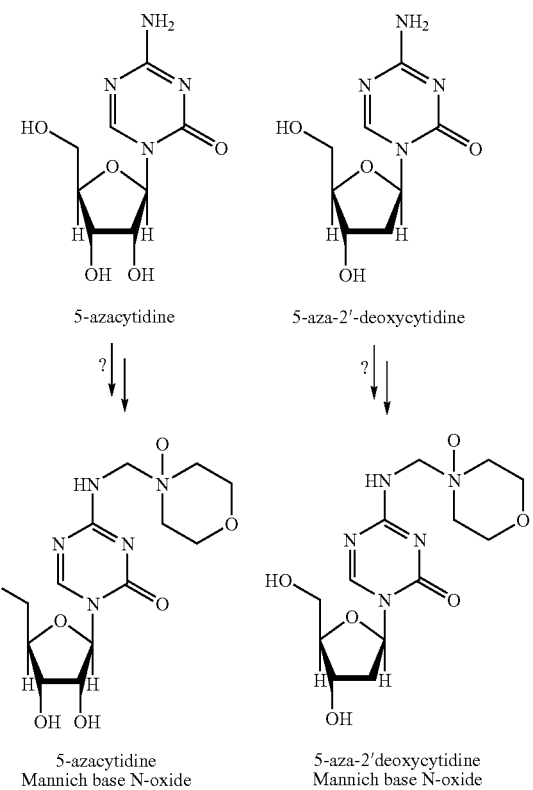

The Mannich base N-oxide of a drug containing an acidic N—H may be prepared using any suitable secondary amine. For example, the Mannich bases of 5-iodo-2'-deoxycytidine prepared with piperidine or morpholine are schematically shown below for 5-iodo-2'-deoxycytidine:

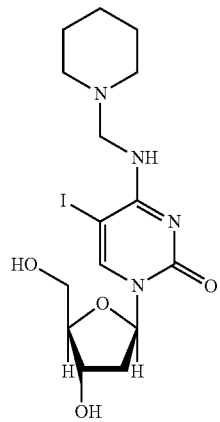

N$^4$-(1″-piperdinyl)methyl-5-iodo-2'-deoxycytidine (a N$^4$-piperidinyl Mannich base of 5-iodo-2'-deoxycytidine)

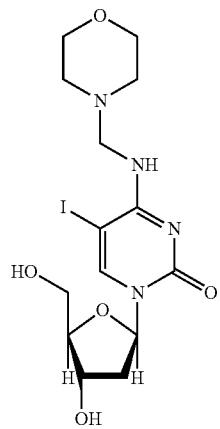

N$^4$-(1″-morpholinyl)methyl-5-iodo-2'-deoxycytidine (a N$^4$-morpholinyl Mannich base of 5-iodo-2'-deoxycytidine)

As an additional example, the Mannich base N-oxides of 5-azacytidine and 5-aza-2'-deoxycytidine prepared with morpholine are shown below:

The group —NR′$_3$R′$_4$ of formula I may be derived from a phosphoramidate-containing drug. For example, Mannich base N-oxide (MBNO) derivativation of cytarbine, decitabine, and 5-azacytidine phosphramidates is shown below:

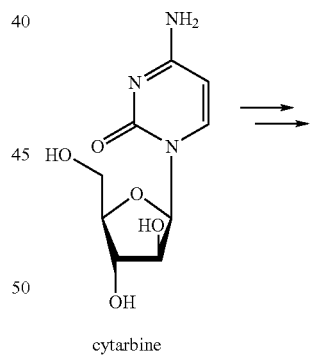

cytarbine

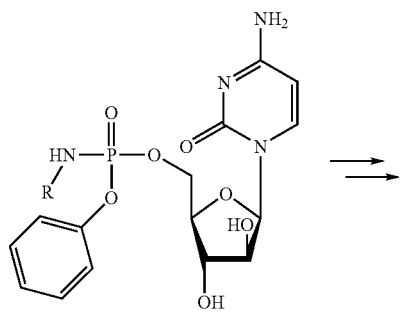

cytarbine phosphoramidate

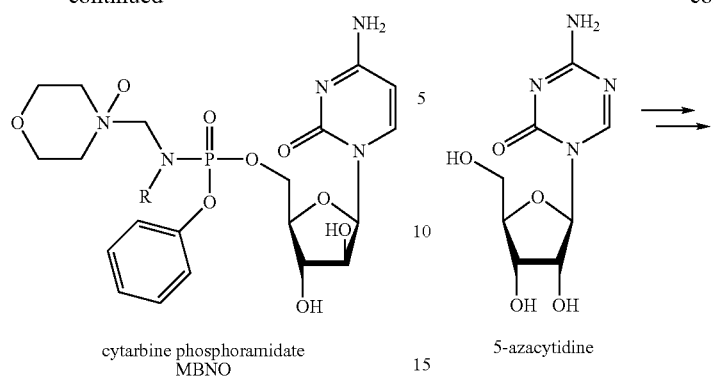
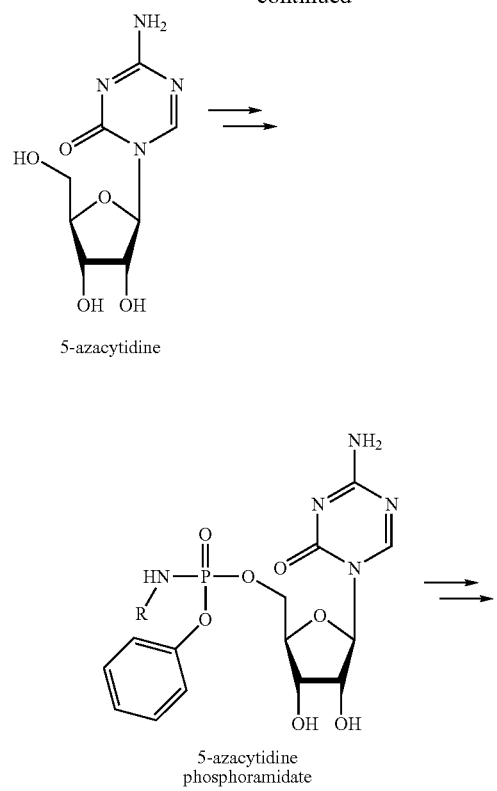
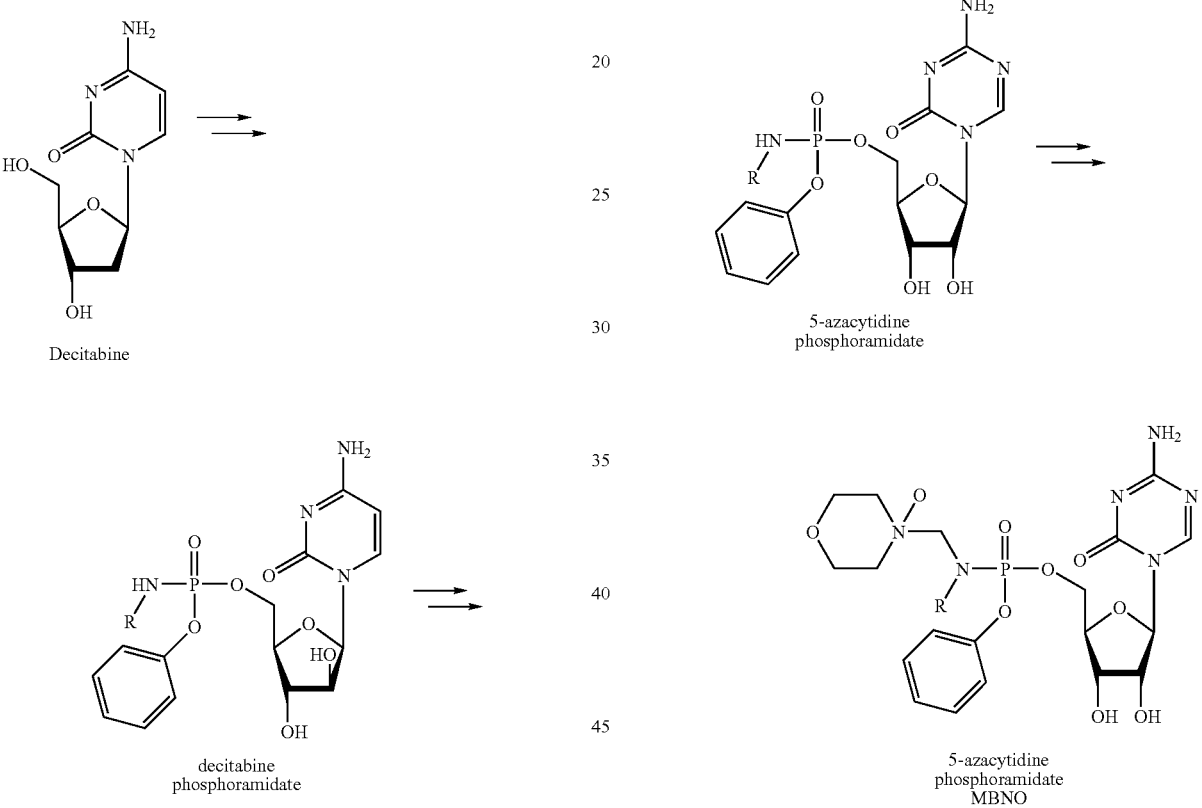
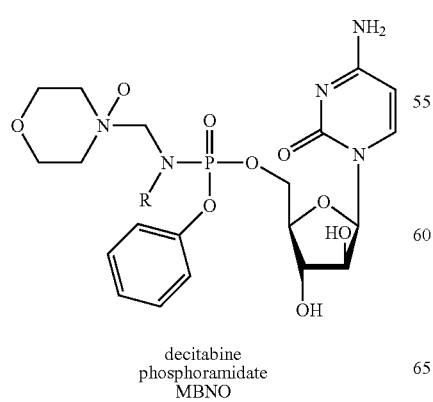
Mannich base N-oxides of various tetracycline derivatives may also be prepared from the parent compounds as shown below:
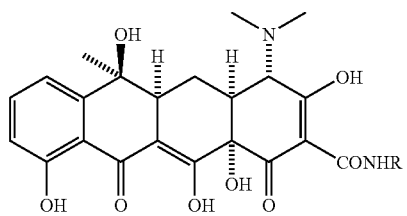
R = H, Tetracycline
R = CH$_2$N(O)Me$_2$, a Mannich base N-oxide

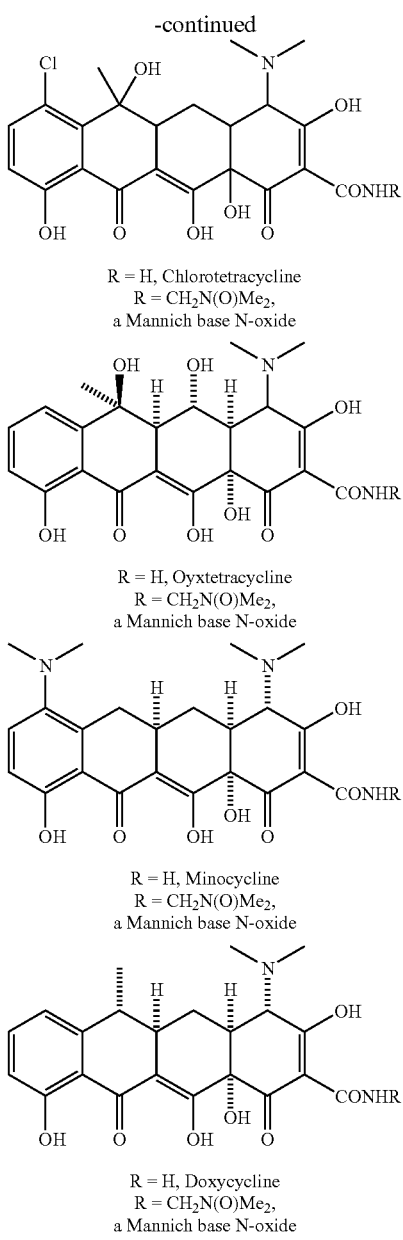

R = H, Chlorotetracycline
R = CH$_2$N(O)Me$_2$,
a Mannich base N-oxide

R = H, Oxytetracycline
R = CH$_2$N(O)Me$_2$,
a Mannich base N-oxide

R = H, Minocycline
R = CH$_2$N(O)Me$_2$,
a Mannich base N-oxide

R = H, Doxycycline
R = CH$_2$N(O)Me$_2$,
a Mannich base N-oxide

Further, the group —NR'$_3$R'$_4$ of formula I may be derived from a taxane. For example, U.S. Pat. No. 6,765,015 discloses taxanes having the general formula:

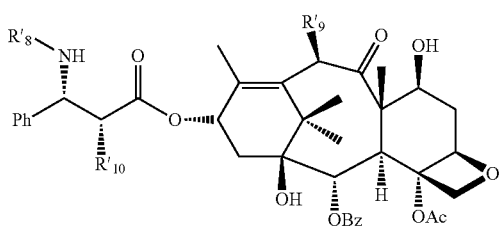

wherein R'$_8$ is mono or dihaloginated acyl group, aroyl group, alkoxycarbonyl, aryloxycarbonyl, or heteroaryloxycarbonyl; R'$_9$ is hydrogen or acyl and R'$_{10}$ is optionally substituted alkylcarbonyl, optionally substituted aryloxycarbonyl, heteroaryloxycarbonyl, optionally substituted aroyl, or optionally substituted heteroaroyl. These taxanes may be converted to a Mannich base N-oxide, which can be schematically drawn as:

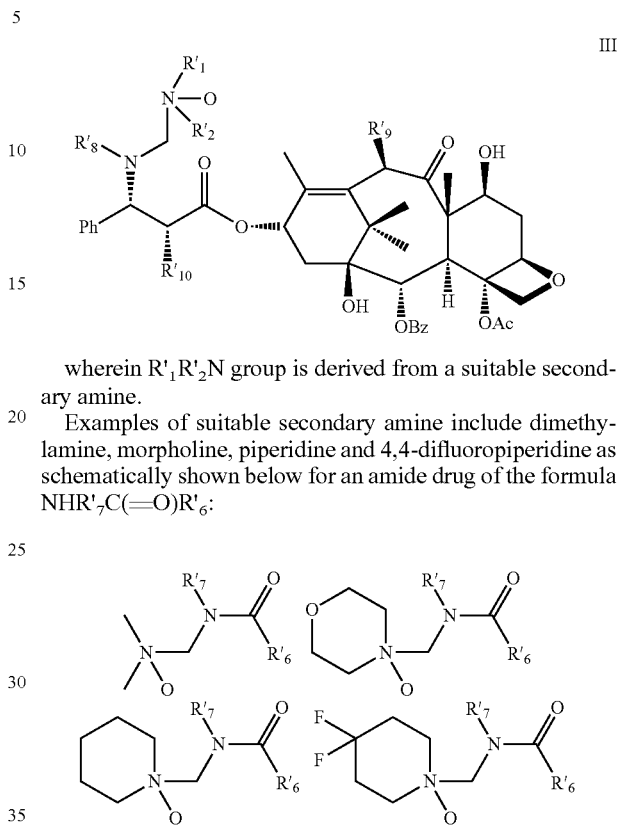

wherein R'$_1$R'$_2$N group is derived from a suitable secondary amine.

Examples of suitable secondary amine include dimethylamine, morpholine, piperidine and 4,4-difluoropiperidine as schematically shown below for an amide drug of the formula NHR'$_7$C(=O)R'$_6$:

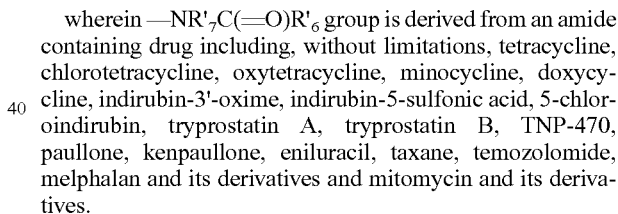

wherein —NR'$_7$C(=O)R'$_6$ group is derived from an amide containing drug including, without limitations, tetracycline, chlorotetracycline, oxytetracycline, minocycline, doxycycline, indirubin-3'-oxime, indirubin-5-sulfonic acid, 5-chloroindirubin, tryprostatin A, tryprostatin B, TNP-470, paullone, kenpaullone, eniluracil, taxane, temozolomide, melphalan and its derivatives and mitomycin and its derivatives.

Mannich base N-oxides such as tegafur Mannich base may be used to prepare 5-FU Mannich base N-oxide as shown in the following scheme:

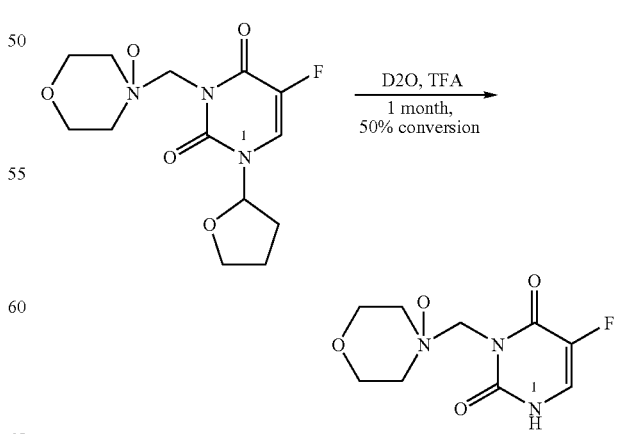

The loss of the tetrahydrofur-2-yl group from tegafur Mannich base N-oxide leads to the formation of 5-FU Mannich base N-oxide. Compounds similar to tegafur Mannich base N-oxide, for example Mannich base N-oxides of 5-azacytidine, 5-aza-2'-deoxycytidine, 5-iodo-2'-deoxycytidine, CAP and Ara-C may also undergo similar elimination and lead to the formation of Mannich N-oxides of 5-FU analogs. Many of the Mannich base N-oxides that are ribofuranosyl substituted uracil derivatives (see above) are also expected to undergo the elimination of the ribofuranosyl group and the formation of the Mannich base N-oxides of uracil derivatives in which $N^1$ is unsubstituted. To illustrate, Mannich base N-oxides of, for example, 1-(5'-O-trityl-β-D-ribofuranosyl)-2',3'-dideoxy-2', 3'-didehydro-5-chlorouracil and 1-(5'-O-trityl-β-D-ribofuranosyl)-2',3'-dideoxy-2',3'-didehydro-5-aminouracil are expected to undergo elimination of the ribofuranosyl group and form Mannich base N-oxides of 5-chlorouracil and 5-aminouracil, respectively. As such, tetrahydrofuryl- and ribofuranosyl-substituted 5-FU analogs may be considered as prodrugs of 5-FU Mannich base N-oxide and its analogs.

It may be possible to control the hydrolytic stability of Mannich bases through the choice of amine used to form the Mannich base. In general, the more basic the amine, the less stable is the Mannich base toward hydrolysis. The same concept might extend to the Mannich base N-oxides. Thus, in those instances where the piperidinyl Mannich base N-oxide, for example, is not sufficiently stable hydrolytically, morpholine or 4,4-difluoropiperidine may provide enhanced hydrolytic stability.

Certain Mannich base N-oxides of 5-FU and its analogs may have biological activity on their own. Others may be hypoxia activatable prodrugs that, upon bioreduction, produce a Mannich base that undergoes a rapid hydrolysis to form the parent 5-FU analog.

The tertiary and/or heteroaromatic amine groups in the Mannich base can selectively be oxidized using known oxidizing agents. Certain oxidizing agents that are known in the art for preparing the N-oxides from aromatic and tertiary amine groups include, without limitation, potassium monopersulfate, monoperoxyphthalic acid, magnesium monoperoxyphthalate (MMPP), hydrogen peroxide, peracetic acid, trifluoroperacetic acid, perbenzoic acid, m-chloroperbenzoic acid (MCPBA), and 2-phenylsulfonyl-3-phenyloxaziridine (Davis reagent). The oxidation reaction can be carried out in a solvent such as chloroform, methylene chloride, 1,2-dichloroethane, or acetic acid, optionally in the presence of an alkali or alkaline-earth metal carbonate or bicarbonate. The reaction can be run from about 1 to 48 hours at a temperature of 0° C. to reflux temperature, and checked periodically for the presence of the desired N-oxide. Depending on the groups bound to the amine, reaction times may need to be adjusted accordingly to obtain appropriate quantities of the desired bis-N-oxide product. See also Lee et al., "Nitracrine N-oxides: effects of variations in the nature of the side chain N-oxide on hypoxia-selective cytotoxicity" *Anticancer Drug Des.* 14(6): 487-497 (1999).

In certain situations, more than one of the nitrogen atoms of a Mannich base may be oxidized simultaneously. In certain cases, one or more of the multiple N-oxide groups may be reduced selectively, leaving one or more of the other N-oxide groups in place. Thus, the present invention contemplates the preparation of N-oxide analogs in which one or more of the nitrogen atoms that are suitable for N-oxide formation are present as the N-oxide without regard to the susceptibility of a particular nitrogen atom to N-oxide formation or the susceptibility of a particular N-oxide group to reduction. It is envisaged to employ a combination of suitable protecting groups (see: Greene, T. W.; Wuts, P. G. M. *Protective Groups in Organic Synthesis*, second edition, Wiley Interscience, 1991) to protect those nitrogen atoms not undergoing oxidation.

By way of an example, primary and secondary amines that are present in a 5-FU analog or prodrug may be protected using, for example, tert-butyl sulfonyl (BUS) group. Jarowicki, K. and Kocienski, P., *J. Chem. Soc., Perkin Trans* 1, 4005-4037, 4029 (1998); Sun, P. and Weinreb, S. M. *J. Org. Chem.* 62:8604-08 (1997). The BUS protecting group is introduced by reaction of the amine with tert-butylsulfinyl chloride followed by oxidation of the sulfinyl amide with, for example, dimethyldioxirane, m-chloroperbenzoic acid or $RuCl_3$ catalyzed $NaIO_4$. The oxidation step in the preparation of the BUS-protected primary or secondary amines may also oxide any tertiary amine and heteroaromatic nitrogen present in the compounds. Thus, this protecting group may be introduced into primary and secondary amines while simultaneously oxidizing tertiary and heteroaromatic nitrogen atoms.

The BUS protecting group is stable towards strong reagents such as alkyllithium, Grignard reagents, 0.1M HCl in MeOH (20° C., 1 hr), 0.1M TFA in dichloromethane (20° C., 1 hr) and pyrolysis at 180° C. The BUS-protected secondary amines can be cleaved with 0.1 M triflic acid in dichloromethane containing anisole as a cation scavenger at 0° C. for 15-30 minutes while primary amines are released more slowly at room temperature. If desired, both BUS-protected primary and secondary amines may be deprotected with 0.1 M triflic acid in dichloromethane containing anisole as a cation scavenger at 25° C. for 2.5 hours. Thus, the BUS protecting group may allow protecting primary and secondary amines simultaneously while also oxidizing tertiary amines and heteroaromatic nitrogen atoms to the N-oxides. Moreover, the BUS protecting group may allow protecting primary and secondary amines simultaneously, oxidizing tertiary amines and heteroaromatic nitrogen atoms to N-oxides, deprotect the secondary amine selectively, alkylate the secondary amine to a tertiary amine, oxidize the resulting tertiary amine and deprotect the primary amine. Alternatively, a primary and a secondary amine may be protected with BUS protecting group, the secondary amine may be deprotected selectively, the secondary amine may be protected with, for example, Boc protecting group, and then the primary amine may be deprotected selectively followed by alkylation and oxidation. Thus, when a primary amine and a secondary amine are present in a 5-FU analog, a BUS protecting group may be used to transform one of amines to an N-oxide without affecting the other.

Recent development in the use of Boc group to protect amines allows introduction and removal of the group under mild conditions. For example, a 5-FU analog or prodrug amine group may be protected with Boc group by simply mixing the analog and Boc-ON (2-(Boc-oxyimino)-2-phenylacetonitrile, available from Aldrich Co.) in benzene at 25° C. for 20 minutes (or 6 hours if the amine is an electron deficient aniline) in the presence of powdered zinc. See Spivey, A. C. and Maddaford A. *Annu. Rep. Prog. Chem., Sect. B,* 95:83-95 (1999). Alkyl esters are tolerated.

Boc-protected amines are generally deprotected using triflic acid although recent developments generally use mildly acidic conditions that leave acid-labile groups unaffected. For example, heating Boc protected p-anisidines at 180° C. in the presence of 4-chlorophenol deprotects the amine group without affecting acid sensitive methoxy enols (—CH=C (OCH$_3$)—). Jarowicki, K. and Kocienski, P., *J. Chem. Soc., Perkin Trans* 1, 4005-4037, 4025 (1998). Thus, primary and secondary amines in 5-FU may be protected with Boc group followed by oxidation of the tertiary amines and deprotection of the primary and secondary amines.

It has also recently been reported a new base-sensitive amino protecting group 1,1-dioxobenzo[b]thiophene-methoxycarbonyl (Bsmoc). Bsmoc is introduced via its chloroformate or N-hydroxy-succinimide derivative. The Bsmoc group is stable towards tertiary amines for 24 hours but is removed within 3-5 minutes using piperidine. Jarowicki, K. and Kocienski, P., *J. Chem. Soc., Perkin Trans* 1, 4005-4037, 4027 (1998). Thus, primary and secondary amines present in a 5-FU analog or prodrug may conveniently be protected with Bsmoc protecting group followed by oxidation of the tertiary amines and removal of the protecting group under mild conditions.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES $^1$H NMR spectra were obtained from INOVA-300 MHz or INOVA-500 MHz spectrometers using CDCl$_3$ as a solvent (s, d, t, dd and m indicate singlet, doublet, triplet, doublet of doublet, and multiplet, respectively). Analytical thin-layer chromatography was performed on polyester-backed plated precoated with silica gel 60 Å (SILG/UV$_{254}$, a Whatman® Flexible-Backed TLC Plate with UV254 fluorescent indicator). Radial thin-layer chromatography was performed on a Harrison Research Chromatron (7924T) with 2 mm thick silica plates (silica gel 60 PF$_{254}$ with gypsum, EMD Chemicals, Inc.). Analytical scale high-performance liquid chromatography (HPLC) was performed on a 4.6 mm×250 mm MICROSORB C$_{18}$ column using a pressure of 1800-2100 psi.

Example 1

Preparation of Benzamide Mannich Bases

Benzamide Mannich base 7. A mixture of benzamide 1 (0.11 g, 0.88 mmol), 4,4-difluoropiperidine 6 (0.11 g, 0.88 mmol) and formaldehyde (0.065 mL, 37% solution in water, 0.88 mmol) in water (5 mL) was heated at 60° C. until the benzamide was dissolved. After 24 h of stirring at room temperature Na$_2$CO$_3$ (about 100 mg) was added and the desired compound was extracted with ether (3×10 mL). The combined extracts were dried over Na$_2$SO$_4$. Evaporation of solvents gave crude Mannich base 7, which was chromatographed on the Chromatotron with a chloroform/methanol mixture (50:1). Concentration of eluate gave benzamide Mannich base 7 (0.04 g, 20%) as a sticky solid pure by TLC and $^1$H NMR. $^1$H NMR (CDCl$_3$) δ 1.97-2.09 (m, 4H), 2.78 (t, J=6.0, 4H), 4.39 (d, 7 J=6.3, 2H) 7.44-7.58 (m, 3H), 7.79-7.82 (m, 2H).

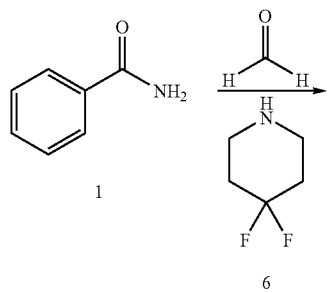

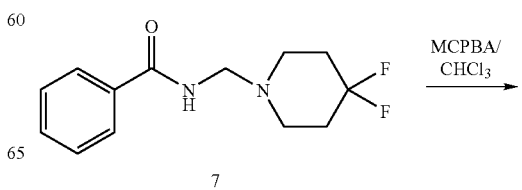

Synthesis of the model benzamide Mannich base 4 was performed according to a literature procedure by reaction of benzamide 1 with formaldehyde 2 and dimethylamine 3 in water. Anker, L. et al., *Helvetica Chimica Acta*, 66:542-555 (1983).

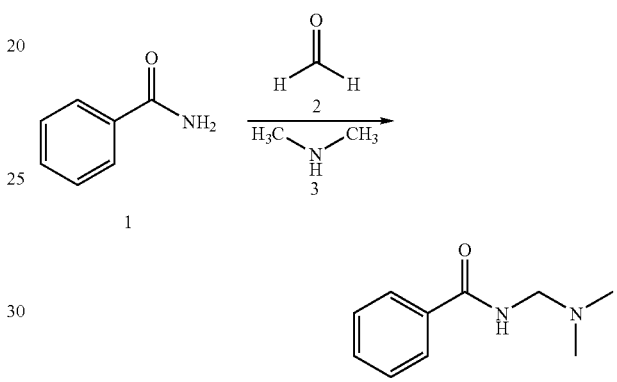

Example 2

Preparation of Benzamide Mannich Base N-Oxides

N-oxide Mannich base 8. 0.01 g (0.043 mmol) of Mannich base 7 was dissolved in 1 mL of chloroform. To this solution, m-chloroperoxybenzoic acid (0.01 g, 0.06 mmol) in chloroform (1 mL) was added with stirring at room temperature. The solution was stirred at room temperature for 15 min. The solvent was evaporated to give crude N-oxide 8 as yellowish oil. It was chromatographed on a TLC preparative plate with chloroform/methanol 5:1 mixture. Desired fractions were collected and eluted with chloroform/methanol 5:1 mixture. Evaporation of the eluant gave N-oxide 8 (0.005 g, 45%) as a waxy solid which was pure by TLC and $^{1H}$ NMR: $^1$H NMR (CDCl$_3$) δ 1.92 (brs, 2H), 2.21 (brs, 2H), 3.10 (brs, 4H), 5.05 (d, J=6.3, 2H) 7.46-7.59 (m, 3H), 7.82-7.85 (m, 2H).

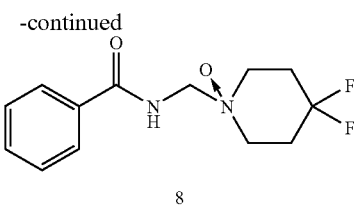

8

N-oxide Mannich base 5. Benzamide Mannich base 4 was converted into the Mannich base N-oxide 5 using m-chloroperoxybenzoic acid (MCPBA) in chloroform at room temperature. 0.15 g (0.84 mmol) of Mannich base 4 was dissolved in 2 mL of chloroform. To this solution, m-chloroperoxybenzoic acid (0.22 g, 1.2 mmol) in chloroform (2 mL) was added with stirring at rt. The solution was stirred at room temperature for 30 min. The solvent was evaporated to give crude N-oxide 5 as yellowish oil. It was chromatographed on a Chromatotron using a 2 mm disk. m-Chlorobenzoic acid and other faster-eluting impurities were eluted with 5:1 methylene chloride/methanol mixture. The desired N-oxide 5 was eluted with 5:3 methylene chloride/methanol mixture. Concentration of the eluate gave N-oxide 5 (0.1 g, 61%) as oil, which became a waxy solid upon storage in a freezer, which was pure by TLC and NMR. $^1$H NMR (CDCl$_3$) δ 2.60 (s, 6H), 5.02 (d, J=6.9, 2H), 7.44-7.57 (m, 3H), 7.83-7.86 (m, 2H). $^{13}$C NMR (CDCl$_3$) δ 48.47, 71.61, 127.38, 128.87, 132.09, 134.36, 167.76; MS (m/e): Calculated. for 4 $C_{10}H_{15}N_2O$ (M+H), 179.1. Found (M+H) 178.9. Calculated. for 5: $C_{10}H_{15}N_2O_2$ (M+H), 195.1. Found (M+H) 194.9.

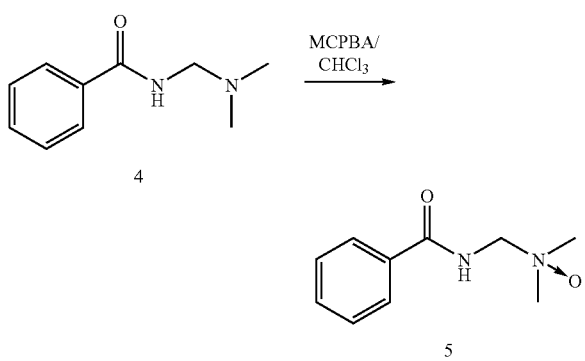

Example 3

Preparation of Benzamide Mannich Base N-Oxide: One-Step Process

N,N-Dimethylhydroxylamine free base was prepared from N,N-dimethylhydroxylamine hydrochloride according to the following procedure and then used in the form of a methanolic solution.

N,N-dimethylhydroxylamine HCl (313.5 mg, 3.210 mmol) was dissolved in 2 mL of MeOH in a 10 mL round bottom flask. NaOCH$_3$ (0.75 mL, 3.3 mmol, 25% in MeOH) was added at once to the solution in the 10 mL round bottom flask while stirring at room temperature. A white solid came out of solution and the slurry was left stirring for 5 min. The slurry was filtered through a micron filter under vacuum into a clean 25 mL round bottom flask. The white solid (NaCl) that was left behind in the reaction flask was rinsed with MeOH (1×1 mL) to remove any residual amine. The MeOH rinse was combined with the filtrate and used as the source of N,N-dimethylhydroxylamine for preparation of the Mannich base N-oxide as follows.

Benzamide (386.9 mg, 3.198 mmol) was suspended in 5 mL of H$_2$O in a 25 mL round bottom flask. Formaldehyde (0.2 mL, 2 mmol, 37% in H$_2$O) was added at once to the suspension while stirring at room temperature. N,N-dimethylhydroxylamine (196 mg, 3.21 mmol) in 3 mL of MeOH (see above) was added at once to the suspension while stirring at room temperature. A condenser was attached to the round bottom flask with the reaction solution. An oil bath was used to heat the reaction solution at 68° C. overnight. After 24 h, the reaction solution was spotted on a TLC plate next to the benzamide Mannich base N-oxide made during a previous synthesis and eluted with 5:1 CHCl$_3$:CH$_3$OH. The R$_f$ value of the spot for the N-oxide (R$_f$=0.7) from the previous synthesis was equal to the R$_f$ value for the leading spot from the reaction solution, but the TLC indicated an incomplete reaction. Consequently, the temperature of the reaction mixture was raised to 75° C. and left for 72 h. TLC analysis indicated that the reaction had proceeded further but was still incomplete. At this point the reaction solution was cooled and then extracted with Et$_2$O (3×15 mL). The solvents were removed from each layer. The yellow solid obtained from the aqueous layer (297 mg) was dissolved in CHCl$_3$ (2 mL) and loaded onto a 2 mm silica gel plate. The leading band during chromatography was the benzamide Mannich base N-oxide and had the same R$_f$ value as that of an independently prepared sample of N-oxide. After solvent removal, a yellow solid was obtained (35.1 mg, 9% yield).

Example 4

Preparation of Tegafur Mannich Base N-Oxide

Tegafur Mannich Base 6. 0.041 g (0.5 mmol) of Formaldehyde 4 (37% solution in water) was added to 0.044 g (0.5 mmol) of morpholine 5 at ice/water bath temperature followed by 2 mL of THF. The solution was stirred for 10 min and 0.1 g (0.5 mmol) of Tegafur was added to the solution. The Tegafur gradually went into solution. The mixture was allowed to warm to room temperature and stirred for 18 h. Solvents were evaporated and residue was dried in vacuum to give Mannich base 6 as white glassy foam (0.15 g, 100%) with purity by TLC and NMR approaching 100%. The sample was used for the next step without any purification. The $^1$H NMR (CDCl$_3$) δ 1.89-2.00 (m, 1H), 2.00-2.14 (m, 2H), 2.38-2.47 (m, 1H), 2.71-2.75 (m, 4H), 3.67 (t, J=4.5, 4H), 3.98-4.06 (m, 1H), 4.22-4.29 (m, 1H), 4.96 (AB system, J=12.6, 2H), 5.96-6.02 (m, 1H), 7.42 (d, J=6.0, 1H). $^{19}$F NMR spectra (CDCl$_3$) δ 12.64 (d, J=5.7, 1F)

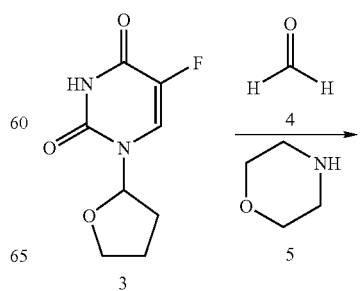

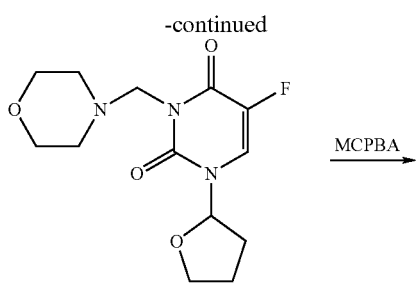

6

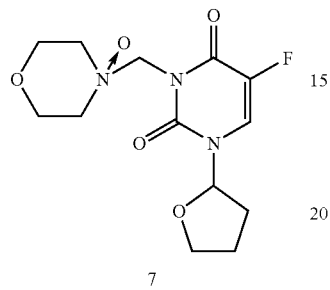

7

Tegafur Mannich Base N-Oxide 7. Mannich base 6 (0.13 g, 0.45 mmol) was dissolved in chloroform (1 mL). To this solution MCPBA (m-chloroperbenzoic acid, 0.12 g, 0.68 mmol) in chloroform (1 mL) was added. The mixture was stirred for 30 min (reaction was monitored by TLC until starting material was consumed). The solvents were evaporated and the residue was purified on the Chromatotron and elution with an ethyl acetate/methanol mixture. The faster moving, less polar impurities were eluted with a 5:1 mixture of ethyl acetate/methanol and the desired N-oxide was eluted with a 5:2 mixture. N-oxide 7 was obtained in 77% yield (0.11 g) with a purity of about 98% by TLC and NMR. $^1$H NMR (CDCl$_3$) δ 1.82-1.98 (m, 1H), 2.00-2.18 (m, 2H), 2.35-2.50 (m, 1H), 3.02-3.22 (m, 2H), 3.22-3.42 (m, 2H), 3.68-3.80 (m, 2H), 3.96-4.04 (m, 1H), 4.23 (bs, 1H), 4.44 (t, J=11.4, 2H), 5.20-5.42 (m, 2H), 5.95 (s, 0.5H), 5.97 (s, 0.5H), 7.50 (d, J=5.7, 1H); $^{13}$C NMR spectra (CDCl$_3$) δ 23.94, 33.33, 61.68, 64.15, 70.81, 71.36, 88.89, 123.34, 123.83, 138.11, 141.20, 149.28, 157.22, 157.58; $^{19}$F NMR (CDCl$_3$) δ 12.85 (s, 0.5F), 13.12 (s, 0.5F). MS (m/e): Calculated. for C$_{13}$H$_{18}$FN$_3$O$_5$ (M+1), 316.1. Found (M+1) 315.9. Calculated for 2C$_{13}$H$_{18}$FN$_3$O$_5$ (2M), 630.25. Found (2M) 630.7. Anal. Calculated for C$_{13}$H$_{18}$FN$_3$O$_5$.9/5H$_2$O: C, 44.90; H, 6.26; N, 12.08. Found C, 45.12; H, 6.02; N, 11.93.

Dissolution of Tegafur Mannich base N-oxide in water followed by lyophilization gives Tagafur Mannich base N-oxide as a fluffy white powder, which can be removed easily from the flask.

Examples 5-14 describe the synthesis of several Mannich bases (structures B and structures G in Chart 1) and the corresponding Mannich base N-oxides (structures C and H). In cases where R=H in structure A, the synthesis of the rearranged N-oxide isomer D is also described. In general, Mannich base N-oxides (structures C) derived from amide-type nitrogen atoms of general structure A where R is alkyl or a carbonyl group are stable and do not undergo rearrangement to the corresponding isomer (structures D). However, when R=H in A, the Mannich base N-oxide C (R=H) undergoes rearrangement over time to the corresponding isomer D. Rearrangement tends to be very slow (several days) in aqueous solution but more rapid (a few hours) in CDCl$_3$ and depends to some extent on which secondary amine was used to prepare the Mannich base. In one case, the hydrochloride salt (structure E) of a Mannich base N-oxide C where R=H was prepared. Mannich base N-oxide salt E was stable toward rearrangement.

Mannich base N-oxides H derived from sulfonamide-type nitrogen atoms of general structure F where R is alkyl are stable and do not undergo rearrangement to the isomeric structure I. However, attempts to prepare Mannich base N-oxides H (R=H) from primary sulfonamides (structures F where R=H) were not successful and resulted in a complex mixture of compounds that may contain some H (R=H) and I (R=H).

Chart 1

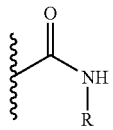

A

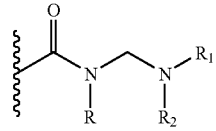

B

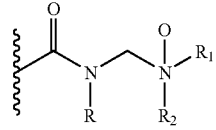

C

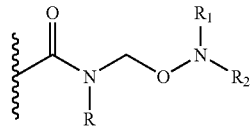

D (formed from C only when R = H)

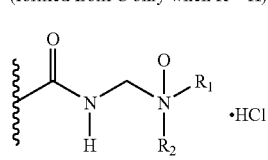

•HCl

E

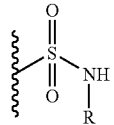

F

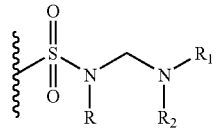

G

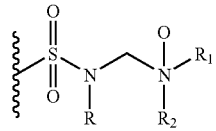

H

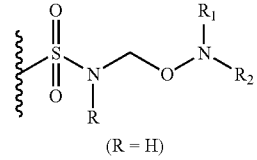

(R = H)

I

Example 5

Synthesis of Mannich Base N-Oxides 3, 4 and 5 Derived from 5-Fluorouracil (5FU), Morpholine and Formaldehyde

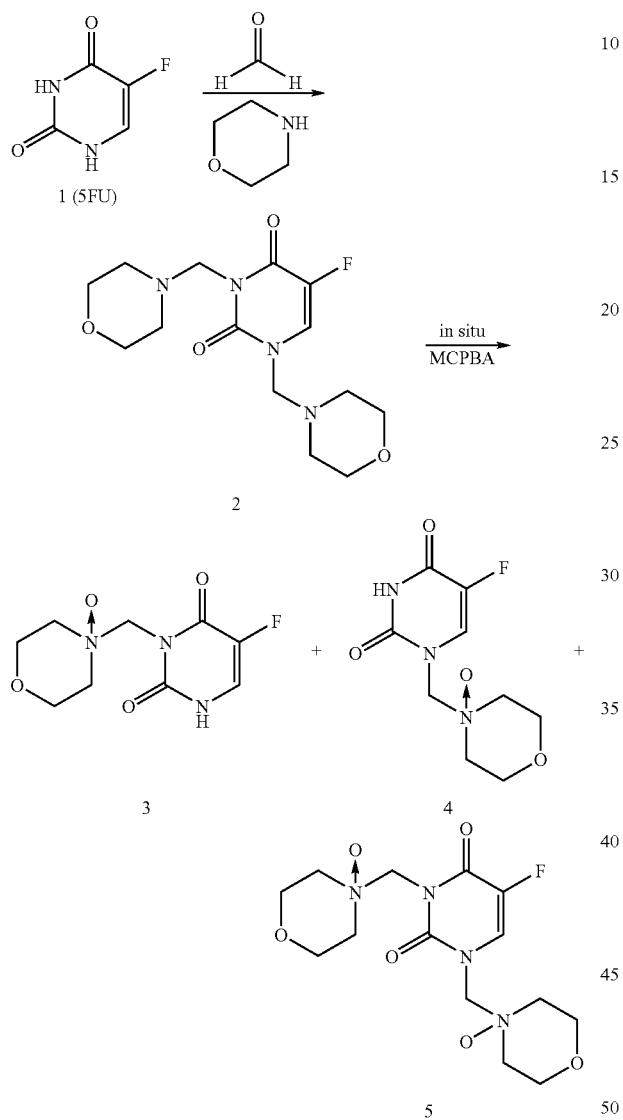

5-Fluoro-1,3-bis-morpholin-4-ylmethyl-1H-pyrimidine-2,4-dione (2). The synthesis of the $N^1,N^3$-bis-Mannich base 2 of 5-fluorouracil (1) was accomplished as described by Sloan et al., *International Journal of Pharmaceutics* 21:251-264 (1984). Formaldehyde (0.60 mL of 37% solution in water, 7.6 mmol) was added to morpholine (0.66 mL, 7.6 mmol) at ice/water bath temperature. The solution was stirred for 10 min and then 5-FU (0.5 g, 3.8 mmol) was added followed by 2 mL of THF. 5-FU gradually went into solution during the first 2 h. The solution was allowed to stir overnight. Owing to the extreme sensitivity of Mannich base 2 toward hydrolysis, this solution was used immediately in the next reaction.

5-Fluoro-3-(4-oxido-morpholin-4-yl-methyl)-1H-pyrimidine-2,4-dione (3) and 5-fluoro-1-(4-oxido-morpholin-4-yl-methyl)-1H-pyrimidine-2,4-dione (4) and 5-fluoro-1,3-bis-(4-oxido-morpholin-4-yl-methyl)-1H-pyrimidine-2,4-dione (5). The reaction mixture containing 2 was poured at once into a stirred solution of MCPBA (6.57 g, 38 mmol) in dichloromethane (50 mL) at ice/water bath temperature. Two new spots more polar than that of 5-FU were detected by tlc immediately after the reaction with MCPBA. The solution was stirred for 5 min and then water (50 mL) was added. The mixture was extracted with dichloromethane (3×50 mL) and the water phase was evaporated to give an off-white solid (~0.9 g). The crude product was chromatographed on a Chromatotron using dichloromethane/methanol as the eluent to give 490 mg (53% yield) of a mixture of 3 and 4. Continued elution with 5:3:1 dichloromethane/methanol/ammonia gave 15 mg (1.1%) of bis-Mannich base N-oxide 5. The $^1$H and $^{19}$F NMR spectra of 5 ($D_2O$) were consistent with the assigned structure. APCI MS (m/e): Calcd. for 5 $C_{14}H_{21}FN_4O_6$ (M+H), 361.1. Found: (M+H) 361.1.

The mixture of 3 and 4 was rechromatographed on a Chromatotron with 5:3:0.3 dichloromethane/methanol/ammonia as eluent to give 200 mg (22%) of the $N^3$ isomer 3 (faster moving isomer on TLC) which was pure by TLC, $^1$H and $^{19}$F NMR spectroscopy. The $^1$H and $^{19}$F NMR spectra of 3 ($D_2O$) were consistent with the assigned structure. APCI MS (m/e): Calcd. for $C_9H_{12}FN_3O_4$ (M+H), 246.0; found (M+H) 246.0. Continued elution gave 140 mg (15% yield) of the $N^1$ isomer 4 (slower moving spot on TLC), which was pure by TLC, $^1$H and $^{19}$F NMR spectroscopy. APCI MS (m/e): Calcd. for $C_9H_{12}FN_3O_4$ (M+H), 246.0; found (M+H) 246.0. N-oxides 3, 4, and 5 were stable in $D_2O$ for at least several days as monitored by $^1$H NMR spectroscopy. The structures of Mannich base N-oxides 3 and 4 were confirmed by single crystal x-ray analysis. Example 6

Reduction of 5-FU-Derived Mannich Base N-Oxides 3 and 4 in $CDCl_3$

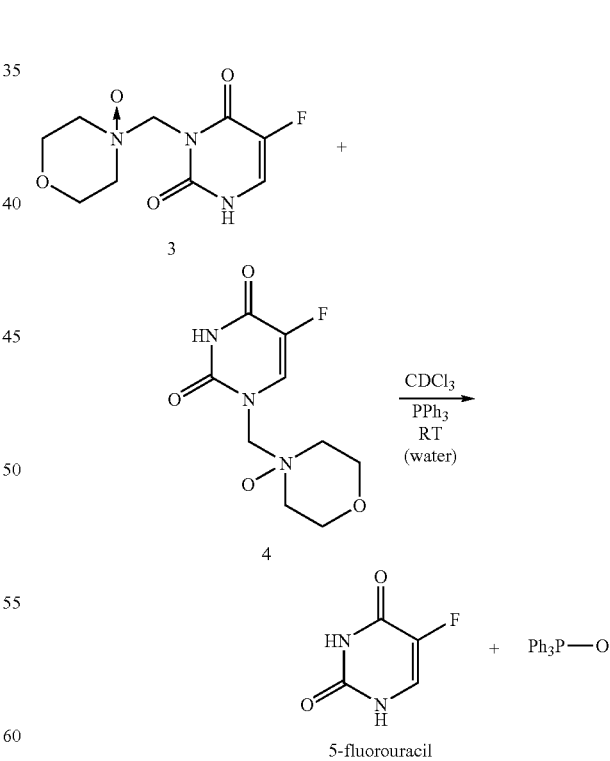

Triphenylphosphine is known to reduce N-oxides to the corresponding amines See Gallos, J. K. and Argyropoulos, N. G. *Synthesis* 1:83-86 (1991). A mixture of N-oxides 3 and 4 was dissolved in $CDCl_3$ and then treated with 2 equiv of triphenylphosphine in $CDCl_3$ at RT and monitored by $^1$H and $^{19}$F NMR spectroscopy. According to the $^1$H and $^{19}$F NMR spectra, the N-oxides underwent reduction and spontaneous hydrolysis to 5-fluorouracil to the extent of about 90% over a 70-h time period. Thus, not only are the N-oxide groups reduced back to the corresponding Mannich bases, but also the Mannich bases undergo hydrolysis back to 5-FU in the presence of adventitious water.

Example 7

Synthesis of Mannich Base N-Oxides 7, 8 and 9 Derived from 5-Fluorouracil, Dimethylamine and Formaldehyde

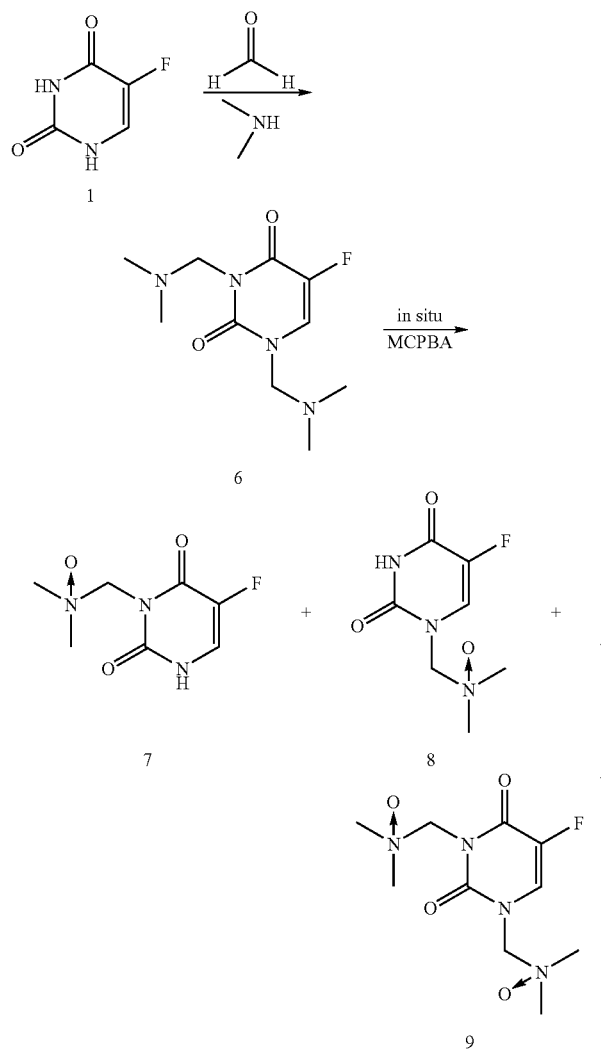

Essentially the same procedure that was used for the synthesis of 5-FU Morpholine Mannich base N-oxides 3, 4, and 5 was used here for the synthesis of 7, 8 and 9.

1,3-Bis-dimethylaminomethyl-5-fluoro-1H-pyrimidine-2,4-dione (6). The synthesis of the bis Mannich base 6 was accomplished as described by Sloan et al., *International Journal of Pharmaceutics* 21:251-264 (1984). These investigators observed that bis Mannich base 6 was very sensitive toward hydrolysis and could not be isolated as a stable molecule. Formaldehyde (0.25 mL of 37% solution in water, 3.4 mmol) was added to aqueous dimethylamine (40% solution in water, 0.43 mL, 3.4 mmol) at ice/water bath temperature. The solution was stirred for 10 min and then 5-FU (0.2 g, 1.5 mmol) was added. 5-FU gradually went into solution during the first 2 h. The solution was stirred overnight to generate Mannich base 6 and then the solution was used immediately in the next reaction.

3-Dimethyl-(N-oxido)-aminomethyl-5-fluoro-1H-pyrimidine-2,4-dione (7) and 1-dimethyl-(N-oxido)-aminomethyl-5-fluoro-1H-pyrimidine-2,4-dione (8) and 1,3-bis-dimethyl-(N-oxido)-aminomethyl-5-fluoro-1H-pyrimidine-2,4-dione (9). The solution from the previous reaction was added to a stirred solution of MCPBA (0.88 g, 5.0 mmol) in dichloromethane (16 mL) while cooled in an ice/water bath. Two new much more polar spots were detected by tlc immediately after the MCPBA was added. The solution was stirred for 10 min and then water (15 mL) was added. The desired N-oxides 7, 8 and 9 went into the water phase. The water phase was separated and washed with dichloromethane (2×15 mL). The water volume was reduced to 1 mL and sufficient silica gel (silica gel 150, 50-200 Mesh, 75-250μ) was added to absorb the water and compounds. After drying under vacuum, the silica gel was transferred to a column and the crude product was chromatographed with dichloromethane/methanol as an eluent. 5-FU and other less polar impurities were eluted with 5:1 and then the desired N-oxides were eluted with 5:3 dichloromethane/methanol. The desired fractions containing a mixture of 7 and 8 were collected (0.06 g, 19% yield). Continued elution did not produce appreciable amounts of bis N-oxide 9, which could be detected as a slow-moving spot on tlc.

The separation of the mixture of Mannich base N-oxide isomers 7 and 8 was performed on a Chromatotron using 5:3 dichloromethane/methanol as the eluent. It was important to have a high silica gel/product ratio to achieve a good separation. The yield of compound 7 was 30 mg (10%) and compound 8 was 12 mg (4%). The $^1$H and $^{19}$F NMR spectra were consistent with the assigned structures. APCI MS (m/e) for 7 and 8: Calcd. For $C_7H_{11}FN_3O_3$ (M+H), 204.0; found (M+H) 204.0.

Example 8

Synthesis of Mannich Base N-Oxides 10 and 11 Derived from 5-FU, Piperidine and Formaldehyde

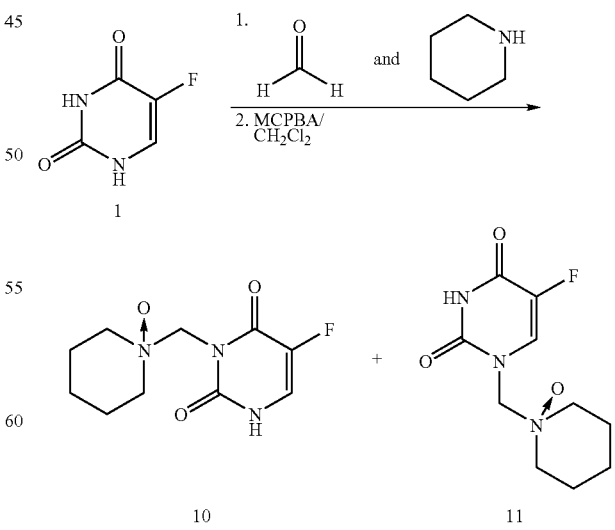

The synthesis of the Mannich base N-oxides 10 and 11 was accomplished using a procedure that is similar to that used for the synthesis of 5-FU-morpholine derived Mannich base N-oxides 3 and 4 but in this case without isolation of the intermediate Mannich bases.

5-Fluoro-3-(1-oxido-piperidin-1-ylmethyl)-1H-pyrimidine-2,4-dione (10) and 5-fluoro-1-(1-oxido-piperidin-1-yl-methyl)-1H-pyrimidine-2,4-dione (11). Formaldehyde (0.07 mL of 37% solution in water, 0.93 mmol) was added to piperidine (0.08 g, 0.93 mmol) at ice/water bath temperature. The solution was stirred for 10 min and then 5-FU (0.055 g, 0.42 mmol) was added followed by 1 mL of THF. The resulting solution was stirred overnight. After that time the solution was added to a stirred solution of MCPBA (0.37 g, 2 mmol) in dichloromethane (2 mL) at ice/water bath temperature. Two new much more polar spots were detected by tlc immediately after the MCPBA was added. The solution was stirred for 1 h and then the solvents were evaporated. The crude product was chromatographed on a Chromatotron. About 40 mg (50% yield) of a 2:1 mixture of 10 and 11 was obtained using dichloromethane/methanol/ammonia as the eluent. Formation of the corresponding bis-Mannich base N-oxide was not observed in this experiment, although the compound may have been formed in a trace amount.

Example 9

Synthesis of Mannich Base N-Oxide 13 Derived from Benzamide, Dimethylamine and Formaldehyde, and its Rearranged Product 14

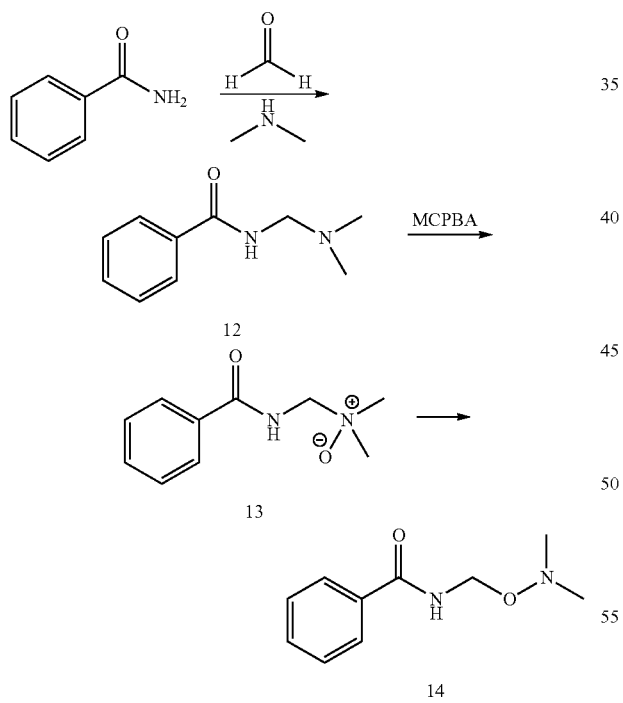

Dimethylaminomethylbenzamide (12). Mannich base 12 derived from benzamide, dimethylamine and formaldehyde was synthesized according to the procedure of Anker et al. (Anker, L. et. al *Helvetica Chimica Acta* 66:542-556 (1983)). A stirred suspension of benzamide (0.214 g, 1.8 mmol) in H$_2$O (5 mL) was mixed with aqueous dimethylamine (40% in water, 0.22 mL, 0018 mol) and 37% formaldehyde (0.13 mL, 0.0018 mol). After a 5-10 min heating period at 60° C., the solution was allowed to cool to rt over 1 h and then it was saturated with Na$_2$CO$_3$. The oil which separated was recovered and extracted with ether. The crude product was chromatographed on a Chromatotron with chloroform/MeOH , 5:1 to 5:2 as eluent. The desired fractions were collected and the solvents were evaporated to give Mannich base 12 as a white solid (0.28 g, 90%) yield.

N-(Dimethyl-N'-oxido-aminomethyl)-benzamide (13) and N-(Dimethyl-aminooxymethyl)-benzamide (14). Mannich base 12 (0.18 g, 0.001 mol) was dissolved in dichloromethane (5 mL) and then solid MCPBA (0.26 g, 0.0015 mol) was added to the stirred solution in an ice/water bath. After stirring for 20 min as the solution warmed to RT, the solvent was evaporated. The residue was chromatographed on a Chromatotron with dichloromethane/methanol as eluent. Evaporation of the eluent in the cold is accompanied by rearrangement, giving 150 mg (66%) of the mixture Mannich base N-oxide 13 (R$_f$~0.2 in dichloromethane/methanol, 5:1) and the rearranged benzamide derivative 14 (R$_f$~0.8 in dichloromethane/methanol, 5:1). A sample of the mixture was allowed to stand in CDCl$_3$ at RT while it was monitored by $^1$H NMR. Essentially complete conversion to the rearranged product 14 was observed over a period of several hours.

The $^1$H and $^{13}$C NMR spectra are consistent with assigned structures. APCI MS (m/e) for 14: Calcd. for C$_{10}$H$_{15}$N$_2$O$_2$ (M+1), 195.1. Found (M+1) 195.1.

Example 10

Synthesis of Mannich Base N-Oxide 16 Derived from Benzamide, Piperidine and Formaldehyde, and its Rearranged Product 17

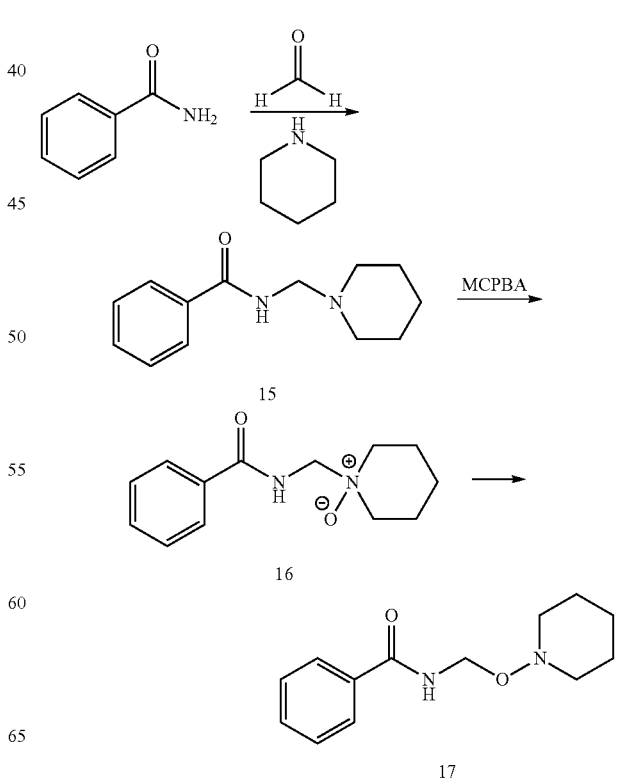

N-Piperidin-1-ylmethyl-benzamide (15). Benzamide (0.5 g, 0.4 mmol) was dissolved in 5 mL of methanol. To this stirred solution piperidine (0.35 mL, 0.4 mol) was added and the resulting solution was cooled in an ice bath. Formaldehyde (0.31 mL, 0.4 mol, 37% in water) was added dropwise. The solution was stirred for 10 min and then it was refluxed for 4 h. After cooling, the solvents were evaporated to give Mannich base 15 as a white solid 0.78 g (87% yield).

N-(Piperidin-1-oxido-1-yl-methyl)-benzamide (16) and N-(Piperidin-1-yloxymethyl)-benzamide (17). Mannich base 15 (0.2 g, 0.92 mmol) was dissolved in 2 mL of dichloromethane and then the solution was added to a stirred solution of MCPBA (0.24 g, 1. 14 mmol) in 2 mL of dichloromethane in an ice/water bath. After 5 min of stirring at RT, the solvent was evaporated and the residue was chromatographed on a Chromatotron with dichloromethane/methanol mixture, 5:1 to 5:3 as eluent. The desired fractions were combined and the solvents were evaporated to give Mannich base N-oxide 16 (0.15 g, 72% yield). As was observed with Mannich base N-oxide 13 derived from dimethylamine, during evaporation of the eluent containing 16, some rearranged product 17 is formed. The $^1$H and $^{13}$C NMR spectra of 17 are consistent with the assigned structure. Rearrangement of 16 to 17 starts immediately after adding CDCl$_3$. It was difficult to get clean NMR spectra of 16 in any solvent. The $^1$H NMR spectrum of 16 in D$_2$O shows 10-20% of rearranged product 17.

Example 11

Synthesis of Mannich Base N-Oxide 19 Derived from Benzamide, Morpholine and Formaldehyde, Hydrochloride Salt 21 and the Rearranged Product 20.

N-Morpholin-4-ylmethyl-benzamide (18). To a stirred solution of benzamide (0.30 g, 2.5 mmol) in MeOH (5 mL) was added morpholine (0.22 g, 2.5 mmol) and the resulting solution was cooled in an ice bath. Formaldehyde (0.215 mL, 2.5 mmol, 37% in water) was then added and the stirred solution was left on ice for 5 min and then it was allowed to stand at RT for another 10 min, and then it was placed in a 70° C. oil bath for 2 h. The solvents were evaporated and the isolated residue (a waxy solid) was chromatographed on a Chromatotron with dichloromethane/methanol mixture, 5:0.2 to 5:0.6 as eluent. The desired fractions were collected and the solvents were evaporated giving Mannich base 18 (0.145 g, 30%) as an oil which solidified in the freezer.

N-(Morpholin-4-oxido-4-ylmethyl)-benzamide (19) and N-(Morpholin-4-oxido-4-ylmethyl)-benzamide Hydrochloride (21) and N-(Morpholin-4-yloxymethyl)-benzamide (20). Mannich base 18 (0.283 g, 1.3 mmol) was dissolved in dichloromethane (6 mL) and the solution was cooled in an ice/water bath. To this stirred solution MCPBA (0.3 g, 1.7 mmol) was added as a solid. After 10 min the reaction mixture was divided in half. The first half was evaporated and chromatographed on a Chromatotron with dichloromethane/methanol 5:0.5 to 5:2 as eluent giving mostly rearranged product 20 (0.1 g, 67%). A chloroform solution of the mixture was allowed to stand at RT for 72 h during which time 19 underwent clean conversion to rearranged product 20. The $^1$H and $^{13}$C NMR spectra of 20 were consistent with the assigned structure. APCI MS (m/z): Calcd. for 20, C$_{12}$H$_{17}$N$_2$O$_3$ (M+1) 236.1; Found 236.1 A sample of 20 was recrystallized from EtOAc/hexanes giving crystals that were subject to x-ray analysis.

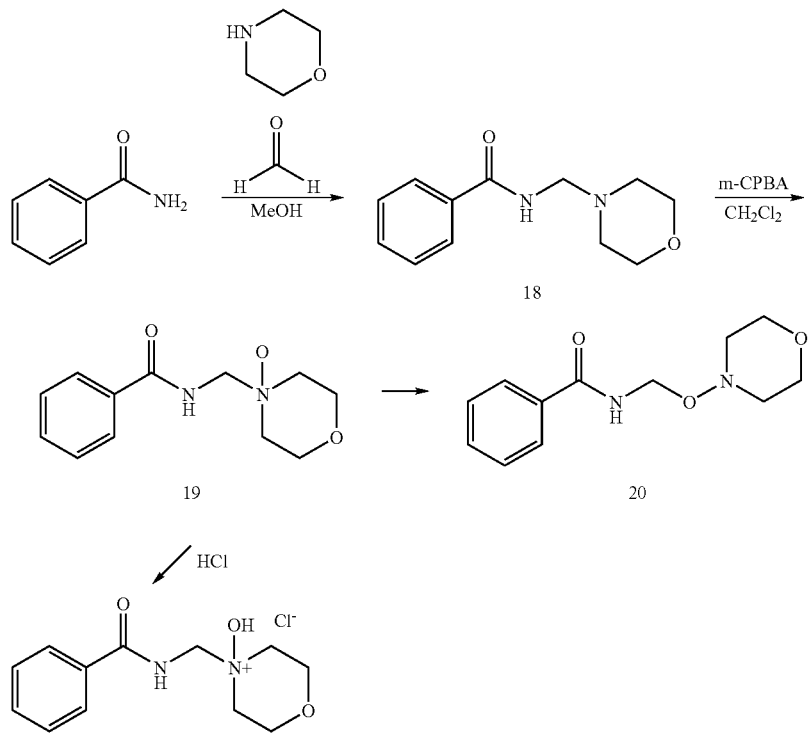

The second half of the MCPBA oxidation solution was extracted with 1N HCl. The water layer was evaporated to dryness and then the residue was treated with dichloromethane and re-evaporated to give the N-oxide HCl salt 21 (0.11 g, 73%) as a waxy solid which was stable in CDCl$_3$ solution for several days. The $^1$H NMR spectra were consistent with the assigned structure. A chloroform solution of 21 was allowed to stand at RT for 72 h during which time no rearranged product 20 was formed. A sample of 21 was recrystallized from MeOH/Et$_2$O giving crystals that were subject to x-ray analysis. APCI MS (m/z APCI MS (m/z): Calcd. 21 C$_{12}$H$_{17}$N$_2$O$_3$ (M+1) 236.1; Found 236.1.

Example 12

Synthesis of Mannich Base N-Oxide 25 Derived from N-Methylbenzamide and N,N-Dimethylmethyleneammonium Chloride (23).

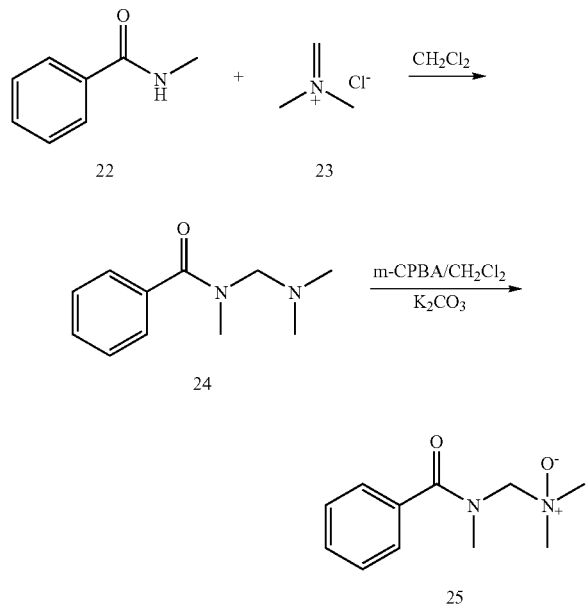

N-(Dimethylaminomethyl)-N-methyl-benzamide (24) and N-(Dimethyl-N'-oxido-aminomethyl)-N-methyl-benzamide (25). Mannich base 24 was prepared by the method of Freeman and Harger (Freeman, S. and Harger, M.J.P. *J. Chem. Research (S)* 354-355 (1989)). N-Methylbenzamide 22 (101 mg, 0.75 mmol, 99+%, Aldrich, used as received) was dissolved in dichloromethane (5 mL). To the stirred solution, 94 mg (1.0 mmol, 1.3 mol. eq.) of N,N-dimethylmethyleneammonium chloride (23) (Aldrich tech 90%, used as received) was added. The solution was allowed to stir at RT. After 1.5 h of stirring anhydrous K$_2$CO$_3$ (0.26 g, 1.9 mmol) was added. To the resulting stirred mixture containing 24 was added solid MCPBA (0.19 g, 1.12 mmol). The resulting suspension was stirred overnight at RT. After 20 h the resulting suspension was filtered through a pad of MgSO$_4$ and then the solvent was evaporated. The residue was chromatographed on a Chromatotron with a dichloromethane/methanol mixture, 5:1 to 5:3, as eluent giving N-oxide 25 as a yellowish oil (0.1 g, 57% yield) which solidified upon storage in the freezer. $^1$H NMR (300 MHz, CDCl$_3$), 7.46-7.55 (m, 5H), 4.94 (s, 2H), 3.51 (s, 3H), 3.25 (s, 6H); APCI MS (m/e): Calcd. for C$_{11}$H$_{16}$N$_2$O$_2$ (M+1), 209.1. Found (M+1) 209.1. Mp 100.5-103.0° C. A sample was crystallized from EtOAc/Hexanes and the structure was determined by x-ray crystallography.

Example 13

Synthesis of Mannich Base N-Oxide 28 Derived from N-Methyl-p-toluenesulfonamide and N,N-Dimethylmethyleneammonium Chloride (23).

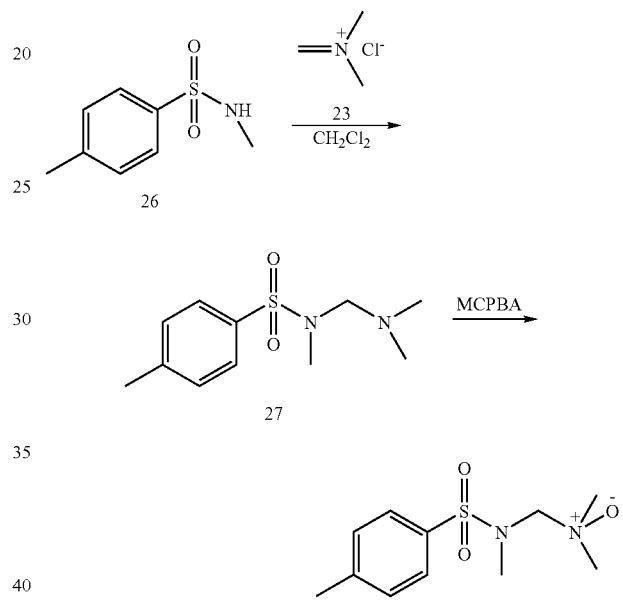

N-(Dimethylaminomethyl)-N-methyl-p-toluenesulfonamide (27) and N-(Dimethylamino-N'-oxido-methyl)-N-methyl-p-toluenesulfonamide (28). N-Methyl-p-toluenesulfonamide 26 0.30 g (1.6 mmol) was dissolved in 4 mL of dichloromethane. To this solution N,N-dimethylmethyleneammonium chloride (23) (0.20 g, 2.0 mmol) was added. The solution was stirred for 2 h at RT. After that time the solution was cooled down in water/ice bath and K$_2$CO$_3$ (0.43 g, 3.0 mmol) was added. To the resulting stirred mixture containing 27 was added solid MCPBA (0.40 g, 2.3 mmol). The mixture was stirred for 2 h and filtered through a pad of MgSO$_4$ to give crude Mannich base N-oxide 28 as an oil. The crude product was passed through a short silica gel column to remove polar impurities. The resulting dichloromethane solution was concentrated and then chromatographed on a Chromatotron with dichloromethane/methanol mixture as an eluent (5:0.3 to 5:2) to give pure N-oxide 28 as an oil (0.07 g, 17% yield) which solidified in freezer. APCI MS (m/z): Calcd. for C$_{11}$H$_{18}$N$_2$O$_3$S (M+H), 259.1. Found (M+H) 259.1. A sample was recrystallized from Et$_2$O producing crystals that were analyzed by x-ray crystallography.

Example 14

Synthesis of Indole Mannich Bases N-Oxides.

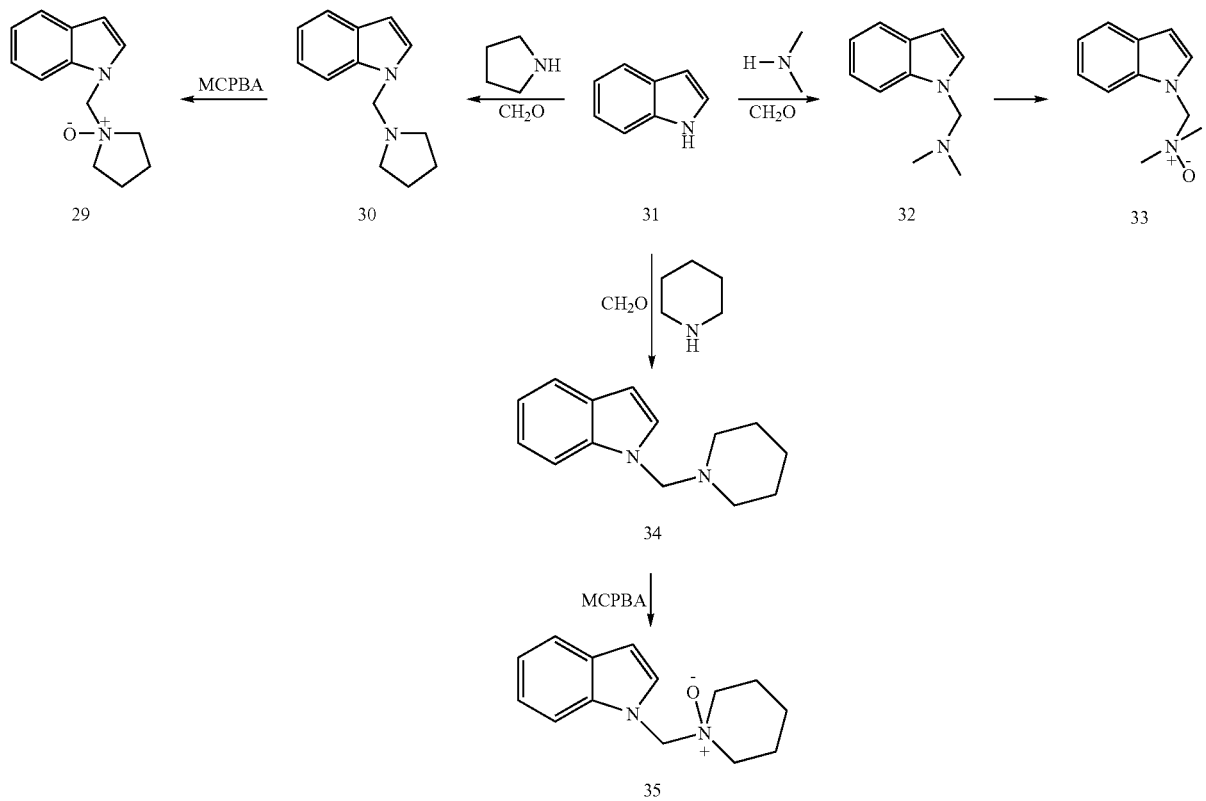

N-(Dimethylaminomethyl)-indole (32). Formaldehyde (37% in water, 0.19 mL, 2.6 mmol) was added to cooled (ice/water bath) aqueous dimethylamine (40% in water, 0.32 mL, 2.6 mmol). The mixture was stirred for 10 min and then indole 31 (0.3 g, 2.6 mmol) was added. The suspension was stirred for 1 h in an ice/water bath and then 24 h at RT. Indole was not completely dissolved. Dichloromethane (10 mL) was added and the organic layer was separated. The solvent was evaporated and the residue was chromatographed on a Chromatotron with dichloromethane/hexanes, 5:2 mixture as eluent to remove non-polar impurities. This was followed by elution with dichloromethane/EtOAc, 5:1 to 1:1. Appropriate fractions were collected to give indole Mannich base 32 as an oil (0.25 g, 57%) which was pure by TLC.

N-(Dimethylamino-N'-oxido-methyl)-indole (33). N-(dimethylaminomethyl)-indole 32 (0.055 g, 0.30 mmol) was dissolved in dichloromethane (1 mL). To this solution $K_2CO_3$ (0.16 g, 0.5 mmol) was added. The stirred mixture was cooled in ice/water bath. MCPBA (0.081 g, 0.34 mmol) was added as a solid to the above mixture. TLC (dichloromethane/methanol, 5:0.5) showed the formation of a new more polar spot over 5 min. The resulting mixture was stirred for 24 h, and then it was filtered through celite and evaporated. The resulting crude N-oxide was chromatographed on a Chromatotron with dichloromethane/methanol, 5:0.5 to 5:3, as eluent. The desired fractions were combined and concentrated to dryness affording N-oxide 33 as an off white solid (0.04 g, 75%) which was pure by TLC and $^1$H NMR.

N-[(1-Pyrrolidinyl-1-oxido)-methyl]-indole (29) and N-[(1-Piperidinyl-1-oxido)-methyl]-indole (35) was prepared following the same procedure that was used for the preparation of Mannich base N-oxide 33.

We observed that indole-derived Mannich bases 30, 32 and 34, unlike the other Mannich bases herein described, were quite stable toward hydrolysis. For example, only 30% of Mannich base 34 was hydrolyzed after 80 h in $D_2O$.

Example 15

Cytotoxicity of 5-FU Analog or Prodrug N-Oxides Thereof in Lymphoma, Leukemia, and Multiple Myeloma The cytotoxicity of 5-FU analog or prodrug N-oxides thereof on different lymphoma, leukemia, and multiple myeloma cell lines will be tested in vitro under normoxic as well as 1% $O_2$ hypoxic conditions. Standard cytotoxicity assays using MTS dye will be run to determine the $IC_{50}$ for each compound. Cells will be exposed to the compounds for 24 hours and cells will be stained 24-72 hours post-drug exposure. Positive controls will use chemotherapeutic agents at doses shown in the art to be effective. The results should indicate that 5-FU analogs or prodrugs are cytotoxic to many of the cell lines, with $IC_{50}$ values in the nanomolar to sub-nanomolar range. 5-FU analog or prodrug N-oxides are expected to be less active or inactive compared to non-N-oxide under normoxic conditions. However, under 1% $O_2$ hypoxic conditions, 5-FU analog or prodrug N-oxides are expected to be converted to the corresponding parent non-N-oxide, which may lead to the degradation of the Mannich base and release of the 5-FU analog or prodrug. The 5-FU analogs or prodrugs are expected to be cytotoxic with $IC_{50}$ values in the millimolar to sub-nanomolar range.

Example 16

Cytotoxicty of 5-FU Analog or Prodrug N-Oxides Thereof in Solid Tumor Lines

The cytotoxicity of 5-FU analog or prodrug N-oxides thereof on different solid tumor cell lines will be tested in vitro under normoxic conditions and 1% $O_2$ hypoxic conditions. Standard cytotoxicity assays using MTS dye will be run to determine the $IC_{50}$ for each compound. Cells will be exposed to the compounds for 24 hours and cells will be stained 24-72 hours post-drug exposure. Chemotherapeutic agents at doses shown in the art to be effective will be used as positive controls. The results are expected to indicate that 5-FU analogs or prodrugs are cytotoxic to many of the cell lines, with $IC_{50}$ values in the nanomolar to sub-nanomolar range. 5-FU analog or prodrug N-oxides thereof are expected to be less active or inactive compared to the corresponding 5-FU analogs or prodrugs.

Example 17

Anti-Proliferative Activity of 5-FU Analog of Prodrug N-Oxides Thereof in Cancer Cells The anti-proliferative activity of 5-FU analog or prodrug N-oxides thereof on established and primary cancer cells and cancer cell lines will be tested in vitro under normoxic and 1% $O_2$ hypoxic conditions at concentrations ranging from 1 nM to 10 mM. The anti-proliferative effect will be measured using the 5-bromo-2'-deoxyuridine ("BrDU") incorporation technique. The cells will be exposed to the compounds in the presence of BrDU for 24 hours. BrDU is incorporated into the replicating cellular DNA. After cell fixation and washing, the incorporated BrDU is determined in a specific ELISA using an antibody specific to BrDU coupled to peroxidase. The N-oxides are expected not to have significant anti-proliferative activity in cancer cells at concentrations of up to 10 mM under normoxia. However, the N-oxides are expected to exhibit significant anti-proliferative effect on the cancer cell lines under 1% $O_2$ hypoxia.

Example 18

Anti-Tumor Activity of Mannich Base N-Oxides of NH-Acidic Containing Antihyperproliferative Drugs in Murine Tumor Models The in vivo antitumor efficacy of Mannich base N-oxides of NH-acidic containing drugs will be evaluated using xenograft murine models. For example, male 5 to 6 week old nude mice will be inoculated subcutaneously in the mammary fat pad on each side with an injection of a human cancer cell line, for example about $1 \times 10^6$ MDA-MB-231 (2LMP) in 0.3 ml serum free medium. The best xenograft recipients will be used. Treatments with a Mannich base N-oxide of an NH-acidic containing drug will begin when tumors average about 5-7 mm in diameter and will be continued for 4 weeks with a 2 month follow up period.

Test animals will be divided into cohort groups of 5-8 animals into the following treatment groups: Control (Group 1); Vehicle Control (Group 2), daily administration of the vehicle only; and the Mannich base N-oxide test groups (Test Groups). Varying doses of the Mannich base N-oxide test drug will be administered to the Test Groups, with doses varying from approximately one-tenth to approximately 10 times the usual per kg dosage of the parent test drug (i.e., the non-Mannich base N-oxide). For example, Table 1 lists doses reported for some antiproliferative drugs and corresponding test doses that one skilled in the art may start with to test the efficacy of the corresponding Mannich base N-oxides of the parent drug.

TABLE 1

Representative Test Doses for Mannich base N-oxide compounds

| Non-Mannich Base N-oxide | Dose* | Test Doses for the Mannich Base N-oxide |
|---|---|---|
| Cytarabine | 0.5-2.5 mg/kg | 0.05-25 mg/kg |
| Carmustine | 200 mg/m² | 20-2000 mg/m² |
| Cyclophosphamide | 1-5 mg/kg | 0.1-50 mg/kg |
| Dacarbazine | 2-4.5 mg/kg | 0.2-45 mg/kg |
| Fluorouracil | 15 mg/kg | 1.5-150 mg/kg |
| Floxuridine | 0.1-0.6 mg/kg | 0.01-6 mg/kg |
| Lomustine | 130 mg/m² | 13-1300 mg/m² |
| Melphalan | 0.1-0.25 mg/kg | 0.01-2.5 mg/kg |
| Mercaptopurine | 2.5 mg/kg | 0.25-25 mg/kg |
| Methotrexate | 3-30 mg/m² | 0.3-300 mg/m² |
| Thioguanine | 2-3 mg/kg | 0.2-30 mg/kg |

*see Harvey, S. C., "Antineoplastic and Immunosuppressive Drugs," in Remington's Pharmaceutical Sciences, Osol, A. et al., eds., Mack Publishing Company, Easton, PA, pp. 1081-1098 (1980).

The test doses may further be increased or decreased upon recognition that such a modification is warranted for a particular test compound. For example, a particular Mannich base N-oxide may exert its own, for example, antiproliferative effect, making it more effective than it would have been had the Mannich base N-oxide been biologically inactive. In such a circumstance, lower doses of the Mannich base N-oxide may prove effective. Moreover, more cohort groups may be added to test additional doses of various Mannich base N-oxides of NH-acidic containing drugs.

During the treatment course, tumor sizes and animal weights will be measured periodically, for example 1-3 times per week for each animal. Following treatment, tumor sizes will be measured periodically, for example, 1-3 times per week, and animal weights once per week. Tumor size and weight observations will be made without knowledge of the animal's treatment group.

The data will be modeled using, for example, the natural logarithm of tumor volume versus time. Comparisons of the growth rates of animals administered with varying dosages will be performed. For example, Tumor Growth Delay and Tumor Growth Inhibition for varying dosages will be compared to the control.

Further, the in vivo antitumor activity of Mannich base N-oxide in combination with chemotherapeutic agents and/or radiotherapy will be evaluated using a xenograft model in nude mice.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound having Formula IV:

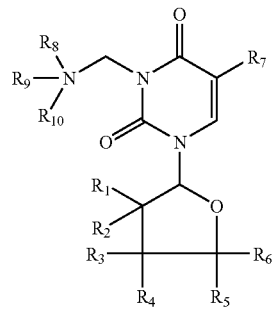

or a pharmaceutically acceptable salt thereof, wherein:

each of $R_1$-$R_4$ is independently hydrogen, hydroxy; OC(=O)$R_{11}$,O$R_{12}$ or one of $R_1$ and $R_2$ and one of $R_3$ and $R_4$ together form a double bond or a —OC(=$X^3$)O— group, wherein $X^3$ is S or O;

each of $R_5$ and $R_6$ is independently hydrogen, alkyl, $CH_2OR_{13}$ or C(=O)—CR'R"H; wherein R' is alkyl, alkoxy, or trifluoroacetamido; R" is phenyl or phenylmethyl;

$R_7$ is hydrogen, halo, alkyl, amine, alkylamine, dialkylamine, dialkylamine N-oxide, trifluoromethyl or trifluoromethyl amine;

each of $R_8$ and $R_9$ is independently alkyl, aryl, aralkyl, alkoxyalkyl, hydroxyalkyl, or $R_8$ and $R_9$ together with the nitrogen to which they are attached form a heterocyclic ring comprising one, two or three heteroatoms selected from the group consisting of N, O, S, SO and $SO_2$, said heterocycle having 1-4 substituents selected from the group consisting of hydroxy, alkoxy, halogen or hydroxyalkyl;

$R_{10}$ is O or is absent, provided that $R_{10}$ is O when $R_7$ is not dialkylamine N-oxide;

$R_{11}$ is hydrogen, acyl, alkylcarboxy, alkyl;

$R_{12}$ is hydrogen, acyl or a group of the formula:

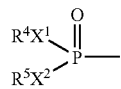

wherein $X^1$ and $X^2$ are independently O or S; $R^4$ is optionally substituted phenyl, optionally substituted benzyl or optionally substituted naphthyl; $R^5$ is alkyl or alkenyl; and $R_{13}$ is hydrogen, acyl, alkylcarboxy, alkyl, aralkyl, a monosaccharide, or a group of the formula:

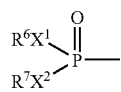

wherein $X^1$ and $X^2$ are independently O or S; $R^6$ is optionally substituted phenyl, optionally substituted benzyl or optionally substituted naphthyl; $R^7$ is alkyl or alkenyl.

2. The compound of claim 1, having formula V:

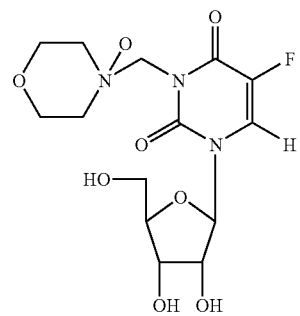

or a pharmaceutically acceptable salt thereof.

3. The compound of claim 1, having formula VI:

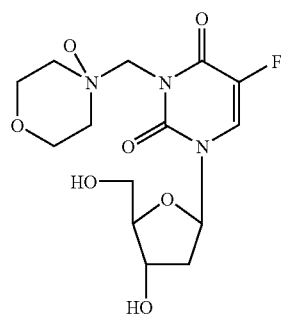

or a pharmaceutically acceptable salt thereof.

4. The compound of claim 1, wherein said compound of Formula IV is tegafur Mannich base N-oxide having the formula VII:

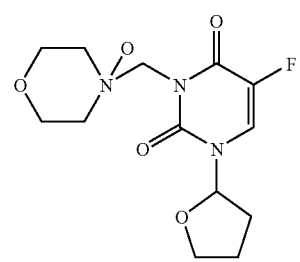

or a pharmaceutically acceptable salt thereof.

5. A method of treating or ameliorating cancer of the bladder, brain, breast, cervix, colon, endometrium, esophagus, head and neck, kidney, larynx, liver, lung, oral cavity, ovaries, pancreas, prostate, skin, stomach, or testis comprising administering to an animal in need thereof a therapeutically effective amount of a compound of claim 1, or a pharmaceutically acceptable salt thereof.

6. A method of treating or ameliorating cancer in an animal in need thereof, comprising
   (a) determining whether said cancer is characterized by hypoxic tissue, and
   (b) administering to said animal an effective amount of a compound of claim 1, or a pharmaceutically acceptable salt thereof.

7. The method of claim 5 or 6, further comprising administering one or more other active agents or treatments to the animal.

8. A pharmaceutical composition comprising a compound of claim 1, or a pharmaceutically acceptable salt thereof, and a pharmaceutically acceptable carrier.

9. The pharmaceutical composition of claim 8, wherein said compound is tegafur Mannich base N-oxide having the formula:

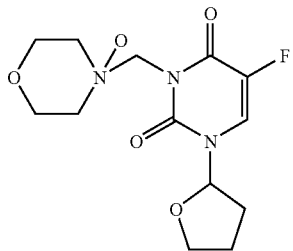

or a pharmaceutically acceptable salt thereof.

10. The pharmaceutical composition of claim 8, wherein said compound has formula V:

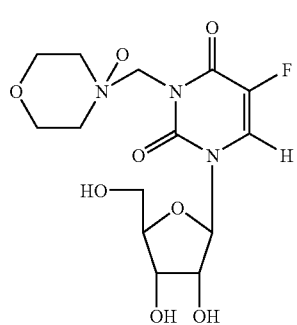

or a pharmaceutically acceptable salt thereof.

11. The pharmaceutical composition of claim 8, wherein said compound has formula IV:

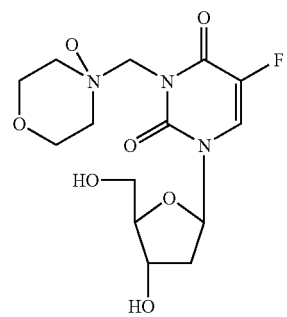

or a pharmaceutically acceptable salt thereof.

* * * * *